(12) United States Patent
Falentin et al.

(10) Patent No.: US 9,012,718 B2
(45) Date of Patent: Apr. 21, 2015

(54) BRASSICA NAPUS PLANTS COMPRISING MUTATED FAD2 ALLELES

(75) Inventors: Cyril Falentin, Mordelles (FR); Michel Bregeon, Mordelles (FR); Marie Odile Lucas, Cintre (FR); Michel Renard, Le Rheu (FR)

(73) Assignee: Institut National de la Recherche Agronomique (INRA), Paris Cedex (FR)

( * ) Notice: Subject to any disclaimer, the term of this patent is extended or adjusted under 35 U.S.C. 154(b) by 1186 days.

(21) Appl. No.: 12/302,321

(22) PCT Filed: May 25, 2007

(86) PCT No.: PCT/IB2007/001384
§ 371 (c)(1),
(2), (4) Date: Aug. 21, 2009

(87) PCT Pub. No.: WO2007/138444
PCT Pub. Date: Dec. 6, 2007

(65) Prior Publication Data
US 2009/0307806 A1 Dec. 10, 2009

(30) Foreign Application Priority Data
May 29, 2006 (EP) ..................................... 06290855

(51) Int. Cl.
*A01H 1/06* (2006.01)
*A01H 5/10* (2006.01)
*C07H 21/04* (2006.01)
*C12N 9/02* (2006.01)
*C12N 15/82* (2006.01)

(52) U.S. Cl.
CPC .......... *C12N 9/0083* (2013.01); *C12N 15/8247* (2013.01)

(58) Field of Classification Search
None
See application file for complete search history.

(56) References Cited

U.S. PATENT DOCUMENTS

| 6,414,223 | B1 | 7/2002 | Kodali et al. |
| 2005/0039233 | A1 | 2/2005 | Yao et al. |
| 2006/0248611 | A1 | 11/2006 | Hu et al. |

FOREIGN PATENT DOCUMENTS

EP 0 945 514 9/1999

OTHER PUBLICATIONS

Hohe et al 2003 Plant Cell Reports 21:1135-1142.*

* cited by examiner

*Primary Examiner* — Elizabeth McElwain
*Assistant Examiner* — Matthew Keogh
(74) *Attorney, Agent, or Firm* — B. Aaron Schulman, Esq.; Stites & Harbison, PLLC.

(57) ABSTRACT

The present invention relates to a mutated nucleic acid sequence of a delta-12 oleate desaturase enzyme (FAD2)—encoding nucleic acid from a Cruciferae plant, wherein said mutated nucleic acid sequence comprises the non-conservative mutation of at least one nucleotide of at least one codon representing an amino acid selected from the group consisting of: —the amino acid at position 259 of the amino acid sequence of said FAD2, —the amino acid at position 216 of the amino acid sequence of said FAD2, —the amino acid at position 90 of the amino acid sequence of said FAD2, —the amino acid at position 116 of the amino acid sequence of said FAD2, —the amino acid at position 276 of the amino acid sequence of said FAD2.

22 Claims, 19 Drawing Sheets

```
fad2A'LLR1' : AGTGTCTCCTCCCTCCAAAAAGTCTGAAAACGACAACATCAAGCGCGTACCCTGCGAGACACCGCCCTTCACTGTCGGAGAA :  82
fad2A'HOR1' : AGTGTCTCCTCCCTCCAAAAAGTCTGAAAACGACAACATCAAGCGCGTACCCTGCGAGACACCGCCCTTCACTGTCGGAGAA :  82 fad2A'LLR1' : CTCAAGAAAGCAATCCACCGCACTGTTCAAACGCTCGATCCCTGGCTCTTTCTCCTACCTCATCTGGGACATCATCATAG   : 164
fad2A'HOR1' : CTCAAGAAAGCAATCCACCGCACTGTTCAAACGCTCGATCCCTGGCTCTTTCTCCTACCTCATCTGGGACATCATCATAG   : 164 fad2A'LLR1' : CCTCCTGCTTCTACTACGTCGCCACCACTACTTCCCCTCTCTCCCTCACCCTCTCCTACTTCGCCTGGCCTCTCTACTG    : 246
fad2A'HOR1' : CCTCCTGCTTCTACTACGTCGCCACCACTACTTCCCCTCTCTCCCTCACCCTCTCCTACTTCGCCTGGCCTCTCTACTG    : 246 fad2A'LLR1' : GGCCTGCCAGGGCTGCGTCCTAACCGGCGTCTGGGTCATAGCCCACGAGTGCGGCCACCACGCCTTCAGCGACTACCAGTGG : 328
fad2A'HOR1' : GGCCTGCCAGGGCTGCGTCCTAACCGGCGTCTGGGTCATAGCCCACGAGTGCGGCCACCACGCCTTCAGCGACTACCAGTGG : 328 fad2A'LLR1' : CTGGACGACACCGTCGGCCCTCATCTTCCACTCTTCCTCCTCGTCCCTTACTTCTCCTGGAAGTACAGTCATCGACGCCACC : 410
fad2A'HOR1' : CTGGACGACACCGTCGGCCCTCATCTTCCACTCTTCCTCCTCGTCCCTTACTTCTCCTGGAAGTACAGTCATCGACGCCACC : 410 fad2A'LLR1' : ATTCCAACACTGGCTCCCTCGAGAGAGACGAAGTGTTTGTCCCCAAGAGAAGTCAGACATCAAGTGGTACGGCCAAGTACCT : 492
fad2A'HOR1' : ATTCCAACACTGGCTCCCTCGAGAGAGACGAAGTGTTTGTCCCCAAGAGAAGTCAGACATCAAGTGGTACGGCCAAGTACCT : 492 fad2A'LLR1' : CAACAACCCTTGGGACGCACCGTGATGTTAACGGTTCAGTTCACTCTCGGCCTGGCCTTTGTACTTAGCCTTCAACGTCTCG : 574
fad2A'HOR1' : CAACAACCCTTGGGACGCACCGTGATGTTAACGGTTCAGTTCACTCTCGGCCTGGCCTTTGTACTTAGCCTTCAACGTCTCG : 574 fad2A'LLR1' : GGGAGACCTTACGACGGGCGGCTTCGCTTGCCATTTCCACCCAACGCTCCATCTACAACGACCGTGAGCGCTCCAGATAT   : 656
fad2A'HOR1' : GGGAGACCTTACGACGGGCGGCTTCGCTTGCCATTTCCACCCAACGCTCCATCTACAACGACCGTGAGCGCTCCAGATAT   : 656
```

Fig. 1a

```
fad2A'LLR1' :  ACATCTCCGACGCTGGCATCCTCGCCGTCTGCTCCGGTCTCTACCGCTCTGCTGTCCAAGGAGTTGCCTCTATGGTCTG   738
fad2A'HOR1' :  ACATCTCCGACGCTGGCATCCTCGCCGTCTGCTCCGGTCTCTACCGCTCTGCTGTCCAAGGAGTTGCCTCTATGGTCTG   738
                        *         *         *         *         *         *         *
                       660       680       700       720                             7
                                                                           ▼
                        40        *         *         *         *         *         820
fad2A'LLR1' :  CTTCTACGGAGTTCCTCTTCTGATTGTCAACGGGTTCTTAGTTTTGATCACTTACTTGCAGCACACGCATCCTTCCCTGCCT   820
fad2A'HOR1' :  CTTCTACGGAGTTCCTCTTCTGATTGTCAACGGGTTCTTAGTTTTGATCACTTACTTGCAGCACACGCATCCTTCCCTGCCT   820
               Forward primer
                        *         *         *         *         *         *         900
                       760       780       800                                       
fad2A'LLR1' :  CACTATGACTCGTCTGAGTGGGATTGGTTGAGGGGAGCTTTGGCCACCGTTGACAGAGACTACGGAATCTTGAACAAGGTCT   902
fad2A'HOR1' :  CACTATGACTCGTCTGAGTGGGATTGGTTGAGGGGAGCTTTGGCCACCGTTGACAGAGACTACGGAATCTTGAACAAGGTCT   902
                        *         *         *         *         *         *         980
                       840       860       880                                       
fad2A'LLR1' :  TCCACAATATCACGGACACGCACGTGGGCGCCATCACCTGTTCTCGACCATGCCGCATTATCATGCGATGGAAGCTACGAAGGC   984
fad2A'HOR1' :  TCCACAATATCACGGACACGCACGTGGGCGCCATCACCTGTTCTCGACCATGCCGCATTATCATGCGATGGAAGCTACGAAGGC   984
                        Reverse primer
                        *         *         *         *         *         *         1060
                       920       940       960                                       
fad2A'LLR1' :  GATAAAGCCGATACTGGGACGCCGGTGTTAAGGCGATGTGGAGGAGGCGAAGGAGTGT   1066
fad2A'HOR1' :  GATAAAGCCGATACTGGGACGCCGGTGTTAAGGCGATGTGGAGGAGGCGAAGGAGTGT   1066
                        *         *         *         *
                       1000      1020      1040                                      
fad2A'LLR1' :  ATCTATGTGGAACCGGACAGGCAAGGTGAGAAGA   1100
fad2A'HOR1' :  ATCTATGTGGAACCGGACAGGCAAGGTGAGAAGA   1100
                        *
                       1080      1100
```

Fig. 1b

```
fad2C'LLR1' : AGTGTCTCCTCCCTCCAAAAAGTCTGAAACCGACACCATCAAGGCGTACCCTGCGAGACACCGCCCTTCACTGTCGGAGAA :  82
fad2C'HOR1' : AGTGTCTCCTCCCTCCAAAAAGTCTGAAACCGACACCATCAAGGCGTACCCTGCGAGACACCGCCCTTCACTGTCGGAGAA :  82 fad2C'LLR1' : CTCAAGAAAGCAATCCCACCGCACTGTTCAAACGCTCGATCCCTCGCTCTTTCTCCTACCTCATCTGGACATCATCATAG  : 164
fad2C'HOR1' : CTCAAGAAAGCAATCCCACCGCACTGTTCAAACGCTCGATCCCTCGCTCTTTCTCCTACCTCATCTGGACATCATCATAG  : 164 fad2C'LLR1' : CCTCCTGCTTCTACTACGTCGCCACCACTTACTTCCCTCTCTCCCTCACCCTTCGCCTGGCCTCTCTACTG           : 246
fad2C'HOR1' : CCTCCTGCTTCTACTACGTCGCCACCACTTACTTCCCTCTCTCCCTCACCCTTCGCCTGGCCTCTCTACTG           : 246 fad2C'LLR1' : GGCCTGCCAAGGGTGCGTCCTAACCGGCGTCTGGGTCATAGCCACGAGTGCGGCCACCACGCCTTCAGCGACTACCAGTGG : 328
fad2C'HOR1' : GGCCTGCCAAGGGTGCGTCCTAACCGGCGTCTGGGTCATAGCCACGAGTGCGGCCACCACGCCTTCAGCGACTACCAGTGG : 328 fad2C'LLR1' : CTTGACGACACCGTCGGTCTCATCTCCACTCTTCCTCGTCCCTCCTTCCTGGAAGTACAGTCATCGACGCCACC         : 410
fad2C'HOR1' : CTTGACGACACCGTCGGTCTCATCTCCACTCTTCCTCGTCCCTCCTTCCTGGAAGTACAGTCATCGACGCCACC         : 410 fad2C'LLR1' : ATTCCAACACTGGCTCCCTCGAGAGAGACGAAGTGTTTGTCCCCAAGAAGAAGTCAGACATCAAGTGGTACGGCAAGTACCT : 492
fad2C'HOR1' : ATTCCAACACTGGCTCCCTCGAGAGAGACGAAGTGTTTGTCCCCAAGAAGAAGTCAGACATCAAGTGGTACGGCAAGTACCT : 492 fad2C'LLR1' : CAACAACCCTTTGGGACGCACCGTGATGTTAACGGTTCAGTTCACTCTCGGCTGGCCGTTGTACTTAGCCTTCAACGTCTCG : 574
fad2C'HOR1' : CAACAACCCTTTGGGACGCACCGTGATGTTAACGGTTCAGTTCACTCTCGGCTGGCCGTTGTACTTAGCCTTCAACGTCTCG : 574 fad2C'LLR1' : GGAAGACCTTACGACGGCGGCTTCGCTTGCCATTTCCACCCCAAACGCTTCCATTCACCCCAAACGCTTCCATTCTACAACGACCGCGAGCGTCTCCAGATAT : 656
fad2C'HOR1' : GGAAGACCTTACGACGGCGGCTTCGCTTGCCATTTCCACCCCAAACGCTTCCATTCACCCCAAACGCTTCCATTCTACAACGACCGCGAGCGTCTCCAGATAT : 656
                                                            Forward primer
```

Fig. 2a

```
              660         *         680         *         700         *         720         *
fad2C'LLR1' : ACATCTCCGACGCTGGCATCCTCCGCGTCTGCCGGTCTCTTCCGTTACGCCGCCGCGCCAGGGAGTGGCCTCGATGGTCTG : 738
fad2C'HOR1' : ACATCTCCGACGCTGGCATCCTCCGCGTCTGCCGGTCTCTTCCGTTACGCCGCCGCGCCAGGGAGTGGCCTCGATGGTCTG : 738
                                                                        Reverse primer
              740         *         760         *         780         *         800         *       820
fad2C'LLR1' : CTTCTACGGAGTCCCGCTTCTGATTGTCAATGGTTTCCTCGTGTTGATCACTTACTTGCAGCACACGCATCCTTCCCTGCCT : 820
fad2C'HOR1' : CTTCTACGGAGTCCCGCTTCTGATTGTCAATGGTTTCCTCGTGTTGATCACTTACTTGCAGCACACGCATCCTTCCCTGCCT : 820

*         840         *         860         *         880         *       900
fad2C'LLR1' : CACTACGATTCGTCCGAGTGGGATTGGTTGAGGGGAGCTTTGGCTACCGTTGACAGAGACTACGGAATCTTGAACAAGGTCT : 902
fad2C'HOR1' : CACTACGATTCGTCCGAGTGGGATTGGTTGAGGGGAGCTTTGGCTACCGTTGACAGAGACTACGGAATCTTGAACAAGGTCT : 902

*         920         *         940         *         960         *       980
fad2C'LLR1' : TCCACAATATTACCGACACGCACGTGGCGCATCATCTGTTCTCCACGATGCCGCATTATCACGCGATGGAAGCTACCAAGGC : 984
fad2C'HOR1' : TCCACAATATTACCGACACGCACGTGGCGCATCATCTGTTCTCCACGATGCCGCATTATCACGCGATGGAAGCTACCAAGGC : 984

*         1000        *         1020        *         1040        *       1060
fad2C'LLR1' : GATAAAGCCGATACTGGGAGAGTATTATCAGTTCGATGGGACGCCGGTTGGTTAAGGCGATGTGGAGGAGGCGAAGGAGTGT : 1066
fad2C'HOR1' : GATAAAGCCGATACTGGGAGAGTATTATCAGTTCGATGGGACGCCGGTTGGTTAAGGCGATGTGGAGGAGGCGAAGGAGTGT : 1066

*         1080        *         1100
fad2C'LLR1' : ATCTATGTGGAACCGGACAGGCAAGGTGAGAAGA : 1100
fad2C'HOR1' : ATCTATGTGGAACCGGACAGGCAAGGTGAGAAGA : 1100
```

Fig. 2b

```
fad2A'LLR1' : AGTGTCTCCTCCCTCCAAAAAGTCTGAAACCGACAACATCAAGGGCGTACCCTGCGAGACACCGCCCTTCACTGTCGGAGAA :  82
fad2A'HOR2' : AGTGTCTCCTCCCTCCAAAAAGTCTGAAACCGACAACATCAAGGGCGTACCCTGCGAGACACCGCCCTTCACTGTCGGAGAA :  82 fad2A'LLR1' : CTCAAGAAAGCAATCCCACCGCACTGTTTCAAACGCTCGATCCCTCCTACCTCATCTGGACATCATCATAG : 164
fad2A'HOR2' : CTCAAGAAAGCAATCCCACCGCACTGTTTCAAACGCTCGATCCCTCCTACCTCATCTGGACATCATCATAG : 164 fad2A'LLR1' : CCTCCTGCTTCTACTACGTCGCCACCACTACTTCCCTCCTCCCTCACCCTCCCTCCTCCGCCTCTCTACTG : 246
fad2A'HOR2' : CCTCCTGCTTCTACTACGTCGCCACCACTACTTCCCTCCTCCCTCACCCTCCCTCCTCCGCCTCTCTACTG : 246 fad2A'LLR1' : GGCCTGCCAGGGCTGCGTCCTAACCGGCGTCTGGGTCATAGCCACGAGTGCGGCCACCACGCCTTCAGCGACTACCAGTGG : 328
fad2A'HOR2' : GGCCTGCCAGGGCTGCGTCCTAACCGGCGTCTGGGTCATAGCCACGAGTGCGGCCACCACGCCTTCAGCGACTACCAGTGG : 328 fad2A'LLR1' : CTGGACGACACCGTCGGGCCTCATCTTCCACTCTTCCTCCTCGTCCCTTACTTCTCCTGGAAGTACAGTCATCGACGCCACC : 410
fad2A'HOR2' : CTGGACGACACCGTCGGGCCTCATCTTCCACTCTTCCTCCTCGTCCCTTACTTCTCCTGGAAGTACAGTCATCGACGCCACC : 410 fad2A'LLR1' : ATTCCAACACTGGCTCCCTGAGAGAGAGACGAAGTGTTTGTCCCCAAGAAGTCAGACATCAACTGGTACGGCAAGTACCT : 492
fad2A'HOR2' : ATTCCAACACTGGCTCCCTGAGAGAGAGACGAAGTGTTTGTCCCCAAGAAGTCAGACATCAACTGGTACGGCAAGTACCT : 492 fad2A'LLR1' : CAACAACCCTTTGGGACGCACCGTGATGTTAACGGTTCAGTTCAGTTTCACTCTCGGCCTGGCCTTTGTACTTAGCCTTCAACGTCTCG : 574
fad2A'HOR2' : CAACAACCCTTTGGGACGCACCGTGATGTTAACGGTTCAGTTCAGTTTCACTCTCGGCCTGGCCTTTGTACTTAGCCTTCAACGTCTCG : 574 fad2A'LLR1' : GGGAGACCTTACGACGGCGGCTTCGCTTGCCATTTCCACCCCAAGCGCTCCATCTACAACGACCGTGAGCGTCTCCAGATAT : 656
fad2A'HOR2' : GGGAGACCTTACGACGGCGGCTTCGCTTGCCATTTCCACCCCAAGCGCTCCATCTACAACGACCGTGAGCGTCTCCAGATAT : 656
```

Fig. 3a

```
                  660         *         680         *         700         *         720         *
fad2A'LLR1' : ACATCTCCGACGCTGGCATCCTCGCCGTCTGCTCGTCTGCTCGTACGGTCTCTACCGCTACGCTGCTGTCCAAGGAGTTGCCTCTATGGTCTG : 738
fad2A'HOR2' : ACATCTCCGACGCTGGCATCCTCGCCGTCTGCTCGTCTGCTCGTACGGTCTCTACCGCTACGCTGCTGTCCAAGGAGTTGCCTCGATGGTCTG : 738
                                                                    Forward primer
                   40         *         760         *         780         *         800         *         820
fad2A'LLR1' : CTTCTACGGAGTTCCTCTTCTGATTGTCAACGGGTTCTTAGTTTTGATCACTTACTTGCAGCACACGCATCCTTCCCTGCCT : 820
fad2A'HOR2' : CTTCTACGGAGTTCCTCTTCTGATTGTCAACGGGTTCTTAGTTTTGATCACTTACTTGCAGCACACATGCATCCTTCCCTGCCT : 820
                                                                                                              Reverse primer
                    *         840         *         860         *         880         *         900
fad2A'LLR1' : CACTATGACTCGTCTGAGTGGGATTGGTTGAGGGGAGCTTTGGCCACCGTTGACAGAGACTACGGAATCTTGAACAAGGTCT : 902
fad2A'HOR2' : CACTATGACTCGTCTGAGTGGGATTGGTTGAGGGGAGCTTTGGCCACCGTTGACAGAGACTACGGAATCTTGAACAAGGTCT : 902
                    *         920         *         940         *         960         *         980
fad2A'LLR1' : TCCACAATATCACGGACACGCCACGTGGCGCATCCTGTTCTCGACCATGCCGCATTATCATGCCGATGGAAGCTACGAAGGC : 984
fad2A'HOR2' : TCCACAATATCACGGACACGCCACGTGGCGCATCCTGTTCTCGACCATGCCGCATTATCATGCCGATGGAAGCTACGAAGGC : 984
                    *         1000        *         1020        *         1040        *         1060
fad2A'LLR1' : GATAAAGCCGATACTGGGAGAGTATTATCAGTTCGATGGACGCCGGTGGTTAAGGCCGATGTGGAGGGAGGCGAAGGAGTGT : 1066
fad2A'HOR2' : GATAAAGCCGATACTGGGAGAGTATTATCAGTTCGATGGACGCCGGTGGTTAAGGCCGATGTGGAGGGAGGCGAAGGAGTGT : 1066
                    *         1080        *         1100
fad2A'LLR1' : ATCTATGTGGAACCGGACAGGCAAGGTGAGAAGA : 1100
fad2A'HOR2' : ATCTATGTGGAACCGGACAGGCAAGGTGAGAAGA : 1100
```

Fig. 3b

|  |  |  | * | 20 | * | 40 | * | 60 | * | 80 |  |
|---|---|---|---|---|---|---|---|---|---|---|---|
| fad2A'LLR1' | : | AGTGTCTCCCTCCCTCCCTCCAAAAAGTCTGAAACCGACAACATCAAGCGGTACCCTGCGAGACACCGCCCTTCACTGTCGGAG | : | 80 |
| fad2A'HOR3' | : | AGTGTCTCCCTCCCTCCCTCCAAAAAGTCTGAAACCGACAACATCAAGCGGTACCCTGCGAGACACCGCCCTTCACTGTCGGAG | : | 80 |

|  |  |  | * | 100 | * | 120 | * | 140 | * | 160 |  |
|---|---|---|---|---|---|---|---|---|---|---|---|
| fad2A'LLR1' | : | AACTCAAGAAAGCAATCCACCGCACTGTTTCAAACGCTCGATCCCTCGCTCTTTCTCCTACCTCATCTGGGACATCATC | : | 160 |
| fad2A'HOR3' | : | AACTCAAGAAAGCAATCCACCGCACTGTTTCAAACGCTCGATCCCTCGCTCTTTCTCCTACCTCATCTGGGACATCATC | : | 160 |

|  |  |  | * | 180 | * | 200 | * | 220 | * | 240 |  |
|---|---|---|---|---|---|---|---|---|---|---|---|
| fad2A'LLR1' | : | ATAGCCTCCTGCTTCTACTACGTCGCCACCACTTACTTCCCCTCCACCCTCTCTCTCCTACTTCGCCTGGCCTCT | : | 240 |
| fad2A'HOR3' | : | ATAGCCTCCTGCTTCTACTACGTCGCCACCACTTACTTCCCCTCCACCCTCTCTCTCCTACTTCGCCTGGCCTCT | : | 240 |

|  |  |  | * | 260 | * | 280 | * | 300 | * | 320 |  |
|---|---|---|---|---|---|---|---|---|---|---|---|
| fad2A'LLR1' | : | CTACTGGGCCTGCCAGGGCTGCGTCCTAACCGGCTCTGGGTCATAGCCCACGAGTGCGGCCACCACGCCTTCAGCGACT | : | 320 |
| fad2A'HOR3' | : | CTACTGGGCCTGCCAGGGCTGCGTCCTAACCGGCTCTGGGTCATAGCCCACGAGTGCGGCCACCACGCCTTCAGCGACT | : | 320 |

|  |  |  | * | 340 | * | 360 | * | 380 | * | 400 |  |
|---|---|---|---|---|---|---|---|---|---|---|---|
|  |  |  |  |  |  |  |  |  | Forward primer |  |  |
| fad2A'LLR1' | : | ▶ ACCAGTGGCTGGACGACACCGTCGGCCTCATCTTCCACTCTCCTCCTTACTTCTCCTGAAGTACAGTCAT | : | 400 |
| fad2A'HOR3' | : | ACTAGTGGCTGGACGACACCGTCGGCCTCATCTTCCACTCTCCTCCTTACTTCTCCTGAAGTACAGTCAT | : | 400 |

|  |  |  | * | 420 | * | 440 | * | 460 | * | 480 |  |
|---|---|---|---|---|---|---|---|---|---|---|---|
| fad2A'LLR1' | : | CGACGCCACCATTCCAACACTGGCTCCCTCGAGAGAGAAGTGTTGTCCCCAAGAAGAAGTCAGACATCAAGTGGTA | : | 480 |
| fad2A'HOR3' | : | CGACGCCACCATTCCAACACTGGCTCCCTCGAGAGAGAAGTGTTGTCCCCAAGAAGAAGTCAGACATCAAGTGGTA | : | 480 |

|  |  |  | * | 500 | * | 520 | * | 540 | * | 560 |  |
|---|---|---|---|---|---|---|---|---|---|---|---|
| fad2A'LLR1' | : | CGGCAAGTACCTCAACAACCCTTTGGGACGCACCGTGATGTTAACGGTTCAGTTCACTCTCGGCTGGCCTTTGTACTTAG | : | 560 |
| fad2A'HOR3' | : | CGGCAAGTACCTCAACAACCCTTTGGGACGCACCGTGATGTTAACGGTTCAGTTCACTCTCGGCTGGCCTTTGTACTTAG | : | 560 |

|  |  |  | * | 580 | * | 600 | * | 620 | * | 640 |  |
|---|---|---|---|---|---|---|---|---|---|---|---|
| fad2A'LLR1' | : | CCTTCAACGTCTCGGGGAGACCTTACGACGGGCCTTCGCTTGCCATTTCCACCCCAACGCTCCCATCTACAACGACCGT | : | 640 |
| fad2A'HOR3' | : | CCTTCAACGTCTCGGGGAGACCTTACGACGGGCCTTCGCTTGCCATTTCCACCCCAACGCTCCCATCTACAACGACCGT | : | 640 |

Fig. 4a

```
                 *         660         *         680         *         700         *         720
fad2A'LLR1' : GAGCGTCTCCAGATATACATCTCCGACGCTGGCATCCTCGCCGTCTGCTACGGTCTCTACCGCTACGCTGCTGTCCAAGG : 720
fad2A'HOR3' : GAGCGTCTCCAGATATACATCTCCGACGCTGGCATCCTCGCCGTCTGCTACGGTCTCTACCGCTACGCTGCTGTCCAAGG : 720
                                                                                    Rever
                 *         740         *         760         *         780         *         800
fad2A'LLR1' : AGTTGCCTCTATGGTCTGCTTCTTCTACGGAGTTCCTCTTCTGATTGTCAACGGGTTCTTAGTTTTGATCACTTACTTGCAGC : 800
fad2A'HOR3' : AGTTGCCTCGATGGTCTGCTTCTTCTACGGAGTTCCTCTTCTGATTGTCAACGGGTTCTTAGTTTTGATCACTTACTTGCAGC : 800
              se primer
                 *         820         *         840         *         860         *         880
fad2A'LLR1' : ACACGCATCCTTCCCTGCCTCACTATGACTCGTCTGAGTGGGATTGGTTGAGGGAGCTTTGGCCACCGTTGACAGAGAC : 880
fad2A'HOR3' : ACACGCATCCTTCCCTGCCTCACTATGACTCGTCTGAGTGGGATTGGTTGAGGGAGCTTTGGCCACCGTTGACAGAGAC : 880
                 *         900         *         920         *         940         *         960
fad2A'LLR1' : TACGAATCTTGAACAAGGTCTTCCACAATATCACGGACACGCACGTGGCGCATCACCTGTTCTCGACCATGCCGCATTA : 960
fad2A'HOR3' : TACGAATCTTGAACAAGGTCTTCCACAATATCACGGACACGCACGTGGCGCATCACCTGTTCTCGACCATGCCGCATTA : 960
                 *         980         *         1000        *         1020        *         1040
fad2A'LLR1' : TCATGCGATGGAAGCTACGAAGGCGATAAAGCCGATAAAGCCGATAAAGCCGATAATATCAGTTCGATGGACGCCGGTGGTTAAGG : 1040
fad2A'HOR3' : TCATGCGATGGAAGCTACGAAGGCGATAAAGCCGATAAAGCCGATAAAGCCGATAATATCAGTTCGATGGACGCCGGTGGTTAAGG : 1040
                 *         1060        *         1080        *         1100
fad2A'LLR1' : CGATGTGGAGGAGGCGAAGGAGTGTATCTATGTGGAACCGGACAGGCAAGGTGAGAAGA : 1100
fad2A'HOR3' : CGATGTGGAGGAGGCGAAGGAGTGTATCTATGTGGAACCGGACAGGCAAGGTGAGAAGA : 1100
```

```
fad2A'LLR1' : GAGCGTCTCCAGATATACATCTCCGACGCGCTGGCATCCTCCGCCGTCTGCTGCTACGCTCTCTACCGCTGCTGCTGTCCAAGG : 720
fad2A'HOR4' : GAGCGTCTCCAGATATACATCTCCGACGCGCTGGCATCCTCCGCCGTCTGCTGCTACGCTCTCTACCGCTGCTGCTGTCCAAGG : 720
                                                                                       Rever
fad2A'LLR1' : AGTTGCCTCTATGGTCTGCTTCTTACGGAGTTCCTCTTCTGATTGTCAACGGGTTCTTAGTTTTGATCACTTACTTGCAGC : 800
fad2A'HOR4' : AGTTGCCTCGATGGTCTGCTTCTTACGGAGTTCCTCTTCTGATTGTCAACGGGTTCTTAGTTTTGATCACTTACTTGCAGC : 800
              se primer
fad2A'LLR1' : ACACGCATCCTTCCCTGCCTCACTATGACTCGTCTGAGTGGGATTGGTTGAGGGGAGCTTTGGCCACCGTTGACAGAGAC : 880
fad2A'HOR4' : ACACGCATCCTTCCCTGCCTCACTATGACTCGTCTGAGTGGGATTGGTTGAGGGGAGCTTTGGCCACCGTTGACAGAGAC : 880 fad2A'LLR1' : TACGGAATCTTGAACAAGGTCTTCCACAATATCACGGACACGCACGTGGCGCATCACCTGTTCTCGACCATGCCGCATTA : 960
fad2A'HOR4' : TACGGAATCTTGAACAAGGTCTTCCACAATATCACGGACACGCACGTGGCGCATCACCTGTTCTCGACCATGCCGCATTA : 960 fad2A'LLR1' : TCATGCGATGGAAGCTACGAAGGCGATAAAGCCGATACTGGGAGAGTATTATCAGTTCGATGGGACGCCGGTGGTTAAGG : 1040
fad2A'HOR4' : TCATGCGATGGAAGCTACGAAGGCGATAAAGCCGATACTGGGAGAGTATTATCAGTTCGATGGGACGCCGGTGGTTAAGG : 1040 fad2A'LLR1' : CGATGTGGAGGGAGGCGAAGGAGTGTATCTATGTGGAACCGGACAGGCAAGGTGAGAAGA : 1100
fad2A'HOR4' : CGATGTGGAGGGAGGCGAAGGAGTGTATCTATGTGGAACCGGACAGGCAAGGTGAGAAGA : 1100
```

Fig. 5b

```
                  *         20         *         40         *         60         *         80
fad2A'LLR1' : ------VSPPSKKKSETDNIKRVPCETPPFTVGELKKAIPPHCFKRSIPRSFSYLIWDIIIASCFYYVATTYFPLLPHPLSY  :  75
fad2A'HOR1' : ------VSPPSKKKSETDNIKRVPCETPPFTVGELKKAIPPHCFKRSIPRSFSYLIWDIIIASCFYYVATTYFPLLPHPLSY  :  75
B.rapa      : MGAGGRMQVSPPSKKKSETDNIKRVPCETPPFTVGELKKAIPPHCFKRSIPRSFSYLIWDIIIASCFYYVATTYFPLLPHPLSY  :  83
B.napus     : MGAGGRMQVSPPSKKKSETDNIKCVPCETPPFTVGELKKAIPPHCFKRSIPRSFSYLIWDIIIASCFYYVATTYFPLLPHPLSY  :  83

*        100         *        120         *        140         *        160
fad2A'LLR1' : FAWPLYWACQGCVLTGVWVIAHECGHHAFSDYQWLDDTVGLIFHSFLLVPYFSWKYSHRRHHSNTGSLERDEVFVPKKKSDIK   : 158
fad2A'HOR1' : FAWPLYWACQGCVLTGVWVIAHECGHHAFSDYQWLDDTVGLIFHSFLLVPYFSWKYSHRRHHSNTGSLERDEVFVPKKKSDIK   : 158
B.rapa      : FAWPLYWACQGCVLTGVWVIAHECGHHAFSDYQWLDDTVGLIFHSFLLVPYFSWKYSHRRHHSNTGSLERDEVFVPKKKSDIK   : 166
B.napus     : FAWPLYWACQGCVLTGVWVIAHECGHHAFSDYQWLDDIVGLIFHSFLLVPYFSWKYSHRRHHSNTGSLERDEVFVPKKKSDIK   : 166

*        180         *        200         *        220         *        240
fad2A'LLR1' : WYGKYLNNPLGRTVMLTVQFTLGWPLYLAFNVSGRPYDGGFACHFHPNAPIYNDRERLQIYISDAGILAVCYGLYRYAAVQGV   : 241
fad2A'HOR1' : WYGKYLNNPLGRTVMLTVQFTLGWPLYLAFNVSGRPYDGGFACHFHPNAPIYNDRERLQIYISDAGILAVCYGLYRYAAVQGV   : 241
B.rapa      : WYGKYLNNPLGRTVMLTVQFTLGWPLYLAFNVSGRPYDGGFACHFHPNAPIYNDRERLQIYISDAGILAVCYGLYRYAAVQGV   : 249
B.napus     : WYGKYLNNPLGRTVMLTVQFTLGWPLYLAFNVSGRPYDGGFACHFHPNAPIYNDRERLQIYISDAGILAVCYGLYRYAAVQGV   : 249

*        260         *        280         *        300         *        320
fad2A'LLR1' : ASMVCFYGVPLLIVNGFLVLITYLQHTHPSLPHYDSSEWDWLRGALATVDRDYGILNKVFHNITDTHVAHHLFSTMPHYHAME   : 324
fad2A'HOR1' : ASMVCFYGVSLLIVNGFLVLITYLQHTHPSLPHYDSSEWDWLRGALATVDRDYGILNKVFHNITDTHVAHHLFSTMPHYHAME   : 324
B.rapa      : WYGCFYGVPLLIVNGFLVLITYLQHTHPSLPHYDSSEWDWLRGALATVDRDYGILNKVFHNITDTHVAHHLFSTMPHYHAME   : 332
B.napus     : ASMVCFYGVPLLIVNGFLVLITYLQHTHPSLPHYDSSEWDWLRGALATVDRDYGILNKVFHNITDTHVAHHLFSTMPHYHAME   : 332

*        340         *        360         *        380
fad2A'LLR1' : ATKAIKPILGEYYQFDGTPVVKAMWREAKECIYVEPDRQGEK---------                                   : 366
fad2A'HOR1' : ATKAIKPILGEYYQFDGTPVVKAMWREAKECIYVEPDRQGEK---------                                   : 366
B.rapa      : ATKVIKPILGEYYQFDGTPVVKAMWREAKECIYVEPDRQGEKKGVFWYNNKL                                  : 384
B.napus     : ATKVIKPILGEYYQFDGTPVVKAMWREAKECIYVEPDRQGEKKGVFWYNNKL                                  : 384
```

Fig. 6

```
                        *        20         *        40         *        60         *        80
fad2C'LLR1' : ------VSPPSKKKSETDTIKRVPCETPPFTVGELKKAIPPHCFKRSIPRSFSYLIWDIIASCFYYVATTYFPLLPHPL :  73
fad2C'HOR1' : ------VSPPSKKKSETDTIKRVPCETPPFTVGELKKAIPPHCFKRSIPRSFSYLIWDIIASCFYYVATTYFPLLPHPL :  73
B.oleracea  : -------------------------------------------------------------------------------- :   -
B.napus     : MGAGGRMQVSPPPSKKKSETDNIKCVPCETPPFTVGELKKAIPPHCFKRSIPRSFSYLIWDIIASCFYYVATTYFPLLPHPL :  81

*       100         *       120         *       140         *       160
fad2C'LLR1' : SYFAWPLYWACQGCVLTGVWVIAHECGHHAFSDYQWLDDTVGLIFHSFLLVPYFSWKYSHRRHHSNTGSLERDEVFVPKKK : 154
fad2C'HOR1' : SYFAWPLYWACQGCVLTGVWVIAHECGHHAFSDYQWLDDTVGLIFHSFLLVPYFSWKYSHRRHHSNTGSLERDEVFVPKKK : 154
B.oleracea  : ---------------------------------------SFLLVPYFSWKYSHRRHHSNTGSLERDEVFVPKKK :  35
B.napus     : SYFAWPLYWACQGCVLTGVWVIAHECGHHAFSDYQWLDDTVGLIFHSFLLVPYFSWKYSHRRHHSNTGSLERDEVFVPKKK : 162

*       180         *       200         *       220         *       240
fad2C'LLR1' : SDIKWYGKYLNNPLGRTVMLTVQFTLGWPLYLAFNVSGRPYDGGFACHFHPNAPIYNDRERLQIYISDAGILAVCYGLFRY : 235
fad2C'HOR1' : SDIKWYGKYLNNPLGRTVMLTVQFTLGWPLYLAFNVSGRPYDGGFACHFHPNASIYNDRERLQIYISDAGILAVCYGLFRY : 235
B.oleracea  : SDIKWYGKYLNNPLGRTVMLTVQFTLGWPLYLAFNVSGRPYDGGFACHFHPNAPIYNDRERLQIYISDAGILAVCYGLYRY : 116
B.napus     : SDIKWYGKYLNNPLGRTVMLTVQFTLGWPLYLAFNVSGRPYDGGFACHFHPNAPIYNDRERLQIYISDAGILAVCYGLYRY : 243

*       260         *       280         *       300         *       320
fad2C'LLR1' : AAAQGVASMVCFYGVPLLIVNGFIVLITYLQHTHPSLPHYDSSEWDWLRGALATVDRDYGILNKVFHNITDTHVAHHLFST : 316
fad2C'HOR1' : AAAQGVASMVCFYGVPLLIVNGFIVLITYLQHTHPSLPHYDSSEWDWLRGALATVDRDYGILNKVFHNITDTHVAHHLFST : 316
B.oleracea  : AAAQGVASMVCFYGVPLLIVNGFIVLITYLQHTHPSLPHYDSSEWDWLRGALATVDRDYGILNKVFHNITDTHVAHHLFST : 197
B.napus     : AAVQGVASMVCFYGVPLLIVNGFIVLITYLQHTHPSLPHYDSSEWDWLRGALATVDRDYGILNKVFHNITDTHVAHHLFST : 324

*       340         *       360         *       380
fad2C'LLR1' : MPHYHAMEATKAIKPILGEYYQFDGTPVVKAMWREAKECIYVEPDRQGEK------- : 366
fad2C'HOR1' : MPHYHAMEATKAIKPILGEYYQFDGTPVVKAMWREAKECIYVEPDRQGEK------- : 366
B.oleracea  : MPHYHAMEA----------------------------------------------- : 206
B.napus     : MPHYHAMEATKVIKPILGEYYQFDGTPVVKAMWREAKECIYVEPDRQGEKKKGVFWYNNKL : 384
```

Fig. 7

|  |   |   |
|---|---|---|
| fad2A'LLR1' | : ---------VSPPSKKSETDNIKRVPCETPPFTVGELKKAIPPHCFKRSIPRSFSYLIWDIILASCFYVVATTYFPLLPHPLSY | : 75 |
| fad2A'HOR2' | : ---------VSPPSKKSETDNIKRVPCETPPFTVGELKKAIPPHCFKRSIPRSFSYLIWDIILASCFYVVATTYFPLLPHPLSY | : 75 |
| B.rapa | : MGAGGRMQVSPPSKKSETDNIKRVPCETPPFTVGELKKAIPPHCFKRSIPRSFSYLIWDIILASCFYVVATTYFPLLPHPLSY | : 83 |
| B.napus | : MGAGGRMQVSPPSKKSETDNIKCVPCETPPFTVGELKKAIPPHCFKRSIPRSFSYLIWDIILASCFYVVATTYFPLLPHPLSY | : 83 |
| fad2A'LLR1' | : FAWPLYWACQGCVLTGVWVIAHECGHHAFSDYQWLDDTVGLIFHSFLLVPYIFSWKYSHRRHHSNTGSLERDEVFVPKKKSDIK | : 158 |
| fad2A'HOR2' | : FAWPLYWACQGCVLTGVWVIAHECGHHAFSDYQWLDDTVGLIFHSFLLVPYIFSWKYSHRRHHSNTGSLERDEVFVPKKKSDIK | : 158 |
| B.rapa | : FAWPLYWACQGCVLTGVWVIAHECGHHAFSDYQWLDDTVGLIFHSFLLVPYIFSWKYSHRRHHSNTGSLERDEVFVPKKKSDIK | : 166 |
| B.napus | : FAWPLYWACQGCVLTGVWVIAHECGHHAFSDYQWLDDTVGLIFHSFLLVPYIFSWKYSHRRHHSNTGSLERDEVFVPKKKSDIK | : 166 |
| fad2A'LLR1' | : WYGKYLNNPLGRTVMLTVQFTLGWPLYLAFNVSGRPYDGGFACHFHPNAPIYNDRERLQIYISDAGILAVCYGLYRYAAVQGV | : 241 |
| fad2A'HOR2' | : WYGKYLNNPLGRTVMLTVQFTLGWPLYLAFNVSGRPYDGGFACHFHPNAPIYNDRERLQIYISDAGILAVCYGLYRYAAVQGV | : 241 |
| B.rapa | : WYGKYLNNPLGRTVMLTVQFTLGWPLYLAFNVSGRPYDGGFACHFHPNAPIYNDRERLQIYISDAGILAVCYGLYRYAAVQGV | : 249 |
| B.napus | : WYGKYLNNPLGRTVMLTVQFTLGWPLYLAFNVSGRPYDGGFACHFHPNAPIYNDRERLQIYISDAGILAVCYGLYRYAAVQGV | : 249 |
| fad2A'LLR1' | : ASMVCFYGVPLLIVNGFLVLITYLQHTHPSLPHYDSSEWDWLRGALATVDRDYGILNKVFHNITDTHVAHHLFSTMPHYHAME | : 324 |
| fad2A'HOR2' | : ASMVCFYGVPLLIVNGFLVLITYLQHMHPSLPHYDSSEWDWLRGALATVDRDYGILNKVFHNITDTHVAHHLFSTMPHYHAME | : 324 |
| B.rapa | : ASMVCFYGVPLLIVNGFLVLITYLQHTHPSLPHYDSSEWDWLRGALATVDRDYGILNKVFHNITDTHVAHHLFSTMPHYHAME | : 332 |
| B.napus | : ASMVCFYGVPLLIVNGFLVLITYLQHTHPSLPHYDSSEWDWLRGALATVDRDYGILNKVFHNITDTHVAHHLFSTMPHYHAME | : 332 |
| fad2A'LLR1' | : ATKAIKPILGEYYQFDGTPVVKAMWREAKECIYVEPDRQGEK------------ | : 366 |
| fad2A'HOR2' | : ATKAIKPILGEYYQFDGTPVVKAMWREAKECIYVEPDRQGEK------------ | : 366 |
| B.rapa | : ATKAIKPILGEYYQFDGTPVVKAMWREAKECIYVEPDRQGEKKGVFWYNNKL | : 384 |
| B.napus | : ATKVIKPILGEYYQFDGTPVVKAMWREAKECIYVEPDRQGEKKGVFWYNNKL | : 384 |

Fig. 8

```
fad2A'LLR1' : -------VSPPSKKSETDNIKRVPCETPPFTVGELKKAIPPHCFKRSIPRSFSYLIWDIIIASCFYYVATTYFPLLPHPL :  73
fad2A'HOR3' : -------VSPPSKKSETDNIKRVPCETPPFTVGELKKAIPPHCFKRSIPRSFSYLIWDIIIASCFYYVATTYFPLLPHPL :  73
B.rapa      : MGAGGRMQVSPPSKKSETDNIKRVPCETPPFTVGELKKAIPPHCFKRSIPRSFSYLIWDIIIASCFYYVATTYFPLLPHPL :  81
B.napus     : MGAGGRMQVSPPSKKSETDNIKCVPCETPPFTVGELKKAIPPHCFKRSIPRSFSYLIWDIIIASCFYYVATTYFPLLPHPL :  81 fad2A'LLR1' : SYFAWPLYWACQGCVLTGVWVIAHECGHHAFSDYQWLDDTVGLIFHSFLLVPYFSWKYSHRRHHSNTGSLERDEVFVPKKK : 154
fad2A'HOR3' : SYFAWPLYWACQGCVLTGVWVIAHECGHHAFSDY-WLDDTVGLIFHSFLLVPYFSWKYSHRRHHSNTGSLERDEVFVPKKK : 153
B.rapa      : SYFAWPLYWACQGCVLTGVWVIAHECGHHAFSDYQWLDDTVGLIFHSFLLVPYFSWKYSHRRHHSNTGSLERDEVFVPKKK : 162
B.napus     : SYFAWPLYWACQGCVLTGVWVIAHECGHHAFSDYQWLDDTVGLIFHSFLLVPYFSWKYSHRRHHSNTGSLERDEVFVPKKK : 162 fad2A'LLR1' : SDIKWYGKYLNNPLGRTVMLTVQFTLGWPLYLAFNVSGRPYDGGFACHFHPNAPIYNDRERLQIYISDAGILAVCYGLYRY : 235
fad2A'HOR3' : SDIKWYGKYLNNPLGRTVMLTVQFTLGWPLYLAFNVSGRPYDGGFACHFHPNAPIYNDRERLQIYISDAGILAVCYGLYRY : 234
B.rapa      : SDIKWYGKYLNNPLGRTVMLTVQFTLGWPLYLAFNVSGRPYDGGFACHFHPNAPIYNDRERLQIYISDAGILAVCYGLYRY : 243
B.napus     : SDIKWYGKYLNNPLGRTVMLTVQFTLGWPLYLAFNVSGRPYDGGFACHFHPNAPIYNDRERLQIYISDAGILAVCYGLYRY : 243 fad2A'LLR1' : AAVQGVASMVCFYGVPLLIVNGFLVLITYLQHTHPSLPHYDSSEWDWLRGALATVDRDYGILNKVFHNITDTHVAHHLFST : 316
fad2A'HOR3' : AAVQGVASMVCFYGVPLLIVNGFLVLITYLQHTHPSLPHYDSSEWDWLRGALATVDRDYGILNKVFHNITDTHVAHHLFST : 315
B.rapa      : AAVQGVASMVCFYGVPLLIVNGFLVLITYLQHTHPSLPHYDSSEWDWLRGALATVDRDYGILNKVFHNITDTHVAHHLFST : 324
B.napus     : AAVQGVASMVCFYGVPLLIVNGFLVLITYLQHTHPSLPHYDSSEWDWLRGALATVDRDYGILNKVFHNITDTHVAHHLFST : 324 fad2A'LLR1' : MPHYHAMEATKAIKPILGEYYQFDGTPVVKAMWREAKECIYVEPDRQGEK------ : 366
fad2A'HOR3' : MPHYHAMEATKAIKPILGEYYQFDGTPVVKAMWREAKECIYVEPDRQGEK------ : 365
B.rapa      : MPHYHAMEATKAIKPILGEYYQFDGTPVVKAMWREAKECIYVEPDRQGEKKGVFWYNNKL : 384
B.napus     : MPHYHAMEATKVIKPILGEYYQFDGTPVVKAMWREAKECIYVEPDRQGEKKGVFWYNNKL : 384
```

Fig. 9

```
                  *        20         *        40         *        60         *        80
fad2A'LLR1' : --------VSPPSKKSETDNIKRVPCETPPFTVGELKKAIPPHCFKRSIPRSFSYLIWDIIIASCFYVATTYFPLLPHPL :  73
fad2A'HOR4' : --------VSPPSKKSETDNIKRVPCETPPFTVGELKKAIPPHCFKRSIPRSFSYLIWDIIIASCFYVATTYFPLLPHPL :  73
B.rapa      : MGAGGRMQVSPPSKKSETDNIKRVPCETPPFTVGELKKAIPPHCFKRSIPRSFSYLIWDIIIASCFYVATTYFPLLPHPL :  81
B.napus     : MGAGGRMQVSPPSKKSETDNIKCVPCETPPFTVGELKKAIPPHCFKRSIPRSFSYLIWDIIIASCFYVATTYFPLLPHPL :  81

*       100         *       120         *       140         *       160
fad2A'LLR1' : SYFAWPLYWACQGCVLTGVWVIAHECGHHAFSDYQWLDDTVGLIFHSFLLVPYFSWKYSHRRHHSNTGSLERDEVFVPKKK : 154
fad2A'HOR4' : SYFAWPLY-ACQGCVLTGVWVIAHECGHHAFSDYQWLDDTVGLIFHSFLLVPYFSWKYSHRRHHSNTGSLERDEVFVPKKK : 153
B.rapa      : SYFAWPLYWACQGCVLTGVWVIAHECGHHAFSDYQWLDDTVGLIFHSFLLVPYFSWKYSHRRHHSNTGSLERDEVFVPKKK : 162
B.napus     : SYFAWPLYWACQGCVLTGVWVIAHECGHHAFSDYQWLDDTVGLIFHSFLLVPYFSWKYSHRRHHSNTGSLERDEVFVPKKK : 162

*       180         *       200         *       220         *       240
fad2A'LLR1' : SDIKWYGKYLNNPLGRTVMLTVQFTLGWPLYLAFNVSGRPYDGGFACHFHPNAPIYNDRERLQIYISDAGILAVCYGLYRY : 235
fad2A'HOR4' : SDIKWYGKYLNNPLGRTVMLTVQFTLGWPLYLAFNVSGRPYDGGFACHFHPNAPIYNDRERLQIYISDAGILAVCYGLYRY : 234
B.rapa      : SDIKWYGKYLNNPLGRTVMLTVQFTLGWPLYLAFNVSGRPYDGGFACHFHPNAPIYNDRERLQIYISDAGILAVCYGLYRY : 243
B.napus     : SDIKWYGKYLNNPLGRTVMLTVQFTLGWPLYLAFNVSGRPYDGGFACHFHPNAPIYNDRERLQIYISDAGILAVCYGLYRY : 243

*       260         *       280         *       300         *       320
fad2A'LLR1' : AAVQGVASMVCFYGVPLLIVNGFLVLITYLQHTHPSLPHYDSSEWDWLRGALATVDRDYGILNKVFHNITDTHVAHHLFST : 316
fad2A'HOR4' : AAVQGVASMVCFYGVPLLIVNGFLVLITYLQHTHPSLPHYDSSEWDWLRGALATVDRDYGILNKVFHNITDTHVAHHLFST : 315
B.rapa      : AAVQGVASMVCFYGVPLLIVNGFLVLITYLQHTHPSLPHYDSSEWDWLRGALATVDRDYGILNKVFHNITDTHVAHHLFST : 324
B.napus     : AAVQGVASMVCFYGVPLLIVNGFLVLITYLQHTHPSLPHYDSSEWDWLRGALATVDRDYGILNKVFHNITDTHVAHHLFST : 324

*       340         *       360         *       380
fad2A'LLR1' : MPHYHAMEATKAIKPILGEYYQFDGTPVVKAMWREAKECIYVEPDRQGEK-------- : 366
fad2A'HOR4' : MPHYHAMEATKAIKPILGEYYQFDGTPVVKAMWREAKECIYVEPDRQGEK-------- : 365
B.rapa      : MPHYHAMEATKAIKPILGEYYQFDGTPVVKAMWREAKECIYVEPDRQGEKKGVFWYNNKL : 384
B.napus     : MPHYHAMEATKVIKPILGEYYQFDGTPVVKAMWREAKECIYVEPDRQGEKKGVFWYNNKL : 384
```

Fig. 10

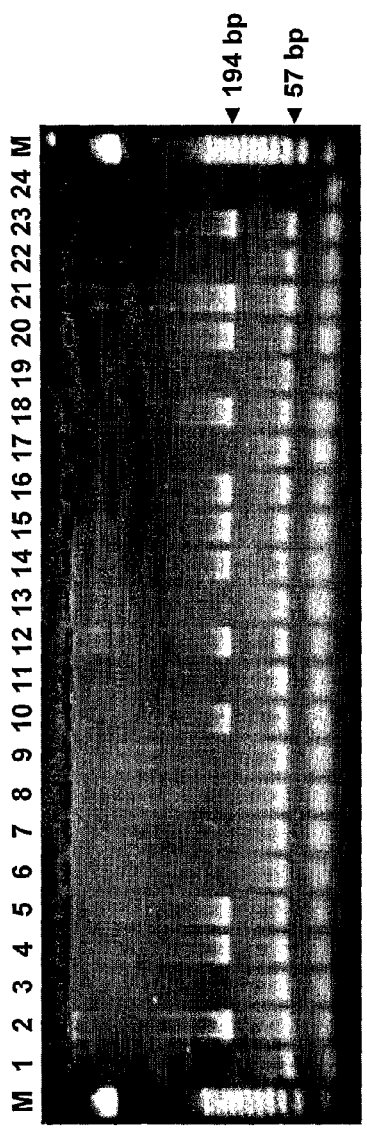

BRASSICA NAPUS PLANTS COMPRISING MUTATED FAD2 ALLELES

CROSS-REFERENCE TO RELATED APPLICATIONS

This application is a national stage entry of International Application Serial No. PCT/IB2007/001384, filed May. 25, 2007, which claims the benefit of European Application Ser. No. 06290855.3 filed May. 29, 2006.

The present invention relates to new genetic and protein markers useful for selecting plants having a high oleic acid content.

High oleic acid content of vegetable oils is a desirable trait both because of the health benefits and of the stability to oxidation and heat of oleic acid. In particular, it has been shown that oleic acid is effective in lowering plasma cholesterol levels (Bonanome et al., 1988; Liu et al., 2002). Furthermore, its single insaturated bond makes oleic acid (C18:1) a much less vulnerable fatty acid than its multiply insaturated counterparts. For instance, the rate of oxidation of linolenic acid (C18:3) is 100 times that of oleic acid (Debruyne, 2004).

One of the most promising paths towards such plants is to select plants essentially deprived of FAD2 activity. Indeed, FAD2 (delta12 oleate desaturase) catalyses the transformation of oleic acid (C18:1) to linoleic acid (C18:2); plants having lowered FAD2 activity thus enjoy higher oleic acid content thanks to limited catabolism of the latter.

As such, WO 2004/072259 provides a *Brassica napus* plant having high oleic acid content, wherein its fad2 gene presents a STOP codon instead of a Glutamine (Q) codon at position 185 of FAD2.

Furthermore, US 2005/0039233 provides a *Brassica juncea* plant having high oleic acid content, wherein its fad2 gene presents a STOP codon instead of a Tryptophan (W) codon at position 101 of FAD2.

*Brassica napus* (rapeseed) is an amphidiploid which contains the genomes of two diploid ancestors, *Brassica rapa* (the A genome) and *Brassica oleracea* (the C genome) (Pires et al., 2004). The oleic acid content is 61% for the traditional oil of rapeseed (Stan Skrypetz, 2005).

The present invention notably arises from the finding, by the Inventors, of five previously unrecognised mutations in the fad2 genes of *Brassica napus* plants:

G to A substitution at position 269 of the fad2A gene (fad2 gene from *B. rapa* genome), corresponding to a W to STOP codon substitution at position 90 of the FAD2A protein, C to T substitution at position 346 of the fad2A gene (fad2 gene from *B. rapa* genome), corresponding to a Q to STOP codon substitution at position 116 of the FAD2A protein, C to T substitution at position 646 of the fad2C gene (fad2 gene from *B. oleracea* genome), corresponding to a P to S substitution at position 216 of the FAD2C protein, C to T substitution at position 775 of the fad2A gene (fad2 gene from *B. rapa* genome), corresponding to a P to S substitution at position 259 of the FAD2A protein, C to T substitution at position 827 of the fad2A gene (fad2 gene from *B. rapa* genome), corresponding to a T to M substitution at position 276 of the FAD2A protein, which correlate with high oleic acid content of plants harbouring them. In particular, the oleic acid content of these mutated rapeseeds varies from 66% to 82% according to environmental culture conditions.

Thus, the present invention relates to a mutated nucleic acid sequence of a delta-12 oleate desaturase enzyme (FAD2)-encoding nucleic acid from a plant, in particular a Cruciferae plant, wherein said mutated nucleic acid sequence comprises the non-conservative mutation of at least one nucleotide of at least one codon representing an amino acid selected from the group consisting of:

the amino acid at position 90 of the amino acid sequence of said FAD2, the amino acid at position 116 of the amino acid sequence of said FAD2, the amino acid at position 216 of the amino acid sequence of said FAD2 when said FAD2 sequence is constituted of 384 amino acids, or at position 215 when said FAD2 sequence is constituted of 383 amino acids, the amino acid at position 259 of the amino acid sequence of said FAD2 when said FAD2 sequence is constituted of 384 amino acids, or at position 258 when said FAD2 sequence is constituted of 383 amino acids, the amino acid at position 276 of the amino acid sequence of said FAD2 when said FAD2 sequence is constituted of 384 amino acids, or at position 275 when said FAD2 sequence is constituted of 383 amino acids, or a homologous nucleic acid sequence derived from said mutated nucleic acid sequence by substitution, insertion, or deletion of at least one nucleotide, and presenting at least 90% homology with said mutated nucleic acid sequence, provided that said homologous nucleic acid sequence presents said mutation and does not encode a functional FAD2, or a hybridizing nucleic acid sequence which hybridizes under stringent conditions to said mutated nucleic acid sequence, provided that the complementary sequence of said hybridizing nucleic acid sequence presents said mutation and does not encode a functional FAD2, or the complementary sequences of said mutated, homologous, or hybridizing nucleic acid sequences.

The homology percentage of a given nucleic acid sequence with respect to the mutated nucleic acid sequence is calculated by counting the number of identical nucleotides between said given nucleic acid sequence and the mutated nucleic acid sequence for all positions of an optimal sequence alignment of said given nucleic acid sequence and the mutated nucleic acid sequence and by dividing this number by the total number of nucleotides of said given sequence.

The optimal sequence alignment can be produced manually, optionally by introducing gaps between nucleotides, or by using computer-based alignment tools, such as BLAST (Altschul et al. (1997) *Nucleic Acids Res* 25: 3389-402).

"Stringent conditions" for a given nucleic acid sequence can be easily determined by the man skilled in the art, for instance as described in Sambrook et al. (2001). Particular stringent conditions notably encompass 15 mM NaCl/1.5 mM sodium citrate (0.1×SSC) and 0.1% sodium lauryl sulphate (SDS) at 50-65° C.

As intended herein, FAD2 from Cruciferae are usually constituted of 383 or 384 amino acids. However, it is within the ordinary skills of the man skilled in the art to adapt the positions given for the above defined mutations to FAD2 having more or less than 383 or 384 amino acids.

An exemplary alignment of FAD2 sequences from various Cruciferae species is given in FIG. 14.

As intended herein, a nucleic acid sequence which "does not encode a functional FAD2" relates to a nucleic acid sequence which encodes a FAD2 having an activity lower than that of the corresponding natural FAD2 measured in the same conditions, in particular the encoded FAD2 has no activity.

Advantageously, mutant plants carrying nucleic acids with the above-defined mutations have an increased oleic acid content as compared to otherwise genetically identical plants (i.e. plants which are genetically identical except for said mutations) and to the corresponding wild-type plants. Preferably, mutant plants carrying nucleic acids with the above-defined mutations have an oleic acid content of at least 65%, more preferably of at least 70%.

In an embodiment, the invention particularly relates to a mutated nucleic acid sequence as defined above, wherein said mutated nucleic acid sequence comprises at least one mutation selected from:
  a substitution of the codon representing the amino acid at position 90 of the amino acid sequence of said FAD2 by a STOP codon,
  a substitution of the codon representing the amino acid at position 116 of the amino acid sequence of said FAD2 by a STOP codon,
  a substitution of the codon representing the amino acid at position 216 of the amino acid sequence of said FAD2 when said FAD2 sequence is constituted of 384 amino acids, or at position 215 when said FAD2 sequence is constituted of 383 amino acids, by a codon representing any amino acid different from P,
  a substitution of the codon representing the amino acid at position 259 of the amino acid sequence of said FAD2 when said FAD2 sequence is constituted of 384 amino acids, or at position 258 when said FAD2 sequence is constituted of 383 amino acids, by a codon representing any amino acid different from P,
  a substitution of the codon representing the amino acid at position 276 of the amino acid sequence of said FAD2 when said FAD2 sequence is constituted of 384 amino acids, or at position 275 when said FAD2 sequence is constituted of 383 amino acids, by any amino acid different from T.

In another embodiment, the invention more particularly relates to a mutated nucleic acid sequence as defined above, wherein:
  the codon representing the amino acid at position 216 of the amino acid sequence of said FAD2 when said FAD2 sequence is constituted of 384 amino acids, or at position 215 when said FAD2 sequence is constituted of 383 amino acids, is substituted by a codon representing S,
  the codon representing the amino acid at position 259 of the amino acid sequence of said FAD2 when said FAD2 sequence is constituted of 384 amino acids, or at position 258 when said FAD2 sequence is constituted of 383 amino acids, is substituted by a codon representing S,
  the codon representing the amino acid at position 276 of the amino acid sequence of said FAD2 when said FAD2 sequence is constituted of 384 amino acids, or at position 275 when said FAD2 sequence is constituted of 383 amino acids, is substituted by a codon representing M.

In a preferred embodiment of the above defined mutated nucleic acid sequence, the plant is of the *Brassica* genus.

In another preferred embodiment of the invention, the mutated nucleic acid sequence is represented by SEQ ID NO: 22 and comprises at least one mutation selected from the group constituted of:
  G to A substitution at position 269 of SEQ ID NO: 22,
  C to T substitution at position 346 of SEQ ID NO: 22,
  C to T substitution at position 646 of SEQ ID NO: 22,
  C to T substitution at position 775 of SEQ ID NO: 22,
  C to T substitution at position 827 of SEQ ID NO: 22, In yet another embodiment of the invention, the mutated nucleic acid sequence is selected from the group constituted of:
  SEQ ID NO: 24;
  SEQ ID NO: 26;
  SEQ ID NO: 28;
  SEQ ID NO: 30;
  SEQ ID NO: 32.

SEQ ID NO: 24 represents the fad2A gene of *B. napus* (i.e. the fad2 gene from *B. rapa* genome) harboring a G to A substitution at position 269, which corresponds to a W to STOP codon substitution at position 90 of the FAD2A protein. This mutation is in particular found in the oleic acid overproducing rapeseed line denoted 'HOR4' in the following Example. 'HOR4' has been deposited at the NCIMB (Aberdeen, Scotland) on May 17, 2006 under accession number 41403.

SEQ ID NO: 26 represents the fad2A gene of *B. napus* harboring a C to T substitution at position 346, which corresponds to a Q to STOP codon substitution at position 116 of the FAD2A protein. This mutation is in particular found in the oleic acid overproducing rapeseed line denoted 'HOR3' in the following Example. 'HOR3' has been deposited at the NCIMB (Aberdeen, Scotland) on May 17, 2006 under accession number 41402.

SEQ ID NO: 28 represents the fad2C gene of *B. napus* (i.e. the fad2 gene from *B. oleracea* genome) harboring a C to T substitution at position 646, which corresponds to a P to S substitution at position 216 of the FAD2C protein. This mutation is in particular found in the oleic acid overproducing rapeseed line denoted 'HOR1' in the following Example. 'HOR1' has been deposited at the NCIMB (Aberdeen, Scotland) on May 17, 2006 under accession number 41400.

SEQ ID NO: 30 represents the fad2A gene of *B. napus* harboring a C to T substitution at position 775, which corresponds to a P to S substitution at position 259 of the FAD2A protein. This mutation is in particular found in the oleic acid overproducing rapeseed line denoted 'HOR1' in the following Example.

SEQ ID NO: 32 represents the fad2A gene of *B. napus* harboring a C to T substitution at position 827, which corresponds to a T to M substitution at position 276 of the FAD2A protein. This mutation is in particular found in the oleic acid overproducing rapeseed line denoted 'HOR2' in the following Example. 'HOR2' has been deposited at the NCIMB (Aberdeen, Scotland) on May 17, 2006 under accession number 41401.

The present invention also relates to a nucleic acid fragment of a mutated nucleic acid as defined above, said fragment comprising at least 10, preferably at least 100, more preferably at least 1000 nucleotides, and comprising at least one nucleotide contiguous to at least one codon representing an amino acid selected from the group consisting of:
  the amino acid at position 90 of the amino acid sequence of said FAD2,
  the amino acid at position 116 of the amino acid sequence of said FAD2,
  the amino acid at position 216 of the amino acid sequence of said FAD2 when said FAD2 sequence is constituted of 384 amino acids, or at position 215 when said FAD2 sequence is constituted of 383 amino acids,
  the amino acid at position 259 of the amino acid sequence of said FAD2 when said FAD2 sequence is constituted of 384 amino acids, or at position 258 when said FAD2 sequence is constituted of 383 amino acids, the amino acid at position 276 of the amino acid sequence of said FAD2 when said FAD2 sequence is constituted of 384 amino acids, or at position 275 when said FAD2 sequence is constituted of 383 amino acids, or the complementary sequence of said nucleic acid fragment.

In a preferred embodiment of the invention, the above-defined nucleic acid fragment comprises the mutated nucleotide.

In another preferred embodiment of the invention, the above-defined nucleic acid fragment is selected from the group constituted of SEQ ID NO: 12, SEQ ID NO: 14, SEQ ID NO: 17, SEQ ID NO: 34 and SEQ ID NO: 35, SEQ ID NO: 3, SEQ ID NO: 4, SEQ ID NO: 5, SEQ ID NO: 6 and SEQ ID NO: 7.

The present invention also relates to a plant, preferably a Cruciferae plant, more preferably a plant of the *Brassica* genus, and even more preferably a plant of the *Brassica napus* species, having an increased oleic acid content, or a part of said plant, wherein the plant comprises at least one mutated nucleic acid sequence as defined above or a nucleic acid fragment as defined above which comprises the mutated nucleotide.

As intended herein, a part of plant notably relates to a plant cell, a seed, a meristem, a cal, an inflorescence, a bud, or a leaf.

In a particular embodiment of the above-defined plant, or part of plant, at least one copy of the fad2 gene which is comprised in the genome of said plant is represented by a mutated nucleic acid as defined above.

In another particular embodiment of the above-defined plant, or part of plant, each copy of the fad2 gene which is comprised in the genome of said plant is represented by a mutated nucleic acid as defined above.

Another embodiment of the invention, relates to the above-defined plant, or part of plant, wherein:
one copy of the fad2A gene is represented by SEQ ID NO: 30 and one copy of the fad2C gene is represented by SEQ ID NO: 28, or
one copy of the fad2A gene is represented by SEQ ID NO: 32, or
one copy of the fad2A gene is represented by SEQ ID NO: 26, or
one copy of the fad2A gene is represented by SEQ ID NO: 24.

In a further embodiment of the invention, the above-defined plant, or part of plant, is a plant of the *Brassica napus* species wherein both copies of the fad2A gene are independently represented by SEQ ID NO: 24, SEQ ID NO: 26, SEQ ID NO: 30 or SEQ ID NO: 32, and/or both copies of the fad2C gene are represented by SEQ ID NO: 28.

In yet another particular embodiment, the above-defined plant, or part of plant, is selected from the group constituted of:
the plant deposited at the NCIMB (Aberdeen, Scotland) on May 17, 2006 under accession number 41403;
the plant deposited at the NCIMB (Aberdeen, Scotland) on May 17, 2006 under accession number 41402;
the plant deposited at the NCIMB (Aberdeen, Scotland) on May 17, 2006 under accession number 41400;
the plant deposited at the NCIMB (Aberdeen, Scotland) on May 17, 2006 under accession number 41401.

The present invention also relates to the use of a nucleic acid as defined above for selecting plants, or part of plants, having an increased oleic acid content.

The present invention also relates to a method for selecting plants having an increased oleic acid content by mutagenesis, comprising the following steps:

subjecting a plant or part of a plant to a mutagenic treatment,
regenerating plants, or part of plants, from said treated plant or part of a plant,
selecting from the regenerated plants those comprising at least one mutated nucleic acid sequence as defined above or a nucleic acid fragment as defined above which comprises the mutated nucleotide.

Mutagenesis can be carried out according to methods well known to the man skilled in the art, such as those described in McCallum et al. (2000). In particular, mutagenesis is carried out using ethyl methanesulphonate (EMS).

The regeneration of plants from plant parts, such as cells, can be carried out according to methods well known to the man skilled in the art, such as those described in Herman (2005).

The present invention also relates to a method for selecting plants having an increased oleic acid content by crossing, comprising the following steps:
crossing a plant, or part of a plant, with a parent plant, or part of a parent plant, comprising at least one mutated nucleic acid sequence as defined above or a nucleic acid fragment as defined above which comprises the mutated nucleotide,
selecting from the progeny plants, or, part of plants, obtained by crossing, those comprising at least one mutated nucleic acid sequence as defined above or a nucleic acid fragment as defined above which comprises the mutated nucleotide.

Crossing can be carried out according to methods well known to the man skilled in the art, such as those described in Gallais (1997).

As intended herein "progeny" in particular relates to the seedlings of the crossed plants.

In a preferred embodiment of the above-defined method for selecting plants having an increased oleic acid content by crossing, the parent plant is obtained according to the above-defined method for selecting plants having an increased oleic acid content by mutagenesis.

In a particularly preferred embodiment of the above-defined method for selecting plants having an increased oleic acid content by crossing, the parent plant, or part of the parent plant, is selected from the group constituted of:
the plant deposited at the NCIMB (Aberdeen, Scotland) on May 17, 2006 under accession number 41403;
the plant deposited at the NCIMB (Aberdeen, Scotland) on May 17, 2006 under accession number 41402;
the plant deposited at the NCIMB (Aberdeen, Scotland) on May 17, 2006 under accession number 41400;
the plant deposited at the NCIMB (Aberdeen, Scotland) on May 17, 2006 under accession number 41401.

In particular, the following techniques can be used in the selection step of the above-defined selection methods: PCR techniques, such as the TaqMan® assay (real-time PCR) or allele-specific PCR, Northern or Southern blotting, DNA micro or macro-array, Molecular Beacons, DASH (Dynamic Allele Specific Hybridization), primer extension, oligonucleotide ligation and endonuclease cleavage.

In an embodiment of the above defined methods for selecting plants, the selection step is carried by polymerase chain reaction (PCR), preferably with at least one of the following primer pairs:
SEQ ID NO: 12 and SEQ ID NO: 13,
SEQ ID NO: 14 and SEQ ID NO: 15,
SEQ ID NO: 16 and SEQ ID NO: 17,
SEQ ID NO: 34 and SEQ ID NO: 36,
SEQ ID NO: 35 and SEQ ID NO: 36, SEQ ID NO: 37 and SEQ ID NO: 13,
SEQ ID NO: 38 and SEQ ID NO: 14,
SEQ ID NO: 39 and SEQ ID NO: 36.

The present invention also relates to a plant as obtainable according to the above-defined methods for selecting plants.

The present invention also relates to a kit for the selection of plants having a high oleic acid content, comprising:
- at least one plant, or part of plant, comprising at least one mutated nucleic acid sequence as defined above or a nucleic acid fragment as defined above which comprises the mutated nucleotide,
- at least one nucleic acid fragment as defined above.

In a preferred embodiment of the invention, the above-defined kit comprises:
- at least one plant, or part of plant, selected from the group constituted of
  - the plant deposited at the NCIMB (Aberdeen, Scotland) on May 17, 2006 under accession number 41403;
  - the plant deposited at the NCIMB (Aberdeen, Scotland) on May 17, 2006 under accession number 41402;
  - the plant deposited at the NCIMB (Aberdeen, Scotland) on May 17, 2006 under accession number 41400;
  - the plant deposited at the NCIMB (Aberdeen, Scotland) on May 17, 2006 under accession number 41401;
- at least one of the following primer pairs:
  - SEQ ID NO: 12 and SEQ ID NO: 13,
  - SEQ ID NO: 14 and SEQ ID NO: 15,
  - SEQ ID NO: 16 and SEQ ID NO: 17.
  - SEQ ID NO: 34 and SEQ ID NO: 36,
  - SEQ ID NO: 35 and SEQ ID NO: 36,
  - SEQ ID NO: 37 and SEQ ID NO: 13,
  - SEQ ID NO: 38 and SEQ ID NO: 14,
  - SEQ ID NO: 39 and SEQ ID NO: 36.

The present invention also relates to a mutated FAD2 from plant encoded by a mutated nucleic acid sequence as defined above.

The present invention also relate to a nucleic acid selected from the group constituted of SEQ ID NO: 13, SEQ ID NO: 15, SEQ ID NO: 16, SEQ ID NO: 36, SEQ ID NO: 37, SEQ ID NO: 38, SEQ ID NO: 39.

The present invention also relates to a specific antibody to a mutated delta-12 oleate desaturase enzyme (FAD2) from plant as defined above.

As intended herein, "antibody" also encompasses antibody fragments such as Fab, F(ab)'$_2$, or scFv fragments. Such an antibody can be readily prepared by the man skilled in the art from mutated delta-12 oleate desaturase enzymes according to the invention by following standard procedures. In a preferred embodiment of the invention the antibody is a monoclonal antibody. Antibodies according to the invention are notably useful for detecting mutated delta-12 oleate desaturase enzymes according to the invention, in particular in plant cellular extracts.

BRIEF DESCRIPTION OF THE DRAWINGS

FIGS. 1a and 1b show partial genomic nucleotide sequences of the fad2A gene (fad2 gene from *B. rapa* genome) cloned from 'LLR1' lines (both LLR1#S007' and 'LLR1#PR-2601' lines) and 'HOR1' lines (both 'HOR1#S005', 'HOR1#B005' and 'HOR1#NPZ-12' lines). The top is 'LLR1' sequence (SEQ ID NO: 1) and bottom is 'HOR1' sequence (SEQ ID NO: 3). Arrowhead indicates a single nucleotide mutation of C to T, which results in an amino acid modification. The forward and reverse primers for PCR-based mutant allele-specific marker are bolded and underlined.

FIGS. 2a and 2b show partial genomic nucleotide sequences of the fad2C gene (fad2 gene from *B. oleracea* genome) cloned from 'LLR1' lines (both LLR1#S007'and 'LLR1#PR-2601' lines) and 'HOR1' lines (both 'HOR1#S005', 'HOR1#B005' and 'HOR1#NPZ-12' lines). The top is 'LLR1' sequence (SEQ ID NO: 2) and bottom is 'HOR1' sequence (SEQ ID NO: 4). Arrowhead indicates a single nucleotide mutation of C to T, which results in an amino acid modification. The forward and reverse primers for PCR-based mutant allele-specific marker are bolded and underlined.

FIGS. 3a and 3b show partial genomic nucleotide sequences of the fad2A gene (fad2 gene from *B. rapa* genome) cloned from 'LLR1' lines (both LLR1#S007' and 'LLR1#PR-2601' lines) and 'HOR2' lines. The top is 'LLR1' sequence (SEQ ID NO: 1) and bottom is 'HOR2' sequence (SEQ ID NO: 5). Arrowhead indicates a single nucleotide mutation of C to T, which results in an amino acid modification. The forward and reverse primers for PCR-based mutant allele-specific marker are bolded and underlined.

FIG. 4a and 4b show partial genomic nucleotide sequences of the fad2A gene (fad2 gene from *B. rapa* genome) cloned from 'LLR1' lines (both LLR1#S007' and 'LLR1#PR-2601' lines) and 'HOR3' lines. The top is 'LLR1' sequence (SEQ ID NO: 1) and bottom is 'HOR3' sequence (SEQ ID NO: 6). Arrowhead indicates a single nucleotide mutation of C to T, which results in a stop codon (TAG) shaded in grey. The forward and reverse primers for PCR-based mutant allele-specific marker are bolded and underlined.

FIGS. 5a and 5b show partial genomic nucleotide sequences of the fad2A gene (fad2 gene from *B. rapa* genome) cloned from 'LLR1' lines (both LLR1#S007'and 'LLR1#PR-2601' lines) and 'HOR4' lines. The top is 'LLR1' sequence (SEQ ID NO: 1) and bottom is 'HOR4' sequence (SEQ ID NO: 7). Arrowhead indicates a single nucleotide mutation of G to A, which results in a stop codon (TAG) shaded in grey. The forward and reverse primers for PCR-based mutant allele-specific marker are bolded and underlined.

FIG. 6 provides amino acid sequences of the fad2A genes, degenerated from the genomic nucleotide sequence cloned from 'LLR1' lines, 'HOR1', a published *B. rapa* fad2 gene and a published *B. napus* fad2 gene. Arrowhead indicates the position of the amino acid substitution (P to S) resulting from a single nucleotide mutation (C to T) in 'HOR1' line.

FIG. 7 provides amino acid sequences of the fad2C genes, degenerated from the genomic nucleotide sequence cloned from 'LLR1' lines, 'HOR1' lines, a published *B. oleracea* fad2 gene and a published *B. napus* fad2 gene. Arrowhead indicates the position of the amino acid substitution (P to S) resulting from a single nucleotide mutation (C to T) in 'HOR1' line.

FIG. 8 provides amino acid sequences of the fad2A genes, degenerated from the genomic nucleotide sequence cloned from 'LLR1' lines, 'HOR2' lines, a published *B. rapa* fad2 gene and a published *B. napus* fad2 gene. Arrowhead indicates the position of the amino acid substitution (T to M) resulting from a single nucleotide mutation (C to T) in 'HOR2' line.

FIG. 9 provides amino acid sequences of the fad2A genes, degenerated from the genomic nucleotide sequence cloned from 'LLR1' lines, 'HOR3' lines, a published *B. rapa* fad2 gene and a published *B. napus* fad2 gene. Arrowhead indicates the position of the stop codon resulting from a single nucleotide mutation (C to T) in 'HOR3' line.

FIG. 10 provides amino acid sequences of the fad2A genes, degenerated from the genomic nucleotide sequence cloned from 'LLR1' lines, 'HOR4' lines, a published *B. rapa* fad2 gene and a published *B. napus* fad2 gene. Arrowhead indicates the position of the stop codon resulting from a single nucleotide mutation (G to A) in 'HOR4' line.

FIG. 11 provides electrophoresis results of PCR products amplified from the mutant allele-specific markers for the fad2A gene (194 bp) and from the fad3 gene (internal PCR control, 57 bp) of one of the 6 DH populations. M, 25 bp DNA ladder; lane 1, 'LLR1#S007'; lane 2, 'HOR1#S005'; lane 3-23, DH lines from the cross of 'LLR1#S007' and 'HOR1#S005'; lane 24: water control. The PCR products were separated by electrophoresis in an 2.5% agarose gel and stained with ethidium bromide.

FIG. 12 provides electrophoresis results of PCR products amplified from the mutant allele-specific markers for the fad2C gene (123 bp) and from the fad3 gene (internal PCR control, 57 bp) of one of the 6 DH populations. M, 25 bp DNA ladder; Lane 1, 'LLR1#S007'; lane 2, 'HOR1#S005'; lane 3-23, DH lines from the cross of 'LLR1#S007'and 'HOR1#S005'; lane 24: water control. The PCR products were separated by electrophoresis in an 2.5% agarose gel and stained with ethidium bromide.

Figure 13:
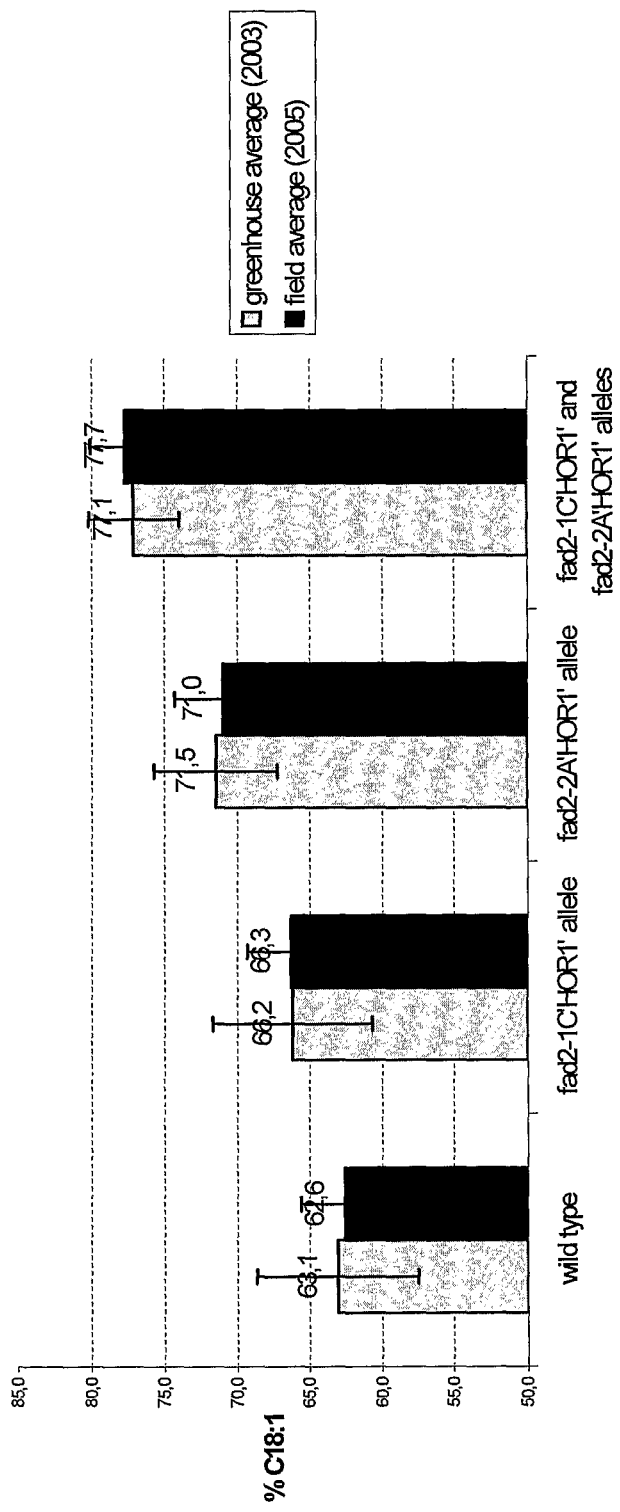
FIG. 13 provides histogram showing the correlation of the mutant allele-specific markers and oleic acid content in field and greenhouse trials.
Figure 14A:
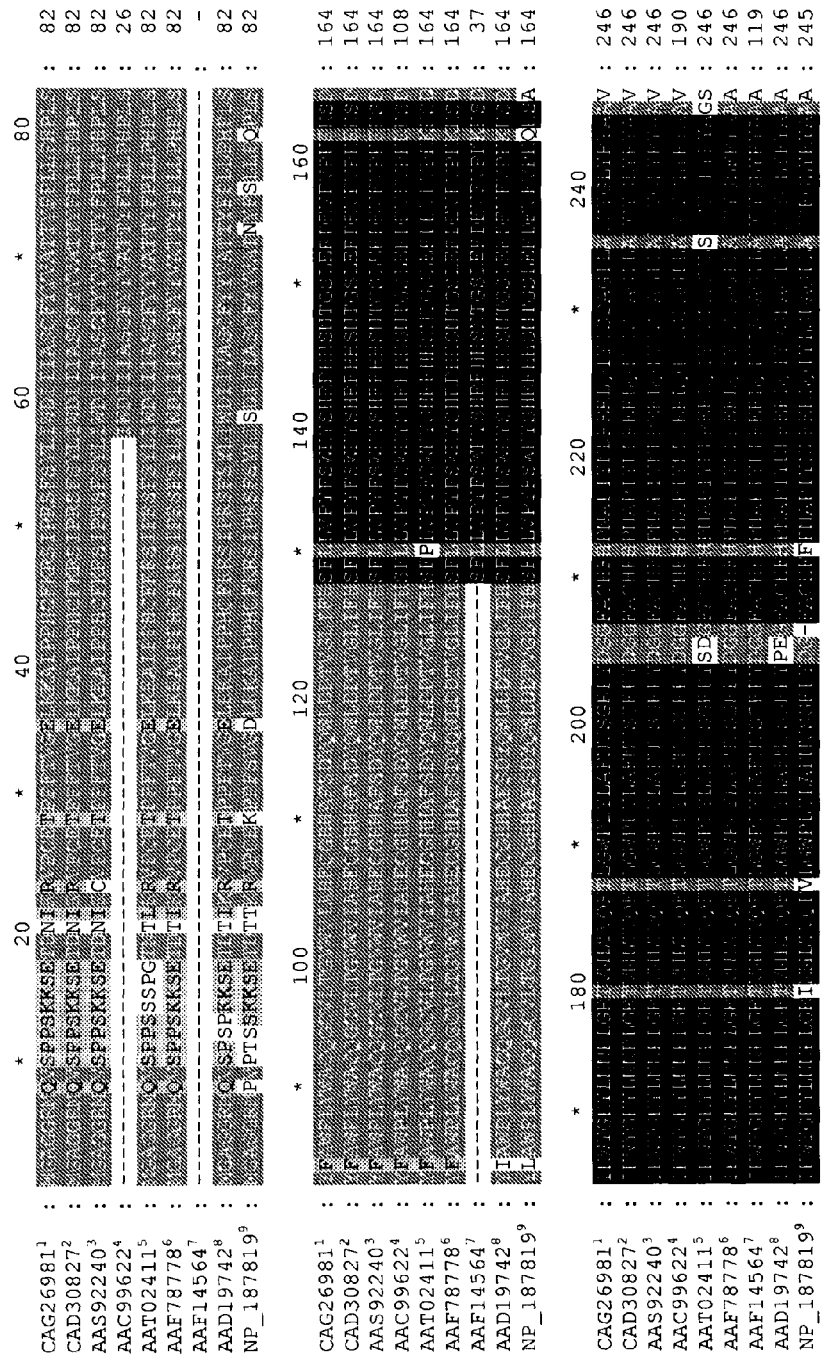
FIGS. 14a and 14b provides a sequence alignment of FAD2 from different *Brassica* species and from *Arabidopsis thaliana*. Species, accession numbers and common names are listed hereafter.
Figure 14B:
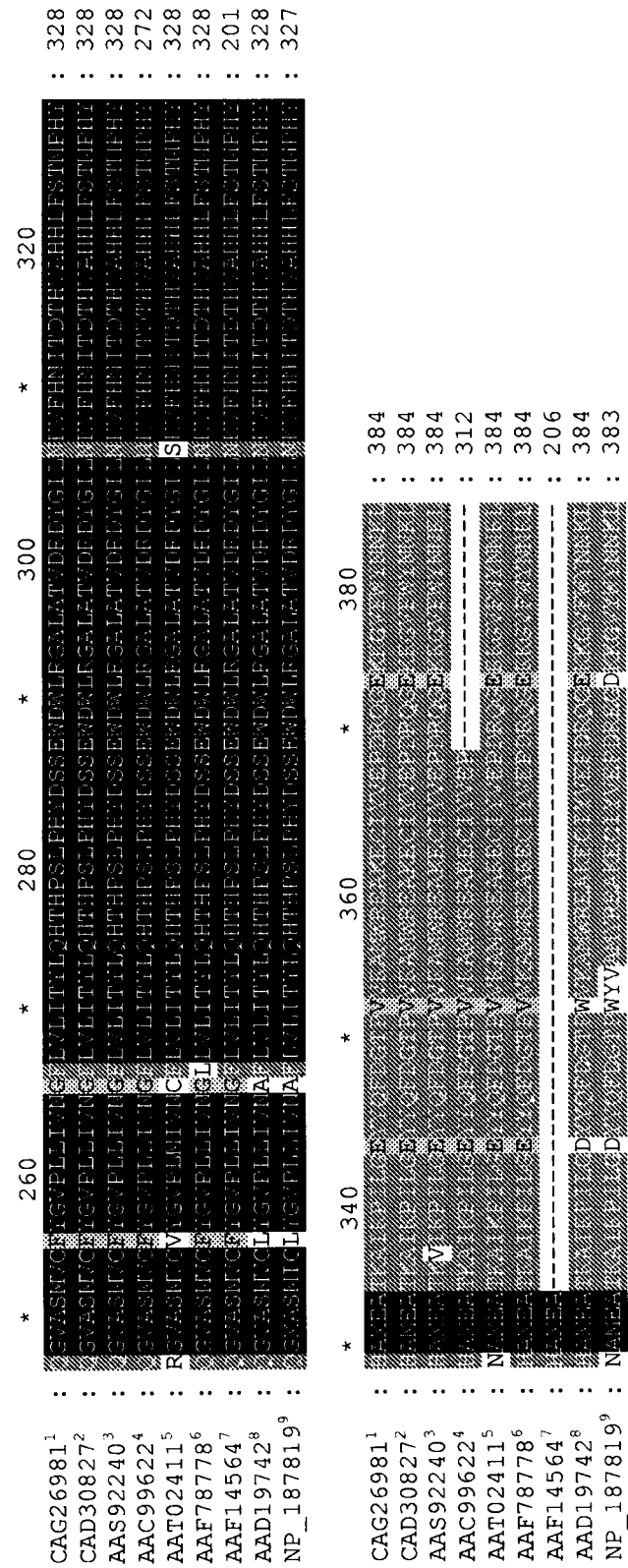

| | Genus and species | Sequence accession number | Common name |
|---|---|---|---|
| 1 | Brassica rapa | CAG26981 | Wild turnip |
| 2 | Brassica rapa | CAD30827 | Wild turnip |
| 3 | Brassica napus | AAS92240 | Rapeseed |
| 4 | Brassica rapa | AAC99622 | Wild turnip |
| 5 | Brassica napus | AAT02411 | Rapeseed |
| 6 | Brassica napus | AAF78778 | Rapeseed |
| 7 | Brassica oleracea | AAF14564 | Cabbage |
| 8 | Brassica carinata | AAD19742 | Ethiopian mustard |
| 9 | Arabidopsis thaliana | NP_187819 | Wall-cress |

EXAMPLE

Material and Methods

1. Plant Material

Winter rapeseed lines 'LLR1#S007' (wild type), 'LLR1#PR-2601' (wild type), 'HOR1#S005' (mutant type), 'HOR1#B005' (mutant type), 'HOR1#NPZ-12' (mutant type), 'HOR2' (mutant type), 'HOR3' (mutant type) and 'HOR4' (mutant type) were used in this study for cloning of fad2 (fatty acid desaturase-2) alleles.

'HOR1#S005', 'HOR1#B005' and 'HOR1#NPZ-12' have been obtained by crossing an ethyl methanesulphonate (EMS) mutant line 'HOR1 ' with three classical rapeseed lines (S005, B005 and NPZ-12); these three mutant lines have an oleic acid content at about 80 to 90%.

'LLR1#S007' and 'LLR1#PR-2601' are rapeseed lines with oleic acid content at about 60%.

'HOR2', 'HOR3' and 'HOR4' are three more independent EMS mutant lines with oleic acid content at about 75 to 85%.

Six double haploid (DH) populations were developed by microspore culture from F1 plants of crosses between (Coventry et al. 1988):

(1) 'LLR1#S007' and 'HOR1#S005' rapeseed lines,
(2) 'LLR1#PR-2601' and 'HOR1#NPZ-12' rapeseed lines,
(3) 'LLR1#S007' and 'HOR1#B005' rapeseed lines,
(4) 'LLR1#S007' and 'HOR1#NPZ-12' rapeseed lines,
(5) 'LLR1#PR-2601' and 'HOR1#B005' rapeseed lines and
(6) 'LLR1#PR-2601' and 'HOR1#S005' rapeseed lines.

Each DH population comprised of 64, 32, 115, 72, 63 and 53 lines respectively. A complete fatty acid analysis of the seeds of the DH lines and their respective parents was implemented by using gas chromatography. All the 399 DH lines were used for marker and statistical analysis. No DH population has been produced with 'HOR2', 'HOR3'and ' HOR4' mutant lines.

2. Genomic DNA Extraction and Quantification

DNA of both parental lines and 399 DH lines was extracted from leaves of 2-week-old field grown plants using a CTAB-based method modified from Dellaporta et al. (1983). Absorbance at 260 nm was used for DNA quantification. In a UV-microtiter plate, 195 µl of ultrapure sterile water were added into each well and then 5 µl of each DNA sample were added. The plate was then briefly agitated and read using the Spectra Max M2 microplate spectrophotometer from Molecular Devices.

3. PCR Amplification

PCR amplification reactions used for fad2 alleles cloning contained 3-4 ng/µl of genomic DNA, 1.25 µM of each primer, 2.5 mM $MgCl_2$, 0.3 mM of each dNTP, 1×PCR buffer and 0.12 U/µl of Taq DNA polymerase. Amplifications were performed in a PTC-225 MJResearch PCR system programmed for 30 cycles of 30 sec at 94° C., 30 sec at 60° C., 30 sec at 72° C. and ending with 5 min at 72° C.

For genotyping the 399 DH, an internal PCR marker has been developed to control the PCR efficiency. A couple of primers (SEQ ID NO: 10 and SEQ ID NO: 11) has been designed on the fad3 gene to amplify a fragment at 57 bp. PCR amplification reactions used for genotyping the 399 DH lines contained 3-4 ng/µl of genomic DNA, 0.625 µM of each primer (SEQ ID NO: 8, SEQ ID NO:9, SEQ ID NO: 10 and SEQ ID NO: 11), 1.5 mM $MgCl_2$, 0.3 mM of each dNTP, 1×PCR buffer and 0.06 U/µl of Taq DNA polymerase. Amplifications were performed in a PTC-225 MJResearch PCR system programmed for 30 cycles of 30 sec at 94° C., 30 sec at 60° C., 10 sec at 72° C. and ending with 5 min at 72° C.

4. Cloning of Fad2 Alleles

The fad2 fragments of parental lines 'LLR1#S007', 'LLR1#PR-2601', 'HOR1S#005', 'HOR1#B005', 'HOR1#NPZ-12', 'HOR2', 'HOR3' and 'HOR4' were amplified by using primers designed with Primer 3 software on fad2 gene sequence from GenBank Accession AY577313. The fad2 fragments amplified from each of the parents by the primers FAD2BnF1 and FAD2BnR1 were ligated to pGEM®-T Easy cloning vector using a PGEM®-T Easy Vector System kit (Promega Corp., Madison, USA) per manufacturer's instructions. The ligated products were transformed into competent cells and the cells plated on LB-agar plates containing ampicillin, X-GAL and IPTG to enable white/blue selection. White colonies in the transformation plates were picked and identification of the cloned PCR products were verified by PCR using universal M13 Forward and Reverse primers flanking the insert fragment. PCR revealed the insert fragment of the expected size. The positive clones containing the insert were sequenced by Genome Express (Meylan, France).

5. Identification of Mutations in fad2 Genes

Figure 5A:
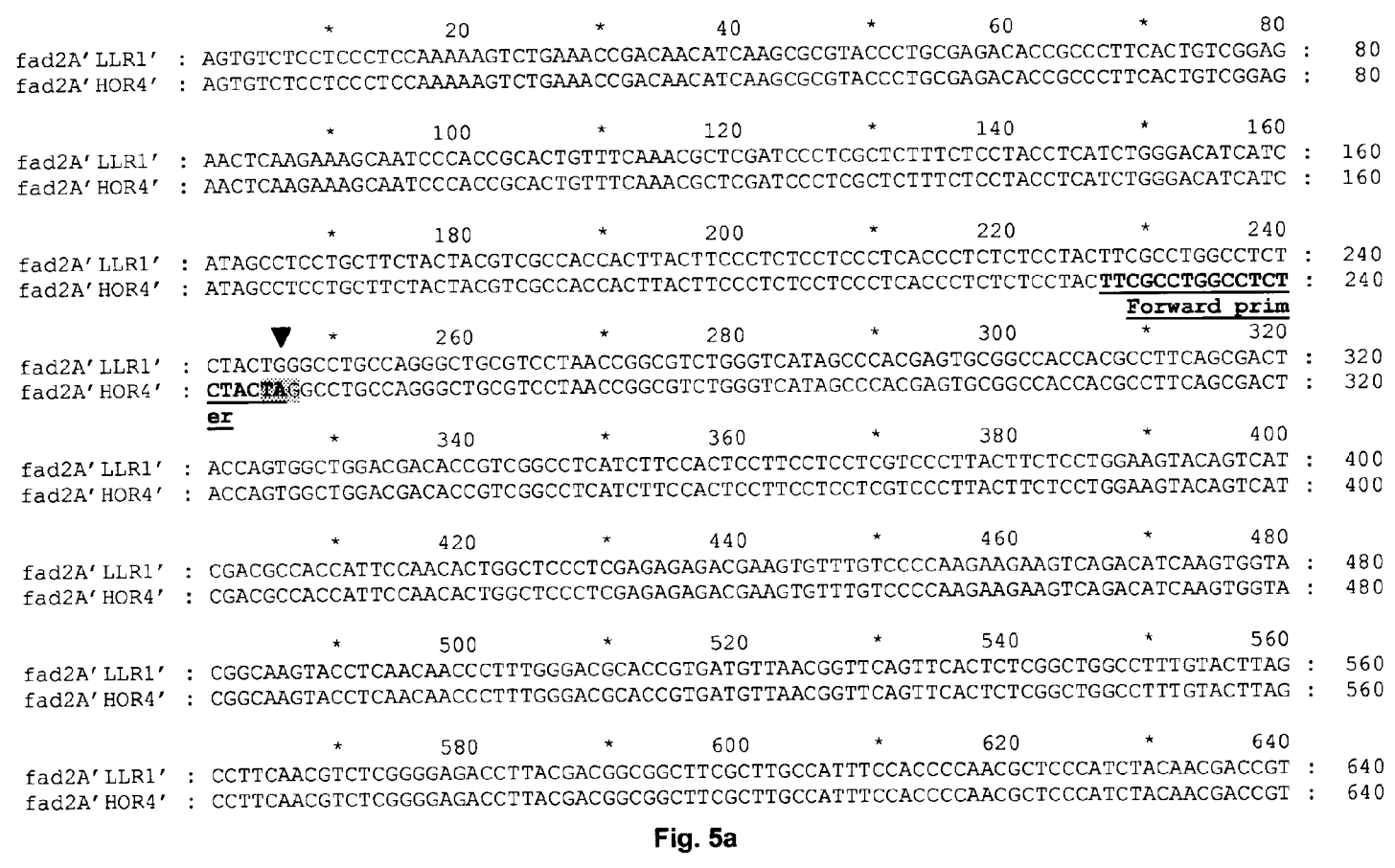

Referring to FIGS. 1-5, primers designed with primer 3 software on fad2 gene sequence from GenBank Accession AY577313 were used to amplify genomic DNA fragments of the fad2 gene from *B. napus* lines 'LLR1#S007', 'LLR1#PR- 2601', 'HOR1#S005', 'HOR1#B005', 'HOR1#NPZ-12', 'HOR2', 'HOR3' and 'HOR4'. The primer pair FAD2BnF1 AGTGTCTCCTCCCTCCAAAAA (SEQ ID NO: 8) and FAD2BnR1: TCTTCTCACCTTGCCTGTCC (SEQ ID NO: 9) amplified a fad2 fragment of the same length (1100 bp) from each of the six parents. The amplified fragments were then cloned and sequenced to investigate the sequence differences of fad2 gene between the five parents.

6. Sequence and Data Analyses

The sequences were analysed and aligned by using Clustal W (Kyoto University Bioinformatics Center) and Genedoc Software (Nicholas et al., 1997). Linkage association between the markers and high oleic trait was determined by t-test analysis.

Results

In this study, 7 'LLR1' clones (both 'LLR1#S007' and 'LLR1#PR-2601'), 12 'HOR1' clones (both 'HOR1#S005', 'HOR1#B005' and 'HOR1#NPZ-12'), 12 'HOR2', 20 'HOR3' and 20 'HOR4' clones were sequenced. The sequence alignment of these clones with *B. rapa* and *B. oleracea* fad2 sequences found in public databases identified:

(1) two fad2 genes originating from *B. rapa* (fad2A) and *B. oleracea* (fad2C) for 'HOR1' lines,
(2) one fad2 gene originating from *B. rapa* (fad2A) for 'HOR2' line,
(3) one fad2 gene originating from *B. rapa* (fad2A) for 'HOR3' line and
(4) one fad2 gene originating from *B. rapa* (fad2A) for 'HOR4' line.

For 'HOR1' lines, the sequence analysis identified a single nucleotide mutation in each fad2 gene.

The single nucleotide mutation in fad2A gene, C to T, at position 752 of the amplified fragment (i.e. position 775 in the full length fad2A gene) occurred in the fad2A gene sequence of all the 'HOR1' clones (both 'HOR1#S005', 'HOR1#B005' and 'HOR1#NPZ-12') (SEQ ID NO: 3) but not the 'LLR1' clones (both 'LLR1#S007' and 'LLR1#PR-2601') (SEQ ID. NO: 1) (see FIG. 1).

The single nucleotide mutation in fad2C gene, C to T, at position 623 of the amplified fragment (i.e. position 646 in the full length fad2C gene) occurred in the fad2C gene sequence of all the 'HOR1' clones (both 'HOR1#S005', 'HOR1#B005' and 'HOR1#NPZ-12') (SEQ ID NO: 4) but not the 'LLR1' clones (both 'LLR1#S007' and 'LLR1#PR-2601') (SEQ ID. NO: 2) (see FIG. 2).

Further analysis indicated that these single nucleotide mutations occurred in the coding sequence of both fad2A and fad2C genes (see FIGS. 6-7). As further shown in FIGS. 1-2 and FIGS. 6-7, the mutations of C to T in fad2A and fad2C genes occurred at the first nucleotide of a codon resulting in a Proline (P) to Serine (S) substitution at amino acid 259 and 216 respectively. After protein annotation using TMHMM Server v. 2.0 (prediction of transmembrane domains, extracellular and intracellular domains), the Proline (P) to serine (S) substitution in FAD2A protein has been localized in an extracellular domain whereas the proline (P) to serine (S) substitution in FAD2C protein has been found in a transmembrane domain. Proline is a non-polar amino acid which tends to reside within the center of the protein whereas Serine is a polar and relatively hydrophobic amino acid which tends to be present on the surface of a protein. These different properties could lead to a structural modification of the FAD2A and FAD2C proteins resulting in a non active delta 12 oleate desaturase.

For 'HOR2' line, the sequence analysis identified a single nucleotide mutation in the fad2A gene. The single nucleotide mutation in fad2A gene, C to T, at position 804 of the amplified fragment (i.e. position 827 in the full length fad2A gene) occurred in the fad2A gene sequence of all the 'HOR2' clones (SEQ ID NO: 5) but not the 'LLR1' clones (both 'LLR1#S007' and 'LLR1#PR-2601') (SEQ ID. NO: 1) (see FIG. 3). Further analysis indicated that this single nucleotide mutation occurred in the coding sequence of fad2A gene (see FIG. 8). As further shown in FIG. 3 and FIG. 8, the mutation of C to T in fad2A gene occurred at the second nucleotide of a codon resulting in a Threonine (T) to Methionine (M) substitution at amino acid 276. After protein annotation using TMHMM Server v. 2.0 (prediction of transmembrane domains, extracellular and intracellular domains), the Threonine (T) to Methionine (M) substitution in FAD2A protein has been localized in an extracellular domain. Methionine (M) is a non-polar amino acid which tends to reside within the center of the protein whereas Threonine (T) is a polar and relatively hydrophobic amino acid which tends to be present on the surface of a protein. These different properties could lead to a structural modification of the FAD2A protein resulting in a non active delta 12 oleate desaturase.

For 'HOR3' line, the sequence analysis identified a single nucleotide mutation in the fad2A gene. The single nucleotide mutation in fad2A gene, C to T, at position 323 of the amplified fragment (i.e. position 346 in the full length fad2A gene) occurred in the fad2A gene sequence of all the 'HOR3' clones (SEQ ID NO: 6) but not the 'LLR1' clones (both 'LLR1#S007' and 'LLR1#PR-2601') (SEQ ID NO: 1) (see FIG. 4). Further analysis indicated that this single nucleotide mutation occurred in the coding sequence of fad2A gene (see FIG. 9). As further shown in FIG. 4 and FIG. 9, the mutation of C to T in fad2A gene occurred at the first nucleotide of a codon creating a stop codon (TAG) that causes early termination of the polypeptide chain during translation. The stop codon results in the incorporation of only 115 amino acids into the polypeptide instead of all 384 amino acids of the full-length polypeptide.

For 'HOR4' line, the sequence analysis identified a single nucleotide mutation in the fad2A gene. The single nucleotide mutation in fad2A gene, G to A, at position 246 of the amplified fragment (i.e. position 269 in the full length fad2A gene) occurred in the fad2A gene sequence of all the 'HOR4' clones (SEQ ID NO: 7) but not the 'LLR1' clones (both 'LLR1S#007' and 'LLR1#PR-2601') (SEQ ID. NO: 1) (see FIG. 5). Further analysis indicated that this single nucleotide mutation occurred in the coding sequence of fad2A gene (see FIG. 10). As further shown in FIG. 5 and FIG. 10, the mutation of G to A in fad2A gene occurred at the first nucleotide of a codon creating a stop codon (TAG) that causes early termination of the polypeptide chain during translation. The stop codon results in the incorporation of only 89 amino acids into the polypeptide instead of all 384 amino acids of the full-length polypeptide.

Molecular tests were developed for genotyping the 6 double haploids populations. For dominant tests, an internal PCR marker has been developed to control the PCR efficiency. A couple of primers (SEQ ID NO: 10 and SEQ ID NO: 11) has been designed on the fad3 gene to amplify a fragment at 57 bp. Forward and reverse PCR primers (SEQ ID NO: 14 and SEQ ID NO: 15 respectively) for detecting the C752T mutation have been used for genotyping DH lines from the cross of 'LLR1#S007' and 'HOR1#S005' (see FIG. 11), the cross of 'LLR1#PR-2601' and 'HOR1#NPZ-12' (data not shown), the cross of 'LLR1#S007' and 'HOR1#B005' (data not shown), the cross of 'LLR1#S007' and 'HOR1#NPZ-12' (data not shown), the cross of 'LLR1#PR-2601' and 'HOR1#B005' (data not shown) and the cross of 'LLR1#PR-2601' and 'HOR1#S005' (data not shown). Forward and reverse PCR primers (SEQ ID NO: 12 and SEQ ID NO: 13 respectively) for detecting the C623T mutation have been used for genotyping DH lines from the cross of 'LLR1#S007' and 'HOR1#S005' (see FIG. 12), the cross of 'LLR1#PR-2601' and 'HOR1#NPZ-12' (data not shown), the cross of 'LLR1#S007' and 'HOR1#B005' (data not shown), the cross of 'LLR1#S007' and 'HOR1#NPZ-12' (data not shown), the cross of 'LLR1#PR-2601' and 'HOR1#B005' (data not shown) and the cross of 'LLR1#PR-2601' and 'HOR1#SO05' (data not shown). Forward and reverse PCR primers (SEQ ID NO: 16 and SEQ ID NO: 17 respectively) for detecting the C804T mutation have been used for testing 'HOR2' and wild type lines (data not shown).

Furthermore, forward and reverse PCR primers have been used for testing 'HOR3' (SEQ ID NO: 34 and SEQ ID NO: 36), 'HOR4' (SEQ ID NO: 35 and SEQ ID NO: 36) and wild type lines.

After genotyping all the 399 DH lines, it was found that the alleles distribution was highly correlated to high C18:1 (see FIG. 13, Table 1).

wild-type homozygote: 14 bp+26 bp+41 bp+66 bp+83 bp
mutated homozygote: 14 bp+41 bp+83 bp+92 bp
heterozygote: 14 bp+26 bp+41 bp+66 bp+83 bp+92 bp For the C346T and G269A mutations (respectively found in 'HOR3' and 'HOR4') the following PCR primers are used:

(SEQ ID NO: 39)
forward primer 5' AGT GTC TCC TCC CTC CAA AAA 3'

(SEQ ID NO: 36)
reverse primer 5' ATC GAG GCA ACT CCT TGG A 3'

The PCR amplification product is cut by the Bfal enzyme, which yields the following differentiated restriction profile:
C346T
wild-type homozygote: 732 bp
mutated homozygote: 410 bp+322 bp
heterozygote: 732 bp+410 bp+322 bp
G269A
wild-type homozygote: 732 bp

TABLE 1

Correlation of the mutant allele-specific markers and oleic acid content in field and greenhouse trials of different DH lines categories.

| | Number of line tested | Average oleic acid content (%) | |
| --- | --- | --- | --- |
| | Greenhouse/Field | Greenhouse | Field |
| Wild type | 119/133 | 63.1 ± 5.8 | 62.6 ± 3.0 |
| With marker FAD2 1C 'HOR1' only | 83/102 | 66.2 ± 5.5 | 66.3 ± 3.0 |
| With marker FAD2 2A 'HOR1' only | 66/79 | 71.5 ± 4.2 | 71 ± 3.3 |
| With marker FAD2 1C 'HOR1' + FAD2 2A 'HOR1' | 57/67 | 77.1 ± 3.1 | 77.7 ± 2.4 |

Besides, PCR primers have been designed in order to provide codominant markers for determining if the mutations are found on only one (heterozygote) or on the two alleles (homozygote) of a fad2 gene.

For the C646 mutation (found in 'HOR1') the following PCR primers are used:

(SEQ ID NO: 37)
forward primer 5' ATT CCA CCC CAA ACC GCT 3'

(SEQ ID NO: 13)
reverse primer 5' AGG CCA CTC CCT GCG 3'

Taking advantage of the introduction of a BsrBl restriction site by the forward primer in the amplified fragment corresponding to the fad2C wild-type gene, the PCR amplification product is cut by the BsrBl enzyme, which yields the following differentiated restriction profile:
wild-type homozygote: 16 bp+108 bp
mutated homozygote: 124 bp
heterozygote: 16 bp+108 bp+124 bp For the C775T mutation (found in 'HOR1') the following PCR primers are used:

(SEQ ID NO: 38)
forward primer 5' TCT ACC GCT ACG CTG CTG TC 3'

(SEQ ID NO: 15)
reverse primer 5' GTG CGT GTC CGT GAT ATT GT 3'

Taking advantage of the suppression of a MnII restriction site in the mutated fad2A gene harbouring the C775T mutation, the PCR amplification product is cut by the MnII enzyme, which yields the following differentiated restriction profile:

mutated homozygote: 244 bp+488 bp
heterozygote: 732 bp+244 bp+488 bp

| SEQ ID NO: | Description |
| --- | --- |
| 1 | Partial nucleotide sequence of 'LLR1' fad2A |
| 2 | Partial nucleotide sequence of 'LLR1' fad2C |
| 3 | Partial nucleotide sequence of 'HOR1' fad2A |
| 4 | Partial nucleotide sequence of 'HOR1' fad2C |
| 5 | Partial nucleotide sequence of 'HOR2' fad2A |
| 6 | Partial nucleotide sequence of 'HOR3' fad2A |
| 7 | Partial nucleotide sequence of 'HOR4' fad2A |
| 8 | PCR primer for amplifying a 1100 bp fad2 fragment |
| 9 | PCR primer for amplifying a 1100 bp fad2 fragment |
| 10 | PCR primer for amplifying a 57 bp fad3 fragment |
| 11 | PCR primer for amplifying a 57 bp fad3 fragment |
| 12 | Forward PCR primer for detecting the C646T mutation ('HOR1') |
| 13 | Reverse PCR primer for detecting the C646T mutation ('HOR1) |
| 14 | Forward PCR primer for detecting the C775T mutation ('HOR1') |
| 15 | Reverse PCR primer for detecting the C775T mutation ('HOR1') |
| 16 | Forward PCR primer for detecting the C827T mutation ('HOR2') |
| 17 | Reverse PCR primer for detecting the C827T mutation ('HOR2') |
| 18 | Exemplary wild type *B. napus* fad2A nucleotide sequence |
| 19 | Exemplary wild type *B. napus* FAD2A protein sequence |
| 20 | Exemplary wild type *B. napus* fad2C nucleotide sequence |
| 21 | Exemplary wild type *B. napus* FAD2C protein sequence |
| 22 | Consensus sequence for mutated fad2 |
| 23 | Consensus sequence for mutated FAD2 |

-continued

| SEQ ID NO: | Description |
|---|---|
| 24 | Nucleotide sequence for G269A mutated fad2 |
| 25 | Protein sequence for W90STOP mutated FAD2 |
| 26 | Nucleotide sequence for C346T mutated fad2 |
| 27 | Protein sequence for Q116STOP mutated FAD2 |
| 28 | Nucleotide sequence for C646T mutated fad2 |
| 29 | Protein sequence for P216S mutated FAD2 |
| 30 | Nucleotide sequence for C775T mutated fad2 |
| 31 | Protein sequence for P259S mutated FAD2 |
| 32 | Nucleotide sequence for C827T mutated fad2 |
| 33 | Protein sequence for T276M mutated FAD2 |
| 34 | Forward PCR primer for detecting the C346T mutation ('HOR3') |
| 35 | Forward PCR primer for detecting the G269A mutation ('HOR4') |
| 36 | Reverse PCR primer for detecting the C346T or G269A mutation ('HOR3/4') |
| 37 | Forward PCR primer for detecting the C646T mutation (codominant) |
| 38 | Forward PCR primer for detecting the C775T mutation (codominant) |
| 39 | Forward PCR primer for detecting the C346T or G269A mutation (codominant) |

References

Bonanome A, Grundy S M. Effect of dietary stearic acid on plasma cholesterol and lipoprotein levels. N Engl J. Med. 1988 May 12; 318(19):1244-8.

Liu, Q., Singh, S., Green, A. (2002). High-Oleic and High-Stearic Cottonseed Oils: Nutritionally Improved Cooking Oils Developed Using Gene Silencing. *J Am Coll Nutr* 21: 205S-211.

Debruyne I. Soybean Oil Processing: Quality Criteria and Flavor Reversion. *Oil Mill Gazetteer*. Volume 110, July 2004.

McCallum, C. M., Comai, L., Greene, E. A., and Henikoff, S. (2000). Targeting induced local lesions IN genomes (TILLING) for plant functional genomics. *Plant Physiol.* 123, 439-442.

Herman E. B. (2005). Media and Techniques for Growth, Regeneration and Storage 2002-2005. Volume 9 of Recent Advances in Plant Tissue Culture. Agricell Report.

Gallais A. (1997). Théorie de la sélection en amélioration des plantes. Editions Masson.

Coventry, J; L Kott and W Beversdorf: 1988. Manual for microspore culture of *Brassica napus*. University of Guelph Technical Bulletin, OAC Publication 0489

Dellaporta S L, Wood J, and Hicks J B (1983) A plant DNA minipreparation: version II. Plant Mol Biol Rep 1: 19-21.

Nicholas K. B., Nicholas Jr H. B. & Deerfield II D. W. (1997) GeneDoc:Analysis and Visualization of Genetic Variation. http://www.psc.edu/biomed/genedoc [accessed on 6 Apr. 2005].

Sambrook J and Russell D W (2001) Molecular cloning: a laboratory manual. Cold Spring Harbor Laboratory Press. Cold Spring Harbor, N.Y.

J. C. Pires, J. Zhao, M. E. Schranz, E. J. Leon, P. A. Quijada, L. N. Lukens and T. C. Osborn (2004). Flowering time divergence and genomic rearrangements in resynthesized *Brassica* polyploids (Brassicaceae). Volume 82 Page 675 Issue 4. Biological Journal of the Linnean Society.

Stan Skrypetz, 2005. Le Bulletin bimensuel. Agriculture et Agroalimentaire Canada. Volume 18 Numéro 17.

Konieczny A, Ausubel F M (1993) A procedure for mapping *Arabidopsis* mutations using co-dominant ecotype-specific PCR-based marker. Plant J 4: 403-410

The invention claimed is:

1. A nucleic acid sequence encoding a mutated delta-12 oleate desaturase enzyme (FAD2) from a plant of *Brassica napus* species, wherein said nucleic acid sequence comprises:
   a) nucleic acid sequence SEQ ID NO:22 in which at least one nucleotide of a codon representing the proline at position 259 of the polypeptide encoded by nucleic acid sequence SEQ ID NO:22 is mutated and produces a non-conservative substitution of said proline at position 259 of the polypeptide encoded by nucleic acid sequence SEQ ID NO:22, or
   b) a nucleic acid sequence having at least 90% identity with the sequence defined in a) and which comprises a mutation producing a non-conservative substitution at an amino acid position corresponding i) to proline at position 259 of the polypeptide encoded by nucleic acid sequence SEQ ID NO:22, and which does not encode a functional FAD2; or
   c) the complementary sequences of the sequence defined in a) or b).

2. A mutated nucleic acid sequence according to claim 1, wherein said mutated nucleic acid sequence is SEQ ID NO: 30.

3. A nucleic acid fragment of a mutated nucleic acid according to claim 1, said fragment comprising at least 10 nucleotides and comprising at least one nucleotide contiguous to at least one codon representing the amino acid at position 259 of the amino acid sequence encoded by the nucleic acid sequence SEQ ID NO: 22 or the complementary sequence of said nucleic acid fragment.

4. A nucleic acid fragment, of a mutated nucleic acid according to claim 1, said fragment comprising at least 10 nucleotides and comprising at least one nucleotide contiguous to at least one codon representing the amino acid at position 259 of the amino acid sequence encoded by nucleic acid sequence SEQ ID NO: 22, or the complementary sequence of said nucleic acid fragment;
   wherein said fragment comprises the mutated nucleotide.

5. A mutated nucleic acid sequence according to claim 1, wherein the codon representing the proline at position 259 of the amino acid sequence encoded by nucleic acid SEQ ID NO: 22 is substituted by a codon representing S.

6. A plant of *Brassica napus* species having an increased oleic acid content, or a part of said plant, wherein the plant comprises at least one nucleic acid according to claim 1.

7. A method for selecting plants of *Brassica napus* species having an increased oleic acid content by mutagenesis, comprising the following steps:
   subjecting a plant of *Brassica napus* species or part of a plant of *Brassica napus* species to a mutagenic treatment,
   regenerating a plant, or part of plants, from said treated plant or part of a plant,
   selecting from the regenerated plants those comprising at least one nucleic acid according to claim 1.

8. A method for selecting plants of *Brassica napus* species having an increased oleic acid content by crossing, comprising the following steps:

crossing a plant of *Brassica napus* species with a parent plant of *Brassica napus* species comprising at least one nucleic acid according to claim 1, selecting from the progeny plants obtained by crossing, those comprising at least one nucleic acid according to claim 1.

9. A method for selecting plants of *Brassica napus* species having an increased oleic acid content by crossing, comprising the following steps:

crossing a plant of *Brassica napus* species with a parent plant of *Brassica napus* species, comprising at least one nucleic acid according to claim 1, selecting from the progeny plants obtained by crossing, those comprising at least one nucleic acid according to claim 1, wherein the parent plant is obtained according to a method for selecting plants of *Brassica napus* species having an increased oleic acid content by mutagenesis, comprising the following steps:

subjecting a plant of *Brassica napus* species or part of a plant of *Brassica napus* species to a mutagenic treatment, regenerating plants from said treated plant or part of a plant, selecting from the regenerated plants those comprising at least one nucleic acid according to claim 1.

10. A method for selecting plants of *Brassica napus* species having an increased oleic acid content by crossing, comprising the following steps:

crossing a plant of *Brassica napus* species with a parent plant of *Brassica napus* species comprising at least one nucleic acid according to claim 1, selecting from the progeny plants obtained by crossing, those comprising at least one nucleic acid according to claim 1, wherein the parent plant is the plant deposited at the NCIMB (Aberdeen, Scotland) on May 17, 2006 under accession number 41400.

11. A kit for the selection of plants having a high oleic acid content, comprising:

at least one plant of *Brassica napus* species, or part of plant of *Brassica napus* species, comprising a mutated nucleic acid of a delta-12 oleate desaturase enzyme (FAD2), wherein said mutated nucleic acid sequence comprises:

a) nucleic acid sequence SEQ ID NO:22 in which at least one nucleotide of a codon representing the proline at position 259 of the polypeptide encoded by nucleic acid sequence SEQ ID NO:22 is mutated and produces a non-conservative substitution of said proline at position 259 of the polypeptide encoded by nucleic acid sequence SEQ ID NO:22, or b) a nucleic acid sequence having at least 90% identity with the sequence defined in a) or b) and which comprises a mutation producing a non-conservative substitution at an amino acid position corresponding i) to proline at position 259 of the polypeptide encoded by nucleic acid sequence SEQ ID NO:22; or c) the complementary sequences of the sequence defined in a) or, b), and at least one nucleic acid according to claim 3.

12. A method for selecting plants of *Brassica napus* species having an increased oleic acid content by mutagenesis, comprising the following steps:

subjecting a plant of *Brassica napus* species or part of a plant of *Brassica napus* species to a mutagenic treatment, regenerating plants, from said treated plant or part of a plant, selecting from the regenerated plants those comprising at least one nucleic acid according to claim 1;

or for selecting plants of *Brassica napus* species having an increased oleic acid content by crossing, comprising the following steps:

crossing a plant of *Brassica napus* species with a parent plant of *Brassica napus* species comprising at least one nucleic acid according to claim 1, selecting from the progeny plants obtained by crossing, those comprising at least one nucleic acid according to claim 1;

wherein the selection step is carried by polymerase chain reaction (PCR).

13. A plant of *Brassica napus* species as obtainable according to a method for selecting plants of *Brassica napus* species having an increased oleic acid content by mutagenesis, comprising the following steps:

subjecting a plant of *Brassica napus* species or part of a plant of *Brassica napus* species to a mutagenic treatment, regenerating plants from said treated plant or part of a plant, selecting from the regenerated plants those comprising at least one nucleic acid according to claim 1;

or for selecting plants of *Brassica napus* species having an increased oleic acid content by crossing, comprising the following steps:

crossing a plant of *Brassica napus* species with a parent plant of *Brassica napus* species comprising at least one nucleic acid according to claim 1, selecting from the progeny plants obtained by crossing, those comprising at least one nucleic acid according to claim 1.

14. The mutated nucleic acid sequence according to claim 1, wherein said mutated nucleic acid sequence further comprises the non-conservative mutation of at least one nucleotide of a codon representing the amino acid at position 216 of the amino acid sequence of said FAD2 when said FAD2 sequence is constituted of 384 amino acids, or a homologous nucleic acid sequence derived from said mutated nucleic acid sequence by substitution, insertion, or deletion of at least one nucleotide, and presenting at least 90% homology with said mutated nucleic acid sequence, provided that said homologous nucleic acid sequence presents said mutation and does not encode a functional FAD2, or a hybridizing nucleic acid sequence which hybridizes under stringent conditions to said mutated nucleic acid sequence, provided that the complementary sequence of said hybridizing nucleic acid sequence presents said mutation and does not encode a functional FAD2, or the complementary sequences of said mutated, homologous, or hybridizing nucleic acid sequences.

15. The mutated nucleic acid sequence according to claim 14, wherein said mutated nucleic acid sequence comprises at least one substitution of the codon representing the amino acid at position 216 of the amino acid sequence of said FAD2 when said FAD2 sequence is constituted of 384 amino acids, by a codon representing any amino acid different from P.

16. The mutated nucleic acid sequence according to claim 15, wherein said codon representing the amino acid at position 216 of the amino acid sequence of said FAD2 when said FAD2 sequence is constituted of 384 amino acids, is substituted by a codon representing S.

17. The mutated nucleic acid sequence according to claim 15, wherein said mutated nucleic acid sequence is represented by SEQ ID NO: 22 and comprises at least:

C to T substitution at position 646 of SEQ 10 NO: 22, and C to T substitution at position 775 of SEQ 10 NO: 22.

18. A plant of *Brassica napus* species having an increased oleic acid content, or a part of said plant, wherein the plant comprises at least one nucleic acid according to claim 14.

19. A method for selecting plants of *Brassica napus* species having an increased oleic acid content by mutagenesis, comprising the following steps:
   subjecting a plant of *Brassica napus* species or part of a plant of *Brassica napus* species to a mutagenic treatment,
   regenerating plants from said treated plant or part of a plant,
   selecting from the regenerated plants those comprising at least one nucleic acid according to claim 14.

20. A method for selecting plants of *Brassica napus* species having an increased oleic acid content by crossing, comprising the following steps:
   crossing a plant of *Brassica napus* species with a parent plant of *Brassica napus* species comprising at least one nucleic acid according to claim 14,
   selecting from the progeny plants obtained by crossing, those comprising at least one nucleic acid according to claim 14.

21. A method for selecting plants of *Brassica napus* species having an increased oleic acid content by crossing, comprising the following steps:
   crossing a plant of *Brassica napus* species with a parent plant of *Brassica napus* species comprising at least one nucleic acid according to claim 14,
   selecting from the progeny plants obtained by crossing, those comprising at least one nucleic acid according to claim 14,
   wherein the parent plant is obtained according to a method for selecting plants of *Brassica napus* species having an increased oleic acid content by mutagenesis, comprising the following steps:
   subjecting a plant of *Brassica napus* species or part of a plant of *Brassica napus* species to a mutagenic treatment,
   regenerating plants from said treated plant or part of a plant,
   selecting from the regenerated plants those comprising at least one nucleic acid according to claim 14.

22. A plant of *Brassica napus* species as obtainable according to a method for selecting plants of *Brassica napus* species having an increased oleic acid content by mutagenesis, comprising the following steps:
   subjecting a plant of *Brassica napus* species or part of a plant of *Brassica napus* species to a mutagenic treatment,
   regenerating plants from said treated plant or part of a plant,
   selecting from the regenerated plants those comprising at least one nucleic acid according to claim 14;
   or for selecting plants of *Brassica napus* species having an increased oleic acid content by crossing, comprising the following steps:
   crossing a plant of *Brassica napus* species with a parent plant of *Brassica napus* species comprising at least one nucleic acid according to claim 14,
   selecting from the progeny plants obtained by crossing, those comprising at least one nucleic acid according to claim 14.

* * * * *

```
SEQUENCE LISTING

<160> NUMBER OF SEQ ID NOS: 40

<210> SEQ ID NO 1
<211> LENGTH: 1100
<212> TYPE: DNA
<213> ORGANISM: Brassica napus

<400> SEQUENCE: 1
agtgtctcct ccctccaaaa agtctgaaac cgacaacatc aagcgcgtac cctgcgagac      60
accgcccttc actgtcggag aactcaagaa agcaatccca ccgcactgtt tcaaacgctc     120
gatccctcgc tctttctcct acctcatctg ggacatcatc atagcctcct gcttctacta     180
cgtcgccacc acttacttcc ctctcctccc tcaccctctc tcctacttcg cctggcctct     240
ctactgggcc tgccagggct gcgtcctaac cggcgtctgg gtcatagccc acgagtgcgg     300
ccaccacgcc ttcagcgact accagtggct ggacgacacc gtcggcctca tcttccactc     360
cttcctcctc gtcccttact tctcctggaa gtacagtcat cgacgccacc attccaacac     420
tggctccctc gagagagacg aagtgtttgt ccccaagaag aagtcagaca tcaagtggta     480
cggcaagtac ctcaacaacc ctttgggacg caccgtgatg ttaacggttc agttcactct     540
cggctggcct ttgtacttag ccttcaacgt ctcggggaga ccttacgacg gcggcttcgc     600
ttgccatttc caccccaacg ctcccatcta caacgaccgt gagcgtctcc agatatacat     660
ctccgacgct ggcatcctcg ccgtctgcta cggtctctac cgctacgctg ctgtccaagg     720
agttgcctct atggtctgct tctacggagt tcctcttctg attgtcaacg ggttcttagt     780
```

```
tttgatcact tacttgcagc acacgcatcc ttccctgcct cactatgact cgtctgagtg     840
ggattggttg aggggagctt tggccaccgt tgacagagac tacggaatct tgaacaaggt     900
cttccacaat atcacggaca cgcacgtggc gcatcacctg ttctcgacca tgccgcatta     960
tcatgcgatg gaagctacga aggcgataaa gccgatactg ggagagtatt atcagttcga    1020
tgggacgccg gtggttaagg cgatgtggag ggaggcgaag gagtgtatct atgtggaacc    1080
ggacaggcaa ggtgagaaga                                                1100
```

<210> SEQ ID NO 2
<211> LENGTH: 1100
<212> TYPE: DNA
<213> ORGANISM: Brassica napus

<400> SEQUENCE: 2

```
agtgtctcct ccctccaaaa agtctgaaac cgacaccatc aagcgcgtac cctgcgagac      60
accgcccttc actgtcggag aactcaagaa agcaatccca ccgcactgtt tcaaacgctc     120
gatccctcgc tctttctcct acctcatctg ggacatcatc atagcctcct gcttctacta     180
cgtcgccacc acttacttcc ctctcctccc tcaccctctc tcctacttcg cctggcctct     240
ctactgggcc tgccaagggt gcgtcctaac cggcgtctgg gtcatagccc acgagtgcgg     300
ccaccacgcc ttcagcgact accagtggct tgacgacacc gtcggtctca tcttccactc     360
cttcctcctc gtcccttact tctcctggaa gtacagtcat cgacgccacc attccaacac     420
tggctcccct gagagagacg aagtgtttgt ccccaagaag aagtcagaca tcaagtggta     480
cggcaagtac ctcaacaacc ctttgggacg caccgtgatg ttaacggttc agttcactct     540
cggctggccg ttgtacttag ccttcaacgt ctcgggaaga ccttacgacg gcggcttcgc     600
ttgccatttc cacccaacg ctcccatcta caacgaccgc gagcgtctcc agatatacat     660
ctccgacgct ggcatcctcg ccgtctgcta cggtctcttc cgttacgccg ccgcgcaggg     720
agtggcctcg atggtctgct tctacggagt cccgcttctg attgtcaatg gtttcctcgt     780
gttgatcact tacttgcagc acacgcatcc ttccctgcct cactacgatt cgtccgagtg     840
ggattggttg aggggagctt tggctaccgt tgacagagac tacggaatct tgaacaaggt     900
cttccacaat attaccgaca cgcacgtggc gcatcatctg ttctccacga tgccgcatta     960
tcacgcgatg gaagctacca aggcgataaa gccgatactg ggagagtatt atcagttcga    1020
tgggacgccg gtggttaagg cgatgtggag ggaggcgaag gagtgtatct atgtggaacc    1080
ggacaggcaa ggtgagaaga                                                1100
```

<210> SEQ ID NO 3
<211> LENGTH: 1100
<212> TYPE: DNA
<213> ORGANISM: Artificial sequence
<220> FEATURE:
<223> OTHER INFORMATION: Partial sequence of Brassica napus fad2A mutant
      (HOR1)

<400> SEQUENCE: 3

```
agtgtctcct ccctccaaaa agtctgaaac cgacaacatc aagcgcgtac cctgcgagac      60
accgcccttc actgtcggag aactcaagaa agcaatccca ccgcactgtt tcaaacgctc     120
gatccctcgc tctttctcct acctcatctg ggacatcatc atagcctcct gcttctacta     180
cgtcgccacc acttacttcc ctctcctccc tcaccctctc tcctacttcg cctggcctct     240
ctactgggcc tgccagggct gcgtcctaac cggcgtctgg gtcatagccc acgagtgcgg     300
```

```
ccaccacgcc ttcagcgact accagtggct ggacgacacc gtcggcctca tcttccactc      360
cttcctcctc gtcccttact tctcctggaa gtacagtcat cgacgccacc attccaacac      420
tggctccctc gagagagacg aagtgtttgt ccccaagaag aagtcagaca tcaagtggta      480
cggcaagtac ctcaacaacc ctttgggacg caccgtgatg ttaacggttc agttcactct      540
cggctggcct ttgtacttag ccttcaacgt ctcggggaga ccttacgacg gcggcttcgc      600
ttgccatttc caccccaacg ctcccatcta caacgaccgt gagcgtctcc agatatacat      660
ctccgacgct ggcatcctcg ccgtctgcta cggtctctac cgctacgctg ctgtccaagg      720
agttgcctct atggtctgct tctacggagt ttctcttctg attgtcaacg ggttcttagt      780
tttgatcact tacttgcagc acacgcatcc ttccctgcct cactatgact cgtctgagtg      840
ggattggttg aggggagctt tggccaccgt tgacagagac tacggaatct tgaacaaggt      900
cttccacaat atcacggaca cgcacgtggc gcatcacctg ttctcgacca tgccgcatta      960
tcatgcgatg gaagctacga aggcgataaa gccgatactg ggagagtatt atcagttcga     1020
tgggacgccg gtggttaagg cgatgtggag ggaggcgaag gagtgtatct atgtggaacc     1080
ggacaggcaa ggtgagaaga                                                  1100
```

<210> SEQ ID NO 4
<211> LENGTH: 1100
<212> TYPE: DNA
<213> ORGANISM: Artificial sequence
<220> FEATURE:
<223> OTHER INFORMATION: Partial sequence of Brassica napus fad2C mutant (HOR1)

<400> SEQUENCE: 4

```
agtgtctcct ccctccaaaa agtctgaaac cgacaccatc aagcgcgtac cctgcgagac       60
accgcccttc actgtcggag aactcaagaa agcaatccca ccgcactgtt tcaaacgctc      120
gatccctcgc tctttctcct acctcatctg ggacatcatc atagcctcct gcttctacta      180
cgtcgccacc acttacttcc ctctcctccc tcaccctctc tcctacttcg cctggcctct      240
ctactgggcc tgccaagggt gcgtcctaac cggcgtctgg gtcatagccc acgagtgcgg      300
ccaccacgcc ttcagcgact accagtggct tgacgacacc gtcggtctca tcttccactc      360
cttcctcctc gtcccttact tctcctggaa gtacagtcat cgacgccacc attccaacac      420
tggctccctc gagagagacg aagtgtttgt ccccaagaag aagtcagaca tcaagtggta      480
cggcaagtac ctcaacaacc ctttgggacg caccgtgatg ttaacggttc agttcactct      540
cggctggcct ttgtacttag ccttcaacgt ctcggggaga ccttacgacg gcggcttcgc      600
ttgccatttc caccccaacg cttccatcta caacgaccgc gagcgtctcc agatatacat      660
ctccgacgct ggcatcctcg ccgtctgcta cggtctcttc cgttacgccg ccgcgcaggg      720
agtggcctcg atggtctgct tctacggagt cccgcttctg attgtcaatg gtttcctcgt      780
gttgatcact tacttgcagc acacgcatcc ttccctgcct cactacgatt cgtccgagtg      840
ggattggttg aggggagctt tggctaccgt tgacagagac tacggaatct tgaacaaggt      900
cttccacaat attaccgaca cgcacgtggc gcatcatctg ttctccacga tgccgcatta      960
tcacgcgatg gaagctacca aggcgataaa gccgatactg ggagagtatt atcagttcga     1020
tgggacgccg gtggttaagg cgatgtggag ggaggcgaag gagtgtatct atgtggaacc     1080
ggacaggcaa ggtgagaaga                                                 1100
```

<210> SEQ ID NO 5

<210> SEQ ID NO 5
<211> LENGTH: 1100
<212> TYPE: DNA
<213> ORGANISM: Artificial sequence
<220> FEATURE:
<223> OTHER INFORMATION: Partial sequence of Brassica napus fad2A mutant
      (HOR2)

<400> SEQUENCE: 5

```
agtgtctcct ccctccaaaa agtctgaaac cgacaacatc aagcgcgtac cctgcgagac    60
accgcccttc actgtcggag aactcaagaa agcaatccca ccgcactgtt tcaaacgctc   120
gatccctcgc tctttctcct acctcatctg ggacatcatc atagcctcct gcttctacta   180
cgtcgccacc acttacttcc ctctcctccc tcaccctctc tcctacttcg cctggcctct   240
ctactgggcc tgccagggct gcgtcctaac cggcgtctgg gtcatagccc acgagtgcgg   300
ccaccacgcc ttcagcgact accagtggct ggacgacacc gtcggcctca tcttccactc   360
cttcctcctc gtcccttact tctcctggaa gtacagtcat cgacgccacc attccaacac   420
tggctccctc gagagagacg aagtgtttgt ccccaagaag aagtcagaca tcaagtggta   480
cggcaagtac ctcaacaacc ctttgggacg caccgtgatg ttaacggttc agttcactct   540
cggctggcct ttgtacttag ccttcaacgt ctcggggaga ccttacgacg gcggcttcgc   600
ttgccatttc caccccaacg ctcccatcta caacgaccgt gagcgtctcc agatatacat   660
ctccgacgct ggcatcctcg ccgtctgcta cggtctctac cgctacgctg ctgtccaagg   720
agttgcctcg atggtctgct tctacggagt tcctcttctg attgtcaacg ggttcttagt   780
tttgatcact tacttgcagc acatgcatcc ttccctgcct cactatgact cgtctgagtg   840
ggattggttg aggggagctt tggccaccgt tgacagagac tacggaatct tgaacaaggt   900
cttccacaat atcacggaca cgcacgtggc gcatcacctg ttctcgacca tgccgcatta   960
tcatgcgatg gaagctacga aggcgataaa gccgatactg ggagagtatt atcagttcga  1020
tgggacgccg gtggttaagg cgatgtggag ggaggcgaag gagtgtatct atgtggaacc  1080
ggacaggcaa ggtgagaaga                                              1100
```

<210> SEQ ID NO 6
<211> LENGTH: 1100
<212> TYPE: DNA
<213> ORGANISM: Artificial sequence
<220> FEATURE:
<223> OTHER INFORMATION: Partial sequence of Brassica napus fad2A mutant
      (HOR3)

<400> SEQUENCE: 6

```
agtgtctcct ccctccaaaa agtctgaaac cgacaacatc aagcgcgtac cctgcgagac    60
accgcccttc actgtcggag aactcaagaa agcaatccca ccgcactgtt tcaaacgctc   120
gatccctcgc tctttctcct acctcatctg ggacatcatc atagcctcct gcttctacta   180
cgtcgccacc acttacttcc ctctcctccc tcaccctctc tcctacttcg cctggcctct   240
ctactgggcc tgccagggct gcgtcctaac cggcgtctgg gtcatagccc acgagtgcgg   300
ccaccacgcc ttcagcgact actagtggct ggacgacacc gtcggcctca tcttccactc   360
cttcctcctc gtcccttact tctcctggaa gtacagtcat cgacgccacc attccaacac   420
tggctccctc gagagagacg aagtgtttgt ccccaagaag aagtcagaca tcaagtggta   480
cggcaagtac ctcaacaacc ctttgggacg caccgtgatg ttaacggttc agttcactct   540
cggctggcct ttgtacttag ccttcaacgt ctcggggaga ccttacgacg gcggcttcgc   600
ttgccatttc caccccaacg ctcccatcta caacgaccgt gagcgtctcc agatatacat   660
```

```
ctccgacgct ggcatcctcg ccgtctgcta cggtctctac cgctacgctg ctgtccaagg    720
agttgcctcg atggtctgct tctacggagt tcctcttctg attgtcaacg ggttcttagt    780
tttgatcact tacttgcagc acacgcatcc ttccctgcct cactatgact cgtctgagtg    840
ggattggttg aggggagctt tggccaccgt tgacagagac tacggaatct tgaacaaggt    900
cttccacaat atcacggaca cgcacgtggc gcatcacctg ttctcgacca tgccgcatta    960
tcatgcgatg aagctacga aggcgataaa gccgatactg ggagagtatt atcagttcga   1020
tgggacgccg gtggttaagg cgatgtggag ggaggcgaag gagtgtatct atgtggaacc   1080
ggacaggcaa ggtgagaaga                                              1100
```

<210> SEQ ID NO 7
<211> LENGTH: 1100
<212> TYPE: DNA
<213> ORGANISM: Artificial sequence
<220> FEATURE:
<223> OTHER INFORMATION: Partial sequence of Brassica napus fad2A mutant
      (HOR4)

<400> SEQUENCE: 7

```
agtgtctcct ccctccaaaa agtctgaaac cgacaacatc aagcgcgtac cctgcgagac     60
accgcccttc actgtcggag aactcaagaa agcaatccca ccgcactgtt tcaaacgctc    120
gatccctcgc tctttctcct acctcatctg ggacatcatc atagcctcct gcttctacta    180
cgtcgccacc acttacttcc ctctcctccc tcaccctctc tcctacttcg cctggcctct    240
ctactaggcc tgccagggct gcgtcctaac cggcgtctgg gtcatagccc acgagtgcgg    300
ccaccacgcc ttcagcgact accagtggct ggacgacacc gtcggcctca tcttccactc    360
cttcctcctc gtccctact tctcctggaa gtacagtcat cgacgccacc attccaacac    420
tggctccctc gagagagacg aagtgtttgt ccccaagaag aagtcagaca tcaagtggta    480
cggcaagtac ctcaacaacc ctttgggacg caccgtgatg ttaacggttc agttcactct    540
cggctggcct ttgtacttag ccttcaacgt ctcggggaga ccttacgacg gcggcttcgc    600
ttgccatttc cactccaacg ctcccatcta caacgaccgt gagcgtctcc agatatacat    660
ctccgacgct ggcatcctcg ccgtctgcta cggtctctac cgctacgctg ctgtccaagg    720
agttgcctcg atggtctgct tctacggagt tcctcttctg attgtcaacg ggttcttagt    780
tttgatcact tacttgcagc acacgcatcc ttccctgcct cactatgact cgtctgagtg    840
ggattggttg aggggagctt tggccaccgt tgacagagac tacggaatct tgaacaaggt    900
cttccacaat atcacggaca cgcacgtggc gcatcacctg ttctcgacca tgccgcatta    960
tcatgcgatg aagctacga aggcgataaa gccgatactg ggagagtatt atcagttcga   1020
tgggacgccg gtggttaagg cgatgtggag ggaggcgaag gagtgtatct atgtggaacc   1080
ggacaggcaa ggtgagaaga                                              1100
```

<210> SEQ ID NO 8
<211> LENGTH: 21
<212> TYPE: DNA
<213> ORGANISM: Artificial sequence
<220> FEATURE:
<223> OTHER INFORMATION: PCR primer

<400> SEQUENCE: 8

```
agtgtctcct ccctccaaaa a                                              21
```

```
<210> SEQ ID NO 9
<211> LENGTH: 20
<212> TYPE: DNA
<213> ORGANISM: Artificial sequence
<220> FEATURE:
<223> OTHER INFORMATION: PCR primer

<400> SEQUENCE: 9
tcttctcacc ttgcctgtcc                                               20

<210> SEQ ID NO 10
<211> LENGTH: 20
<212> TYPE: DNA
<213> ORGANISM: Artificial sequence
<220> FEATURE:
<223> OTHER INFORMATION: PCR primer

<400> SEQUENCE: 10
cttggtggtc gatcatgttg                                               20

<210> SEQ ID NO 11
<211> LENGTH: 20
<212> TYPE: DNA
<213> ORGANISM: Artificial sequence
<220> FEATURE:
<223> OTHER INFORMATION: PCR primer

<400> SEQUENCE: 11
ctggaccaac gaggaatgat                                               20

<210> SEQ ID NO 12
<211> LENGTH: 18
<212> TYPE: DNA
<213> ORGANISM: Artificial sequence
<220> FEATURE:
<223> OTHER INFORMATION: PCR primer

<400> SEQUENCE: 12
atttccaccc caacgctt                                                 18

<210> SEQ ID NO 13
<211> LENGTH: 15
<212> TYPE: DNA
<213> ORGANISM: Artificial sequence
<220> FEATURE:
<223> OTHER INFORMATION: PCR primer

<400> SEQUENCE: 13
aggccactcc ctgcg                                                    15

<210> SEQ ID NO 14
<211> LENGTH: 21
<212> TYPE: DNA
<213> ORGANISM: Artificial sequence
<220> FEATURE:
<223> OTHER INFORMATION: PCR primer

<400> SEQUENCE: 14
tggtctgctt ctacggagtt t                                             21

<210> SEQ ID NO 15
<211> LENGTH: 20
<212> TYPE: DNA
<213> ORGANISM: Artificial sequence
<220> FEATURE:
<223> OTHER INFORMATION: PCR primer
```

<400> SEQUENCE: 15
gtgcgtgtcc gtgatattgt                                                   20

<210> SEQ ID NO 16
<211> LENGTH: 20
<212> TYPE: DNA
<213> ORGANISM: Artificial sequence
<220> FEATURE:
<223> OTHER INFORMATION: PCR primer

<400> SEQUENCE: 16
tctaccgcta cgctgctgtc                                                   20

<210> SEQ ID NO 17
<211> LENGTH: 17
<212> TYPE: DNA
<213> ORGANISM: Artificial sequence
<220> FEATURE:
<223> OTHER INFORMATION: PCR primer

<400> SEQUENCE: 17
aggcagggaa ggatgca                                                      17

<210> SEQ ID NO 18
<211> LENGTH: 1155
<212> TYPE: DNA
<213> ORGANISM: Brassica napus
<220> FEATURE:
<221> NAME/KEY: CDS
<222> LOCATION: (1)..(1155)

<400> SEQUENCE: 18

```
atg ggt gca ggt gga aga atg caa gtg tct cct ccc tcc aaa aag tct         48
Met Gly Ala Gly Gly Arg Met Gln Val Ser Pro Pro Ser Lys Lys Ser
1               5                   10                  15 gaa acc gac aac atc aag cgc gta ccc tgc gag aca ccg ccc ttc act         96
Glu Thr Asp Asn Ile Lys Arg Val Pro Cys Glu Thr Pro Pro Phe Thr
            20                  25                  30 gtc gga gaa ctc aag aaa gca atc cca ccg cac tgt ttc aaa cgc tcg        144
Val Gly Glu Leu Lys Lys Ala Ile Pro Pro His Cys Phe Lys Arg Ser
        35                  40                  45 atc cct cgc tct ttc tcc tac ctc atc tgg gac atc atc ata gcc tcc        192
Ile Pro Arg Ser Phe Ser Tyr Leu Ile Trp Asp Ile Ile Ile Ala Ser
    50                  55                  60 tgc ttc tac tac gtc gcc acc act tac ttc cct ctc ctc cct cac cct        240
Cys Phe Tyr Tyr Val Ala Thr Thr Tyr Phe Pro Leu Leu Pro His Pro
65                  70                  75                  80 ctc tcc tac ttc gcc tgg cct ctc tac tgg gcc tgc cag ggc tgc gtc        288
Leu Ser Tyr Phe Ala Trp Pro Leu Tyr Trp Ala Cys Gln Gly Cys Val
                85                  90                  95 cta acc ggc gtc tgg gtc ata gcc cac gag tgc ggc cac cac gcc ttc        336
Leu Thr Gly Val Trp Val Ile Ala His Glu Cys Gly His His Ala Phe
            100                 105                 110 agc gac tac cag tgg ctg gac gac acc gtc ggc ctc atc ttc cac tcc        384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cga cgc cac        432
Phe Leu Leu Val Pro Tyr Phe Ser Trp Lys Tyr Ser His Arg Arg His
    130                 135                 140 cat tcc aac act ggc tcc ctc gag aga gac gaa gtg ttt gtc ccc aag        480
His Ser Asn Thr Gly Ser Leu Glu Arg Asp Glu Val Phe Val Pro Lys
145                 150                 155                 160
```

```
aag aag tca gac atc aag tgg tac ggc aag tac ctc aac aac cct ttg      528
Lys Lys Ser Asp Ile Lys Trp Tyr Gly Lys Tyr Leu Asn Asn Pro Leu
            165                 170                 175 gga cgc acc gtg atg tta acg gtt cag ttc act ctc ggc tgg cct ttg      576
Gly Arg Thr Val Met Leu Thr Val Gln Phe Thr Leu Gly Trp Pro Leu
                180                 185                 190 tac tta gcc ttc aac gtc tcg ggg aga cct tac gac ggc ggc ttc gct      624
Tyr Leu Ala Phe Asn Val Ser Gly Arg Pro Tyr Asp Gly Gly Phe Ala
            195                 200                 205 tgc cat ttc cac ccc aac gct ccc atc tac aac gac cgt gag cgt ctc      672
Cys His Phe His Pro Asn Ala Pro Ile Tyr Asn Asp Arg Glu Arg Leu
        210                 215                 220 cag ata tac atc tcc gac gct ggc atc ctc gcc gtc tgc tac ggt ctc      720
Gln Ile Tyr Ile Ser Asp Ala Gly Ile Leu Ala Val Cys Tyr Gly Leu
225                 230                 235                 240 tac cgc tac gct gct gtc caa gga gtt gcc tct atg gtc tgc ttc tac      768
Tyr Arg Tyr Ala Ala Val Gln Gly Val Ala Ser Met Val Cys Phe Tyr
                245                 250                 255 gga gtt cct ctt ctg att gtc aac ggg ttc tta gtt ttg atc act tac      816
Gly Val Pro Leu Leu Ile Val Asn Gly Phe Leu Val Leu Ile Thr Tyr
            260                 265                 270 ttg cag cac acg cat cct tcc ctg cct cac tat gac tcg tct gag tgg      864
Leu Gln His Thr His Pro Ser Leu Pro His Tyr Asp Ser Ser Glu Trp
        275                 280                 285 gat tgg ttg agg gga gct ttg gcc acc gtt gac aga gac tac gga atc      912
Asp Trp Leu Arg Gly Ala Leu Ala Thr Val Asp Arg Asp Tyr Gly Ile
    290                 295                 300 ttg aac aag gtc ttc cac aat atc acg gac acg cac gtg gcg cat cac      960
Leu Asn Lys Val Phe His Asn Ile Thr Asp Thr His Val Ala His His
305                 310                 315                 320 ctg ttc tcg acc atg ccg cat tat cat gcg atg gaa gct acg aag gcg     1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg     1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg     1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta     1152
Asp Arg Gln Gly Glu Lys Lys Gly Val Phe Trp Tyr Asn Asn Lys Leu
    370                 375                 380 tga                                                                  1155

<210> SEQ ID NO 19
<211> LENGTH: 384
<212> TYPE: PRT
<213> ORGANISM: Brassica napus

<400> SEQUENCE: 19

Met Gly Ala Gly Gly Arg Met Gln Val Ser Pro Ser Lys Lys Ser
1               5                   10                  15

Glu Thr Asp Asn Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
        50                  55                  60

Cys Phe Tyr Tyr Val Ala Thr Thr Tyr Phe Pro Leu Leu Pro His Pro
```

```
                65                   70                   75                   80
Leu Ser Tyr Phe Ala Trp Pro Leu Tyr Trp Ala Cys Gln Gly Cys Val
                    85                   90                   95

Leu Thr Gly Val Trp Val Ile Ala His Glu Cys Gly His His Ala Phe
                100                  105                  110

Ser Asp Tyr Gln Trp Leu Asp Asp Thr Val Gly Leu Ile Phe His Ser
                115                  120                  125

Phe Leu Leu Val Pro Tyr Phe Ser Trp Lys Tyr Ser His Arg Arg His
130                  135                  140

His Ser Asn Thr Gly Ser Leu Glu Arg Asp Glu Val Phe Val Pro Lys
145                  150                  155                  160

Lys Lys Ser Asp Ile Lys Trp Tyr Gly Lys Tyr Leu Asn Asn Pro Leu
                165                  170                  175

Gly Arg Thr Val Met Leu Thr Val Gln Phe Thr Leu Gly Trp Pro Leu
                180                  185                  190

Tyr Leu Ala Phe Asn Val Ser Gly Arg Pro Tyr Asp Gly Gly Phe Ala
                195                  200                  205

Cys His Phe His Pro Asn Ala Pro Ile Tyr Asn Asp Arg Glu Arg Leu
210                  215                  220

Gln Ile Tyr Ile Ser Asp Ala Gly Ile Leu Ala Val Cys Tyr Gly Leu
225                  230                  235                  240

Tyr Arg Tyr Ala Ala Val Gln Gly Val Ala Ser Met Val Cys Phe Tyr
                245                  250                  255

Gly Val Pro Leu Leu Ile Val Asn Gly Phe Leu Val Leu Ile Thr Tyr
                260                  265                  270

Leu Gln His Thr His Pro Ser Leu Pro His Tyr Asp Ser Ser Glu Trp
                275                  280                  285

Asp Trp Leu Arg Gly Ala Leu Ala Thr Val Asp Arg Asp Tyr Gly Ile
                290                  295                  300

Leu Asn Lys Val Phe His Asn Ile Thr Asp Thr His Val Ala His His
305                  310                  315                  320

Leu Phe Ser Thr Met Pro His Tyr His Ala Met Glu Ala Thr Lys Ala
                325                  330                  335

Ile Lys Pro Ile Leu Gly Glu Tyr Tyr Gln Phe Asp Gly Thr Pro Val
                340                  345                  350

Val Lys Ala Met Trp Arg Glu Ala Lys Glu Cys Ile Tyr Val Glu Pro
                355                  360                  365

Asp Arg Gln Gly Glu Lys Lys Gly Val Phe Trp Tyr Asn Asn Lys Leu
370                  375                  380

<210> SEQ ID NO 20
<211> LENGTH: 1155
<212> TYPE: DNA
<213> ORGANISM: Brassica napus
<220> FEATURE:
<221> NAME/KEY: CDS
<222> LOCATION: (1)..(1155)

<400> SEQUENCE: 20 atg ggt gca ggt gga aga atg caa gtg tct cct ccc tcc aaa aag tct      48
Met Gly Ala Gly Gly Arg Met Gln Val Ser Pro Pro Ser Lys Lys Ser
1               5                   10                  15 gaa acc gac acc atc aag cgc gta ccc tgc gag aca ccg ccc ttc act      96
Glu Thr Asp Thr Ile Lys Arg Val Pro Cys Glu Thr Pro Pro Phe Thr
            20                  25                  30 gtc gga gaa ctc aag aaa gca atc cca ccg cac tgt ttc aaa cgc tcg     144
```

|     |     |     |     |     |     |     |     |     |     |     |     |     |     |     |
|---|---|---|---|---|---|---|---|---|---|---|---|---|---|---|
| Val | Gly | Glu | Leu | Lys | Lys | Ala | Ile | Pro | Pro | His | Cys | Phe | Lys | Arg | Ser |
|     |     | 35  |     |     |     | 40  |     |     |     | 45  |     |     |     |     |     |

```
atc cct cgc tct ttc tcc tac ctc atc tgg gac atc atc ata gcc tcc      192
Ile Pro Arg Ser Phe Ser Tyr Leu Ile Trp Asp Ile Ile Ile Ala Ser
50                  55                  60 tgc ttc tac tac gtc gcc acc act tac ttc cct ctc ctc cct cac cct      240
Cys Phe Tyr Tyr Val Ala Thr Thr Tyr Phe Pro Leu Leu Pro His Pro
65                  70                  75                  80 ctc tcc tac ttc gcc tgg cct ctc tac tgg gcc tgc caa ggg tgc gtc      288
Leu Ser Tyr Phe Ala Trp Pro Leu Tyr Trp Ala Cys Gln Gly Cys Val
            85                  90                  95 cta acc ggc gtc tgg gtc ata gcc cac gag tgc ggc cac cac gcc ttc      336
Leu Thr Gly Val Trp Val Ile Ala His Glu Cys Gly His His Ala Phe
        100                 105                 110 agc gac tac cag tgg ctt gac gac acc gtc ggt ctc atc ttc cac tcc      384
Ser Asp Tyr Gln Trp Leu Asp Asp Thr Val Gly Leu Ile Phe His Ser
    115                 120                 125 ttc ctc ctc gtc cct tac ttc tcc tgg aag tac agt cat cga cgc cac      432
Phe Leu Leu Val Pro Tyr Phe Ser Trp Lys Tyr Ser His Arg Arg His
130                 135                 140 cat tcc aac act ggc tcc ctc gag aga gac gaa gtg ttt gtc ccc aag      480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg      528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg ccg ttg      576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc gct      624
Tyr Leu Ala Phe Asn Val Ser Gly Arg Pro Tyr Asp Gly Gly Phe Ala
        195                 200                 205 tgc cat ttc cac ccc aac gct ccc atc tac aac gac cgc gag cgt ctc      672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc      720
Gln Ile Tyr Ile Ser Asp Ala Gly Ile Leu Ala Val Cys Tyr Gly Leu
225                 230                 235                 240 ttc cgt tac gcc gcc gcg cag gga gtg gcc tcg atg gtc tgc ttc tac      768
Phe Arg Tyr Ala Ala Ala Gln Gly Val Ala Ser Met Val Cys Phe Tyr
                245                 250                 255 gga gtc ccg ctt ctg att gtc aat ggt ttc ctc gtg ttg atc act tac      816
Gly Val Pro Leu Leu Ile Val Asn Gly Phe Leu Val Leu Ile Thr Tyr
            260                 265                 270 ttg cag cac acg cat cct tcc ctg cct cac tac gat tcg tcc gag tgg      864
Leu Gln His Thr His Pro Ser Leu Pro His Tyr Asp Ser Ser Glu Trp
        275                 280                 285 gat tgg ttg agg gga gct ttg gct acc gtt gac aga gac tac gga atc      912
Asp Trp Leu Arg Gly Ala Leu Ala Thr Val Asp Arg Asp Tyr Gly Ile
    290                 295                 300 ttg aac aag gtc ttc cac aat att acc gac acg cac gtg gcg cat cat      960
Leu Asn Lys Val Phe His Asn Ile Thr Asp Thr His Val Ala His His
305                 310                 315                 320 ctg ttc tcc acg atg ccg cat tat cac gcg atg gaa gct acc aag gcg     1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg     1056
Ile Lys Pro Ile Leu Gly Glu Tyr Tyr Gln Phe Asp Gly Thr Pro Val
            340                 345                 350
```

```
gtt aag gcg atg tgg agg gag gcg aag gag tgt atc tat gtg gaa ccg      1104
Val Lys Ala Met Trp Arg Glu Ala Lys Glu Cys Ile Tyr Val Glu Pro
            355                 360                 365 gac agg caa ggt gag aag aaa ggt gtg ttc tgg tac aac aat aag tta      1152
Asp Arg Gln Gly Glu Lys Lys Gly Val Phe Trp Tyr Asn Asn Lys Leu
370                 375                 380 tga                                                                  1155
```

<210> SEQ ID NO 21
<211> LENGTH: 384
<212> TYPE: PRT
<213> ORGANISM: Brassica napus

<400> SEQUENCE: 21

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
        290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
```

```
                325                 330                 335
Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
            370                 375                 380

<210> SEQ ID NO 22
<211> LENGTH: 1155
<212> TYPE: DNA
<213> ORGANISM: Artificial sequence
<220> FEATURE:
<223> OTHER INFORMATION: Brassica napus fad2 mutants
<220> FEATURE:
<221> NAME/KEY: CDS
<222> LOCATION: (1)..(1155)
<220> FEATURE:
<221> NAME/KEY: misc_feature
<222> LOCATION: (59)..(59)
<223> OTHER INFORMATION: A or C
<220> FEATURE:
<221> NAME/KEY: misc_feature
<222> LOCATION: (269)..(269)
<223> OTHER INFORMATION: G or A
<220> FEATURE:
<221> NAME/KEY: misc_feature
<222> LOCATION: (279)..(279)
<223> OTHER INFORMATION: G or A
<220> FEATURE:
<221> NAME/KEY: misc_feature
<222> LOCATION: (282)..(282)
<223> OTHER INFORMATION: C or G
<220> FEATURE:
<221> NAME/KEY: misc_feature
<222> LOCATION: (346)..(346)
<223> OTHER INFORMATION: C or T
<220> FEATURE:
<221> NAME/KEY: misc_feature
<222> LOCATION: (354)..(354)
<223> OTHER INFORMATION: G or T
<220> FEATURE:
<221> NAME/KEY: misc_feature
<222> LOCATION: (369)..(369)
<223> OTHER INFORMATION: C or T
<220> FEATURE:
<221> NAME/KEY: misc_feature
<222> LOCATION: (573)..(573)
<223> OTHER INFORMATION: T or G
<220> FEATURE:
<221> NAME/KEY: misc_feature
<222> LOCATION: (600)..(600)
<223> OTHER INFORMATION: G or A
<220> FEATURE:
<221> NAME/KEY: misc_feature
<222> LOCATION: (646)..(646)
<223> OTHER INFORMATION: C or T
<220> FEATURE:
<221> NAME/KEY: misc_feature
<222> LOCATION: (663)..(663)
<223> OTHER INFORMATION: T or C
<220> FEATURE:
<221> NAME/KEY: misc_feature
<222> LOCATION: (722)..(722)
<223> OTHER INFORMATION: A or T
<220> FEATURE:
<221> NAME/KEY: misc_feature
<222> LOCATION: (726)..(726)
<223> OTHER INFORMATION: C or T
<220> FEATURE:
<221> NAME/KEY: misc_feature
<222> LOCATION: (732)..(732)
<223> OTHER INFORMATION: T or C
<220> FEATURE:
<221> NAME/KEY: misc_feature
```

```
<222> LOCATION: (735)..(735)
<223> OTHER INFORMATION: T or C
<220> FEATURE:
<221> NAME/KEY: misc_feature
<222> LOCATION: (737)..(737)
<223> OTHER INFORMATION: T or C
<220> FEATURE:
<221> NAME/KEY: misc_feature
<222> LOCATION: (738)..(738)
<223> OTHER INFORMATION: C or G
<220> FEATURE:
<221> NAME/KEY: misc_feature
<222> LOCATION: (741)..(741)
<223> OTHER INFORMATION: A or G
<220> FEATURE:
<221> NAME/KEY: misc_feature
<222> LOCATION: (747)..(747)
<223> OTHER INFORMATION: T or G
<220> FEATURE:
<221> NAME/KEY: misc_feature
<222> LOCATION: (753)..(753)
<223> OTHER INFORMATION: T or G
<220> FEATURE:
<221> NAME/KEY: misc_feature
<222> LOCATION: (774)..(774)
<223> OTHER INFORMATION: T or C
<220> FEATURE:
<221> NAME/KEY: misc_feature
<222> LOCATION: (775)..(775)
<223> OTHER INFORMATION: C or T
<220> FEATURE:
<221> NAME/KEY: misc_feature
<222> LOCATION: (777)..(777)
<223> OTHER INFORMATION: T or G
<220> FEATURE:
<221> NAME/KEY: misc_feature
<222> LOCATION: (792)..(792)
<223> OTHER INFORMATION: C or T
<220> FEATURE:
<221> NAME/KEY: misc_feature
<222> LOCATION: (795)..(795)
<223> OTHER INFORMATION: G or T
<220> FEATURE:
<221> NAME/KEY: misc_feature
<222> LOCATION: (799)..(799)
<223> OTHER INFORMATION: T or C
<220> FEATURE:
<221> NAME/KEY: misc_feature
<222> LOCATION: (801)..(801)
<223> OTHER INFORMATION: A or C
<220> FEATURE:
<221> NAME/KEY: misc_feature
<222> LOCATION: (804)..(804)
<223> OTHER INFORMATION: T or G
<220> FEATURE:
<221> NAME/KEY: misc_feature
<222> LOCATION: (827)..(827)
<223> OTHER INFORMATION: C or T
<220> FEATURE:
<221> NAME/KEY: misc_feature
<222> LOCATION: (849)..(849)
<223> OTHER INFORMATION: T or C
<220> FEATURE:
<221> NAME/KEY: misc_feature
<222> LOCATION: (852)..(852)
<223> OTHER INFORMATION: C or T
<220> FEATURE:
<221> NAME/KEY: misc_feature
<222> LOCATION: (858)..(858)
<223> OTHER INFORMATION: T or C
<220> FEATURE:
<221> NAME/KEY: misc_feature
<222> LOCATION: (888)..(888)
<223> OTHER INFORMATION: C or T
<220> FEATURE:
<221> NAME/KEY: misc_feature
<222> LOCATION: (936)..(936)
<223> OTHER INFORMATION: C or T
<220> FEATURE:
```

```
<221> NAME/KEY: misc_feature
<222> LOCATION: (939)..(939)
<223> OTHER INFORMATION: G or C
<220> FEATURE:
<221> NAME/KEY: misc_feature
<222> LOCATION: (960)..(960)
<223> OTHER INFORMATION: C or T
<220> FEATURE:
<221> NAME/KEY: misc_feature
<222> LOCATION: (969)..(969)
<223> OTHER INFORMATION: G or C
<220> FEATURE:
<221> NAME/KEY: misc_feature
<222> LOCATION: (972)..(972)
<223> OTHER INFORMATION: C or G
<220> FEATURE:
<221> NAME/KEY: misc_feature
<222> LOCATION: (987)..(987)
<223> OTHER INFORMATION: T or C
<220> FEATURE:
<221> NAME/KEY: misc_feature
<222> LOCATION: (1002)..(1002)
<223> OTHER INFORMATION: G or C

<400> SEQUENCE: 22
```

| | | | | | | | | | | | | | | | | |
|---|---|---|---|---|---|---|---|---|---|---|---|---|---|---|---|---|
| atg | ggt | gca | ggt | gga | aga | atg | caa | gtg | tct | cct | ccc | tcc | aaa | aag | tct | 48 |
| Met | Gly | Ala | Gly | Gly | Arg | Met | Gln | Val | Ser | Pro | Pro | Ser | Lys | Lys | Ser | |
| 1 | | | | 5 | | | | | 10 | | | | | 15 | | |
| gaa | acc | gac | anc | atc | aag | cgc | gta | ccc | tgc | gag | aca | ccg | ccc | ttc | act | 96 |
| Glu | Thr | Asp | Xaa | Ile | Lys | Arg | Val | Pro | Cys | Glu | Thr | Pro | Pro | Phe | Thr | |
| | | | 20 | | | | | 25 | | | | | 30 | | | |
| gtc | gga | gaa | ctc | aag | aaa | gca | atc | cca | ccg | cac | tgt | ttc | aaa | cgc | tcg | 144 |
| Val | Gly | Glu | Leu | Lys | Lys | Ala | Ile | Pro | Pro | His | Cys | Phe | Lys | Arg | Ser | |
| | 35 | | | | | 40 | | | | | 45 | | | | | |
| atc | cct | cgc | tct | ttc | tcc | tac | ctc | atc | tgg | gac | atc | atc | ata | gcc | tcc | 192 |
| Ile | Pro | Arg | Ser | Phe | Ser | Tyr | Leu | Ile | Trp | Asp | Ile | Ile | Ile | Ala | Ser | |
| 50 | | | | | 55 | | | | | 60 | | | | | | |
| tgc | ttc | tac | tac | gtc | gcc | acc | act | tac | ttc | cct | ctc | ctc | cct | cac | cct | 240 |
| Cys | Phe | Tyr | Tyr | Val | Ala | Thr | Thr | Tyr | Phe | Pro | Leu | Leu | Pro | His | Pro | |
| 65 | | | | 70 | | | | | 75 | | | | | 80 | | |
| ctc | tcc | tac | ttc | gcc | tgg | cct | ctc | tac | tng | gcc | tgc | can | ggn | tgc | gtc | 288 |
| Leu | Ser | Tyr | Phe | Ala | Trp | Pro | Leu | Tyr | Xaa | Ala | Cys | Xaa | Gly | Cys | Val | |
| | | | 85 | | | | | 90 | | | | | 95 | | | |
| cta | acc | ggc | gtc | tgg | gtc | ata | gcc | cac | gag | tgc | ggc | cac | cac | gcc | ttc | 336 |
| Leu | Thr | Gly | Val | Trp | Val | Ile | Ala | His | Glu | Cys | Gly | His | His | Ala | Phe | |
| | | 100 | | | | | 105 | | | | | 110 | | | | |
| agc | gac | tac | nag | tgg | ctn | gac | gac | acc | gtc | ggn | ctc | atc | ttc | cac | tcc | 384 |
| Ser | Asp | Tyr | Xaa | Trp | Xaa | Asp | Asp | Thr | Val | Gly | Leu | Ile | Phe | His | Ser | |
| | | | 115 | | | | | 120 | | | | | 125 | | | |
| ttc | ctc | ctc | gtc | cct | tac | ttc | tcc | tgg | aag | tac | agt | cat | cga | cgc | cac | 432 |
| Phe | Leu | Leu | Val | Pro | Tyr | Phe | Ser | Trp | Lys | Tyr | Ser | His | Arg | Arg | His | |
| | 130 | | | | | 135 | | | | | 140 | | | | | |
| cat | tcc | aac | act | ggc | tcc | ctc | gag | aga | gac | gaa | gtg | ttt | gtc | ccc | aag | 480 |
| His | Ser | Asn | Thr | Gly | Ser | Leu | Glu | Arg | Asp | Glu | Val | Phe | Val | Pro | Lys | |
| 145 | | | | | 150 | | | | | 155 | | | | | 160 | |
| aag | aag | tca | gac | atc | aag | tgg | tac | ggc | aag | tac | ctc | aac | aac | cct | ttg | 528 |
| Lys | Lys | Ser | Asp | Ile | Lys | Trp | Tyr | Gly | Lys | Tyr | Leu | Asn | Asn | Pro | Leu | |
| | | | | 165 | | | | | 170 | | | | | 175 | | |
| gga | cgc | acc | gtg | atg | tta | acg | gtt | cag | ttc | act | ctc | ggc | tgg | ccn | ttg | 576 |
| Gly | Arg | Thr | Val | Met | Leu | Thr | Val | Gln | Phe | Thr | Leu | Gly | Trp | Pro | Leu | |
| | | | 180 | | | | | 185 | | | | | 190 | | | |
| tac | tta | gcc | ttc | aac | gtc | tcg | ggn | aga | cct | tac | gac | ggc | ggc | ttc | gct | 624 |
| Tyr | Leu | Ala | Phe | Asn | Val | Ser | Gly | Arg | Pro | Tyr | Asp | Gly | Gly | Phe | Ala | |
| | | | | 195 | | | | | 200 | | | | | 205 | | |
| tgc | cat | ttc | cac | ccc | aac | gct | ncc | atc | tac | aac | gac | cgn | gag | cgt | ctc | 672 |

```
Cys His Phe His Pro Asn Ala Xaa Ile Tyr Asn Asp Arg Glu Arg Leu
    210                 215                 220 cag ata tac atc tcc gac gct ggc atc ctc gcc gtc tgc tac ggt ctc    720
Gln Ile Tyr Ile Ser Asp Ala Gly Ile Leu Ala Val Cys Tyr Gly Leu
225                 230                 235                 240 tnc cgn tac gcn gcn gnn can gga gtn gcc tcn atg gtc tgc ttc tac    768
Xaa Arg Tyr Ala Ala Xaa Xaa Gly Val Ala Xaa Met Val Cys Phe Tyr
                245                 250                 255 gga gtn ncn ctt ctg att gtc aan ggn ttc ntn gtn ttg atc act tac    816
Gly Val Xaa Leu Leu Ile Val Xaa Gly Phe Xaa Val Leu Ile Thr Tyr
                260                 265                 270 ttg cag cac ang cat cct tcc ctg cct cac tan gan tcg tcn gag tgg    864
Leu Gln His Xaa His Pro Ser Leu Pro His Xaa Xaa Ser Xaa Glu Trp
            275                 280                 285 gat tgg ttg agg gga gct ttg gcn acc gtt gac aga gac tac gga atc    912
Asp Trp Leu Arg Gly Ala Leu Ala Thr Val Asp Arg Asp Tyr Gly Ile
290                 295                 300 ttg aac aag gtc ttc cac aat atn acn gac acg cac gtg gcg cat can    960
Leu Asn Lys Val Phe His Asn Xaa Thr Asp Thr His Val Ala His Xaa
305                 310                 315                 320 ctg ttc tcn acn atg ccg cat tat can gcg atg gaa gct acn aag gcg    1008
Leu Phe Xaa Thr Met Pro His Tyr Xaa Ala Met Glu Ala Thr Lys Ala
                325                 330                 335 ata aag ccg ata ctg gga gag tat tat cag ttc gat ggg acg ccg gtg    1056
Ile Lys Pro Ile Leu Gly Glu Tyr Tyr Gln Phe Asp Gly Thr Pro Val
                340                 345                 350 gtt aag gcg atg tgg agg gag gcg aag gag tgt atc tat gtg gaa ccg    1104
Val Lys Ala Met Trp Arg Glu Ala Lys Glu Cys Ile Tyr Val Glu Pro
                355                 360                 365 gac agg caa ggt gag aag aaa ggt gtg ttc tgg tac aac aat aag tta    1152
Asp Arg Gln Gly Glu Lys Lys Gly Val Phe Trp Tyr Asn Asn Lys Leu
370                 375                 380 tga                                                                 1155

<210> SEQ ID NO 23
<211> LENGTH: 384
<212> TYPE: PRT
<213> ORGANISM: Artificial sequence
<220> FEATURE:
<221> NAME/KEY: misc_feature
<222> LOCATION: (20)..(20)
<223> OTHER INFORMATION: The 'Xaa' at location 20 stands for Asn or Thr.
<220> FEATURE:
<221> NAME/KEY: misc_feature
<222> LOCATION: (90)..(90)
<223> OTHER INFORMATION: The 'Xaa' at location 90 stands for Trp or
      STOP.
<220> FEATURE:
<221> NAME/KEY: misc_feature
<222> LOCATION: (93)..(93)
<223> OTHER INFORMATION: The 'Xaa' at location 93 stands for Gln.
<220> FEATURE:
<221> NAME/KEY: misc_feature
<222> LOCATION: (116)..(116)
<223> OTHER INFORMATION: The 'Xaa' at location 116 stands for Gln or
      STOP.
<220> FEATURE:
<221> NAME/KEY: misc_feature
<222> LOCATION: (118)..(118)
<223> OTHER INFORMATION: The 'Xaa' at location 118 stands for Leu.
<220> FEATURE:
<221> NAME/KEY: misc_feature
<222> LOCATION: (216)..(216)
<223> OTHER INFORMATION: The 'Xaa' at location 216 stands for Pro or
      Ser.
<220> FEATURE:
<221> NAME/KEY: misc_feature
```

```
<222> LOCATION: (241)..(241)
<223> OTHER INFORMATION: The 'Xaa' at location 241 stands for Tyr or
      Phe.
<220> FEATURE:
<221> NAME/KEY: misc_feature
<222> LOCATION: (246)..(246)
<223> OTHER INFORMATION: The 'Xaa' at location 246 stands for Ala or
      Val.
<220> FEATURE:
<221> NAME/KEY: misc_feature
<222> LOCATION: (247)..(247)
<223> OTHER INFORMATION: The 'Xaa' at location 247 stands for Gln.
<220> FEATURE:
<221> NAME/KEY: misc_feature
<222> LOCATION: (251)..(251)
<223> OTHER INFORMATION: The 'Xaa' at location 251 stands for Ser.
<220> FEATURE:
<221> NAME/KEY: misc_feature
<222> LOCATION: (259)..(259)
<223> OTHER INFORMATION: The 'Xaa' at location 259 stands for Pro or
      Ser.
<220> FEATURE:
<221> NAME/KEY: misc_feature
<222> LOCATION: (264)..(264)
<223> OTHER INFORMATION: The 'Xaa' at location 264 stands for Asn.
<220> FEATURE:
<221> NAME/KEY: misc_feature
<222> LOCATION: (267)..(267)
<223> OTHER INFORMATION: The 'Xaa' at location 267 stands for Leu.
<220> FEATURE:
<221> NAME/KEY: misc_feature
<222> LOCATION: (276)..(276)
<223> OTHER INFORMATION: The 'Xaa' at location 276 stands for Thr or
      Met.
<220> FEATURE:
<221> NAME/KEY: misc_feature
<222> LOCATION: (283)..(283)
<223> OTHER INFORMATION: The 'Xaa' at location 283 stands for Tyr.
<220> FEATURE:
<221> NAME/KEY: misc_feature
<222> LOCATION: (284)..(284)
<223> OTHER INFORMATION: The 'Xaa' at location 284 stands for Asp.
<220> FEATURE:
<221> NAME/KEY: misc_feature
<222> LOCATION: (286)..(286)
<223> OTHER INFORMATION: The 'Xaa' at location 286 stands for Ser.
<220> FEATURE:
<221> NAME/KEY: misc_feature
<222> LOCATION: (312)..(312)
<223> OTHER INFORMATION: The 'Xaa' at location 312 stands for Ile.
<220> FEATURE:
<221> NAME/KEY: misc_feature
<222> LOCATION: (320)..(320)
<223> OTHER INFORMATION: The 'Xaa' at location 320 stands for His.
<220> FEATURE:
<221> NAME/KEY: misc_feature
<222> LOCATION: (323)..(323)
<223> OTHER INFORMATION: The 'Xaa' at location 323 stands for Ser.
<220> FEATURE:
<221> NAME/KEY: misc_feature
<222> LOCATION: (329)..(329)
<223> OTHER INFORMATION: The 'Xaa' at location 329 stands for His.
<220> FEATURE:
<223> OTHER INFORMATION: Brassica napus fad2 mutants

<400> SEQUENCE: 23

Met Gly Ala Gly Gly Arg Met Gln Val Ser Pro Pro Ser Lys Lys Ser
1               5                   10                  15

Glu Thr Asp Xaa Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ile Ala Ser
    50                  55                  60
```

```
Cys Phe Tyr Tyr Val Ala Thr Thr Tyr Phe Pro Leu Leu Pro His Pro
 65                  70                  75                  80

Leu Ser Tyr Phe Ala Trp Pro Leu Tyr Xaa Ala Cys Xaa Gly Cys Val
             85                  90                  95

Leu Thr Gly Val Trp Val Ile Ala His Glu Cys Gly His His Ala Phe
            100                 105                 110

Ser Asp Tyr Xaa Trp Xaa Asp Asp Thr Val Gly Leu Ile Phe His Ser
        115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Xaa Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Xaa Arg Tyr Ala Ala Xaa Xaa Gly Val Ala Xaa Met Val Cys Phe Tyr
                245                 250                 255

Gly Val Xaa Leu Leu Ile Val Xaa Gly Phe Xaa Val Leu Ile Thr Tyr
            260                 265                 270

Leu Gln His Xaa His Pro Ser Leu Pro His Xaa Xaa Ser Xaa Glu Trp
        275                 280                 285

Asp Trp Leu Arg Gly Ala Leu Ala Thr Val Asp Arg Asp Tyr Gly Ile
290                 295                 300

Leu Asn Lys Val Phe His Asn Xaa Thr Asp Thr His Val Ala His Xaa
305                 310                 315                 320

Leu Phe Xaa Thr Met Pro His Tyr Xaa Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Gly Val Phe Trp Tyr Asn Asn Lys Leu
370                 375                 380

<210> SEQ ID NO 24
<211> LENGTH: 1155
<212> TYPE: DNA
<213> ORGANISM: Artificial sequence
<220> FEATURE:
<223> OTHER INFORMATION: Brassica napus G269A fad2A mutant
<220> FEATURE:
<221> NAME/KEY: CDS
<222> LOCATION: (1)..(270)

<400> SEQUENCE: 24 atg ggt gca ggt gga aga atg caa gtg tct cct ccc tcc aaa aag tct    48
Met Gly Ala Gly Gly Arg Met Gln Val Ser Pro Pro Ser Lys Lys Ser
 1               5                  10                  15 gaa acc gac aac atc aag cgc gta ccc tgc gag aca ccg ccc ttc act    96
Glu Thr Asp Asn Ile Lys Arg Val Pro Cys Glu Thr Pro Pro Phe Thr
```

```
                20                   25                 30
gtc gga gaa ctc aag aaa gca atc cca ccg cac tgt ttc aaa cgc tcg    144
Val Gly Glu Leu Lys Lys Ala Ile Pro Pro His Cys Phe Lys Arg Ser
         35                  40                 45 atc cct cgc tct ttc tcc tac ctc atc tgg gac atc atc ata gcc tcc    192
Ile Pro Arg Ser Phe Ser Tyr Leu Ile Trp Asp Ile Ile Ile Ala Ser
 50                  55                  60 tgc ttc tac tac gtc gcc acc act tac ttc cct ctc ctc cct cac cct    240
Cys Phe Tyr Tyr Val Ala Thr Thr Tyr Phe Pro Leu Leu Pro His Pro
 65                  70                  75                  80 ctc tcc tac ttc gcc tgg cct ctc tac tag gcctgccagg gctgcgtcct      290
Leu Ser Tyr Phe Ala Trp Pro Leu Tyr
                 85 aaccggcgtc tgggtcatag cccacgagtg cggccaccac gccttcagcg actaccagtg   350 gctggacgac accgtcggcc tcatcttcca ctccttcctc ctcgtccctt acttctcctg   410 gaagtacagt catcgacgcc accattccaa cactggctcc ctcgagagag acgaagtgtt   470 tgtccccaag aagaagtcag acatcaagtg gtacggcaag tacctcaaca acccttggg    530 acgcaccgtg atgttaacgg ttcagttcac tctcggctgg cctttgtact tagccttcaa   590 cgtctcgggg agaccttacg acggcggctt cgcttgccat ttccacccca cgctcccat    650 ctacaacgac cgtgagcgtc tccagatata catctccgac gctggcatcc tcgccgtctg   710 ctacggtctc taccgctacg ctgctgtcca aggagttgcc tctatggtct gcttctacgg   770 agttcctctt ctgattgtca acgggttctt agttttgatc acttacttgc agcacacgca   830 tccttccctg cctcactatg actcgtctga gtgggattgg ttgaggggag ctttggccac   890 cgttgacaga gactacggaa tcttgaacaa ggtcttccac aatatcacgg acacgcacgt   950 ggcgcatcac ctgttctcga ccatgccgca ttatcatgcg atggaagcta cgaaggcgat  1010 aaagccgata ctgggagagt attatcagtt cgatgggacg ccggtggtta aggcgatgtg  1070 gagggaggcg aaggagtgta tctatgtgga accggacagg caaggtgaga agaaaggtgt  1130 gttctggtac aacaataagt tatga                                       1155

<210> SEQ ID NO 25
<211> LENGTH: 89
<212> TYPE: PRT
<213> ORGANISM: Artificial sequence
<220> FEATURE:
<223> OTHER INFORMATION: Brassica napus G269A fad2A mutant

<400> SEQUENCE: 25

Met Gly Ala Gly Gly Arg Met Gln Val Ser Pro Ser Lys Lys Ser
 1               5                  10                  15

Glu Thr Asp Asn Ile Lys Arg Val Pro Cys Glu Thr Pro Pro Phe Thr
                 20                  25                  30

Val Gly Glu Leu Lys Lys Ala Ile Pro Pro His Cys Phe Lys Arg Ser
         35                  40                  45

Ile Pro Arg Ser Phe Ser Tyr Leu Ile Trp Asp Ile Ile Ile Ala Ser
 50                  55                  60

Cys Phe Tyr Tyr Val Ala Thr Thr Tyr Phe Pro Leu Leu Pro His Pro
 65                  70                  75                  80

Leu Ser Tyr Phe Ala Trp Pro Leu Tyr
                 85

<210> SEQ ID NO 26
<211> LENGTH: 1155
```

<212> TYPE: DNA
<213> ORGANISM: Artificial sequence
<220> FEATURE:
<223> OTHER INFORMATION: Brassica napus fad2A C346T mutant
<220> FEATURE:
<221> NAME/KEY: CDS
<222> LOCATION: (1)..(348)

<400> SEQUENCE: 26

| | | | | | | | | | | | | | | | | |
|---|---|---|---|---|---|---|---|---|---|---|---|---|---|---|---|---|
| atg | ggt | gca | ggt | gga | aga | atg | caa | gtg | tct | cct | ccc | tcc | aaa | aag | tct | 48 |
| Met | Gly | Ala | Gly | Gly | Arg | Met | Gln | Val | Ser | Pro | Pro | Ser | Lys | Lys | Ser | |
| 1 | | | | 5 | | | | | 10 | | | | | 15 | | |
| gaa | acc | gac | aac | atc | aag | cgc | gta | ccc | tgc | gag | aca | ccg | ccc | ttc | act | 96 |
| Glu | Thr | Asp | Asn | Ile | Lys | Arg | Val | Pro | Cys | Glu | Thr | Pro | Pro | Phe | Thr | |
| | | | 20 | | | | | 25 | | | | | 30 | | | |
| gtc | gga | gaa | ctc | aag | aaa | gca | atc | cca | ccg | cac | tgt | ttc | aaa | cgc | tcg | 144 |
| Val | Gly | Glu | Leu | Lys | Lys | Ala | Ile | Pro | Pro | His | Cys | Phe | Lys | Arg | Ser | |
| | | 35 | | | | | 40 | | | | | 45 | | | | |
| atc | cct | cgc | tct | ttc | tcc | tac | ctc | atc | tgg | gac | atc | ata | gcc | tcc | | 192 |
| Ile | Pro | Arg | Ser | Phe | Ser | Tyr | Leu | Ile | Trp | Asp | Ile | Ile | Ala | Ser | | |
| | 50 | | | | | 55 | | | | | 60 | | | | | |
| tgc | ttc | tac | tac | gtc | gcc | acc | act | tac | ttc | cct | ctc | ctc | cct | cac | cct | 240 |
| Cys | Phe | Tyr | Tyr | Val | Ala | Thr | Thr | Tyr | Phe | Pro | Leu | Leu | Pro | His | Pro | |
| 65 | | | | | 70 | | | | | 75 | | | | | 80 | |
| ctc | tcc | tac | ttc | gcc | tgg | cct | ctc | tac | tgg | gcc | tgc | cag | ggc | tgc | gtc | 288 |
| Leu | Ser | Tyr | Phe | Ala | Trp | Pro | Leu | Tyr | Trp | Ala | Cys | Gln | Gly | Cys | Val | |
| | | | | 85 | | | | | 90 | | | | | 95 | | |
| cta | acc | ggc | gtc | tgg | gtc | ata | gcc | cac | gag | tgc | ggc | cac | cac | gcc | ttc | 336 |
| Leu | Thr | Gly | Val | Trp | Val | Ile | Ala | His | Glu | Cys | Gly | His | His | Ala | Phe | |
| | | | 100 | | | | | 105 | | | | | 110 | | | |
| agc | gac | tac | tag | tggctggacg | acaccgtcgg | cctcatcttc | cactccttcc | | | | | | | | | 388 |
| Ser | Asp | Tyr | | | | | | | | | | | | | | |
| | | 115 | | | | | | | | | | | | | | |

| | | |
|---|---|---|
| tcctcgtccc | ttacttctcc | tggaagtaca | gtcatcgacg | ccaccattcc | aacactggct | 448 |
| ccctcgagag | agacgaagtg | tttgtcccca | agaagaagtc | agacatcaag | tggtacggca | 508 |
| agtacctcaa | caacccttg | ggacgcaccg | tgatgttaac | ggttcagttc | actctcggct | 568 |
| ggcctttgta | cttagccttc | aacgtctcgg | ggagaccta | cgacggcggc | ttcgcttgcc | 628 |
| atttccaccc | caacgctccc | atctacaacg | accgtgagcg | tctccagata | tacatctccg | 688 |
| acgctggcat | cctcgccgtc | tgctacggtc | tctaccgcta | cgctgctgtc | caaggagttg | 748 |
| cctctatggt | ctgcttctac | ggagttcctc | ttctgattgt | caacgggttc | ttagttttga | 808 |
| tcacttactt | gcagcacacg | catccttccc | tgcctcacta | tgactcgtct | gagtgggatt | 868 |
| ggttgagggg | agctttggcc | accgttgaca | gagactacgg | aatcttgaac | aaggtcttcc | 928 |
| acaatatcac | ggacacgcac | gtggcgcatc | acctgttctc | gaccatgccg | cattatcatg | 988 |
| cgatggaagc | tacgaaggcg | ataaagccga | tactgggaga | gtattatcag | ttcgatggga | 1048 |
| cgccggtggt | taaggcgatg | tggagggagg | cgaaggagtg | tatctatgtg | aaccggaca | 1108 |
| ggcaaggtga | gaagaaaggt | gtgttctggt | acaacaataa | gttatga | | 1155 |

<210> SEQ ID NO 27
<211> LENGTH: 115
<212> TYPE: PRT
<213> ORGANISM: Artificial sequence
<220> FEATURE:
<223> OTHER INFORMATION: Brassica napus fad2A C346T mutant

<400> SEQUENCE: 27

Met Gly Ala Gly Gly Arg Met Gln Val Ser Pro Pro Ser Lys Lys Ser

```
                1               5                  10                  15
              Glu Thr Asp Asn Ile Lys Arg Val Pro Cys Glu Thr Pro Phe Thr
                              20                  25                  30

Val Gly Glu Leu Lys Lys Ala Ile Pro Pro His Cys Phe Lys Arg Ser
                              35                  40                  45

Ile Pro Arg Ser Phe Ser Tyr Leu Ile Trp Asp Ile Ile Ala Ser
                  50                  55                  60

Cys Phe Tyr Tyr Val Ala Thr Thr Tyr Phe Pro Leu Leu Pro His Pro
              65                  70                  75                  80

Leu Ser Tyr Phe Ala Trp Pro Leu Tyr Trp Ala Cys Gln Gly Cys Val
                              85                  90                  95

Leu Thr Gly Val Trp Val Ile Ala His Glu Cys Gly His His Ala Phe
                              100                 105                 110

Ser Asp Tyr
                      115

<210> SEQ ID NO 28
<211> LENGTH: 1155
<212> TYPE: DNA
<213> ORGANISM: Artificial sequence
<220> FEATURE:
<223> OTHER INFORMATION: Brassica napus C646T fad2C mutant
<220> FEATURE:
<221> NAME/KEY: CDS
<222> LOCATION: (1)..(1155)

<400> SEQUENCE: 28
```

| | | | | | | | | | | | | | | | | |
|---|---|---|---|---|---|---|---|---|---|---|---|---|---|---|---|---|
| atg | ggt | gca | ggt | gga | aga | atg | caa | gtg | tct | cct | ccc | tcc | aaa | aag | tct | 48 |
| Met | Gly | Ala | Gly | Gly | Arg | Met | Gln | Val | Ser | Pro | Pro | Ser | Lys | Lys | Ser | |
| 1 | | | | 5 | | | | | 10 | | | | | 15 | | |

| gaa | acc | gac | acc | atc | aag | cgc | gta | ccc | tgc | gag | aca | ccg | ccc | ttc | act | 96 |
|---|---|---|---|---|---|---|---|---|---|---|---|---|---|---|---|---|
| Glu | Thr | Asp | Thr | Ile | Lys | Arg | Val | Pro | Cys | Glu | Thr | Pro | Pro | Phe | Thr | |
| | | | 20 | | | | | 25 | | | | | 30 | | | |

| gtc | gga | gaa | ctc | aag | aaa | gca | atc | cca | ccg | cac | tgt | ttc | aaa | cgc | tcg | 144 |
|---|---|---|---|---|---|---|---|---|---|---|---|---|---|---|---|---|
| Val | Gly | Glu | Leu | Lys | Lys | Ala | Ile | Pro | Pro | His | Cys | Phe | Lys | Arg | Ser | |
| | | | 35 | | | | | 40 | | | | | 45 | | | |

| atc | cct | cgc | tct | ttc | tcc | tac | ctc | atc | tgg | gac | atc | atc | ata | gcc | tcc | 192 |
|---|---|---|---|---|---|---|---|---|---|---|---|---|---|---|---|---|
| Ile | Pro | Arg | Ser | Phe | Ser | Tyr | Leu | Ile | Trp | Asp | Ile | Ile | Ile | Ala | Ser | |
| | 50 | | | | | 55 | | | | | 60 | | | | | |

| tgc | ttc | tac | tac | gtc | gcc | acc | act | tac | ttc | cct | ctc | ctc | cct | cac | cct | 240 |
|---|---|---|---|---|---|---|---|---|---|---|---|---|---|---|---|---|
| Cys | Phe | Tyr | Tyr | Val | Ala | Thr | Thr | Tyr | Phe | Pro | Leu | Leu | Pro | His | Pro | |
| 65 | | | | | 70 | | | | | 75 | | | | | 80 | |

| ctc | tcc | tac | ttc | gcc | tgg | cct | ctc | tac | tgg | gcc | tgc | caa | ggg | tgc | gtc | 288 |
|---|---|---|---|---|---|---|---|---|---|---|---|---|---|---|---|---|
| Leu | Ser | Tyr | Phe | Ala | Trp | Pro | Leu | Tyr | Trp | Ala | Cys | Gln | Gly | Cys | Val | |
| | | | | 85 | | | | | 90 | | | | | 95 | | |

| cta | acc | ggc | gtc | tgg | gtc | ata | gcc | cac | gag | tgc | ggc | cac | cac | gcc | ttc | 336 |
|---|---|---|---|---|---|---|---|---|---|---|---|---|---|---|---|---|
| Leu | Thr | Gly | Val | Trp | Val | Ile | Ala | His | Glu | Cys | Gly | His | His | Ala | Phe | |
| | | | 100 | | | | | 105 | | | | | 110 | | | |

| agc | gac | tac | cag | tgg | ctt | gac | gac | acc | gtc | ggt | ctc | atc | ttc | cac | tcc | 384 |
|---|---|---|---|---|---|---|---|---|---|---|---|---|---|---|---|---|
| Ser | Asp | Tyr | Gln | Trp | Leu | Asp | Asp | Thr | Val | Gly | Leu | Ile | Phe | His | Ser | |
| | | 115 | | | | | 120 | | | | | 125 | | | | |

| ttc | ctc | ctc | gtc | cct | tac | ttc | tcc | tgg | aag | tac | agt | cat | cga | cgc | cac | 432 |
|---|---|---|---|---|---|---|---|---|---|---|---|---|---|---|---|---|
| Phe | Leu | Leu | Val | Pro | Tyr | Phe | Ser | Trp | Lys | Tyr | Ser | His | Arg | Arg | His | |
| | 130 | | | | | 135 | | | | | 140 | | | | | |

| cat | tcc | aac | act | ggc | tcc | ctc | gag | aga | gac | gaa | gtg | ttt | gtc | ccc | aag | 480 |
|---|---|---|---|---|---|---|---|---|---|---|---|---|---|---|---|---|
| His | Ser | Asn | Thr | Gly | Ser | Leu | Glu | Arg | Asp | Glu | Val | Phe | Val | Pro | Lys | |
| 145 | | | | | 150 | | | | | 155 | | | | | 160 | |

| aag | aag | tca | gac | atc | aag | tgg | tac | ggc | aag | tac | ctc | aac | aac | cct | ttg | 528 |
|---|---|---|---|---|---|---|---|---|---|---|---|---|---|---|---|---|
| Lys | Lys | Ser | Asp | Ile | Lys | Trp | Tyr | Gly | Lys | Tyr | Leu | Asn | Asn | Pro | Leu | |
| | | | | 165 | | | | | 170 | | | | | 175 | | |

```
gga cgc acc gtg atg tta acg gtt cag ttc act ctc ggc tgg ccg ttg      576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc gct      624
Tyr Leu Ala Phe Asn Val Ser Gly Arg Pro Tyr Asp Gly Gly Phe Ala
            195                 200                 205 tgc cat ttc cac ccc aac gct tcc atc tac aac gac cgc gag cgt ctc      672
Cys His Phe His Pro Asn Ala Ser Ile Tyr Asn Asp Arg Glu Arg Leu
            210                 215                 220 cag ata tac atc tcc gac gct ggc atc ctc gcc gtc tgc tac ggt ctc      720
Gln Ile Tyr Ile Ser Asp Ala Gly Ile Leu Ala Val Cys Tyr Gly Leu
225                 230                 235                 240 ttc cgt tac gcc gcc gcg cag gga gtg gcc tcg atg gtc tgc ttc tac      768
Phe Arg Tyr Ala Ala Ala Gln Gly Val Ala Ser Met Val Cys Phe Tyr
                245                 250                 255 gga gtc ccg ctt ctg att gtc aat ggt ttc ctc gtg ttg atc act tac      816
Gly Val Pro Leu Leu Ile Val Asn Gly Phe Leu Val Leu Ile Thr Tyr
            260                 265                 270 ttg cag cac acg cat cct tcc ctg cct cac tac gat tcg tcc gag tgg      864
Leu Gln His Thr His Pro Ser Leu Pro His Tyr Asp Ser Ser Glu Trp
            275                 280                 285 gat tgg ttg agg gga gct ttg gct acc gtt gac aga gac tac gga atc      912
Asp Trp Leu Arg Gly Ala Leu Ala Thr Val Asp Arg Asp Tyr Gly Ile
            290                 295                 300 ttg aac aag gtc ttc cac aat att acc gac acg cac gtg gcg cat cat      960
Leu Asn Lys Val Phe His Asn Ile Thr Asp Thr His Val Ala His His
305                 310                 315                 320 ctg ttc tcc acg atg ccg cat tat cac gcg atg gaa gct acc aag gcg     1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg     1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg     1104
Val Lys Ala Met Trp Arg Glu Ala Lys Glu Cys Ile Tyr Val Glu Pro
            355                 360                 365 gac agg caa ggt gag aag aaa ggt gtg ttc tgg tac aac aat aag tta     1152
Asp Arg Gln Gly Glu Lys Lys Gly Val Phe Trp Tyr Asn Asn Lys Leu
370                 375                 380 tga                                                                 1155

<210> SEQ ID NO 29
<211> LENGTH: 384
<212> TYPE: PRT
<213> ORGANISM: Artificial sequence
<220> FEATURE:
<223> OTHER INFORMATION: Brassica napus C646T fad2C mutant

<400> SEQUENCE: 29

Met Gly Ala Gly Gly Arg Met Gln Val Ser Pro Pro Ser Lys Lys Ser
1               5                   10                  15

Glu Thr Asp Thr Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80
```

```
Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Ser Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380

<210> SEQ ID NO 30
<211> LENGTH: 1155
<212> TYPE: DNA
<213> ORGANISM: Artificial sequence
<220> FEATURE:
<223> OTHER INFORMATION: Brassica napus C775T fad2A mutant
<220> FEATURE:
<221> NAME/KEY: CDS
<222> LOCATION: (1)..(1155)

<400> SEQUENCE: 30 atg ggt gca ggt gga aga atg caa gtg tct cct ccc tcc aaa aag tct         48
Met Gly Ala Gly Gly Arg Met Gln Val Ser Pro Pro Ser Lys Lys Ser
1               5                   10                  15 gaa acc gac aac atc aag cgc gta ccc tgc gag aca ccg ccc ttc act         96
Glu Thr Asp Asn Ile Lys Arg Val Pro Cys Glu Thr Pro Pro Phe Thr
            20                  25                  30
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gtc | gga | gaa | ctc | aag | aaa | gca | atc | cca | ccg | cac | tgt | ttc | aaa | cgc | tcg | 144 |
| Val | Gly | Glu | Leu | Lys | Lys | Ala | Ile | Pro | Pro | His | Cys | Phe | Lys | Arg | Ser | |
| | | 35 | | | | 40 | | | | 45 | | | | | | |
| atc | cct | cgc | tct | ttc | tcc | tac | ctc | atc | tgg | gac | atc | atc | ata | gcc | tcc | 192 |
| Ile | Pro | Arg | Ser | Phe | Ser | Tyr | Leu | Ile | Trp | Asp | Ile | Ile | Ile | Ala | Ser | |
| | 50 | | | | 55 | | | | 60 | | | | | | | |
| tgc | ttc | tac | tac | gtc | gcc | acc | act | tac | ttc | cct | ctc | ctc | cct | cac | cct | 240 |
| Cys | Phe | Tyr | Tyr | Val | Ala | Thr | Thr | Tyr | Phe | Pro | Leu | Leu | Pro | His | Pro | |
| 65 | | | | 70 | | | | 75 | | | | 80 | | | | |
| ctc | tcc | tac | ttc | gcc | tgg | cct | ctc | tac | tgg | gcc | tgc | cag | ggc | tgc | gtc | 288 |
| Leu | Ser | Tyr | Phe | Ala | Trp | Pro | Leu | Tyr | Trp | Ala | Cys | Gln | Gly | Cys | Val | |
| | | | | 85 | | | | 90 | | | | 95 | | | | |
| cta | acc | ggc | gtc | tgg | gtc | ata | gcc | cac | gag | tgc | ggc | cac | cac | gcc | ttc | 336 |
| Leu | Thr | Gly | Val | Trp | Val | Ile | Ala | His | Glu | Cys | Gly | His | His | Ala | Phe | |
| | | 100 | | | | 105 | | | | 110 | | | | | | |
| agc | gac | tac | cag | tgg | ctg | gac | gac | acc | gtc | ggc | ctc | atc | ttc | cac | tcc | 384 |
| Ser | Asp | Tyr | Gln | Trp | Leu | Asp | Asp | Thr | Val | Gly | Leu | Ile | Phe | His | Ser | |
| | | 115 | | | | 120 | | | | 125 | | | | | | |
| ttc | ctc | ctc | gtc | cct | tac | ttc | tcc | tgg | aag | tac | agt | cat | cga | cgc | cac | 432 |
| Phe | Leu | Leu | Val | Pro | Tyr | Phe | Ser | Trp | Lys | Tyr | Ser | His | Arg | Arg | His | |
| 130 | | | | | 135 | | | | | 140 | | | | | | |
| cat | tcc | aac | act | ggc | tcc | ctc | gag | aga | gac | gaa | gtg | ttt | gtc | ccc | aag | 480 |
| His | Ser | Asn | Thr | Gly | Ser | Leu | Glu | Arg | Asp | Glu | Val | Phe | Val | Pro | Lys | |
| 145 | | | | | 150 | | | | | 155 | | | | | 160 | |
| aag | aag | tca | gac | atc | aag | tgg | tac | ggc | aag | tac | ctc | aac | aac | cct | ttg | 528 |
| Lys | Lys | Ser | Asp | Ile | Lys | Trp | Tyr | Gly | Lys | Tyr | Leu | Asn | Asn | Pro | Leu | |
| | | | | 165 | | | | | 170 | | | | | 175 | | |
| gga | cgc | acc | gtg | atg | tta | acg | gtt | cag | ttc | act | ctc | ggc | tgg | cct | ttg | 576 |
| Gly | Arg | Thr | Val | Met | Leu | Thr | Val | Gln | Phe | Thr | Leu | Gly | Trp | Pro | Leu | |
| | | | 180 | | | | | 185 | | | | | 190 | | | |
| tac | tta | gcc | ttc | aac | gtc | tcg | ggg | aga | cct | tac | gac | ggc | ggc | ttc | gct | 624 |
| Tyr | Leu | Ala | Phe | Asn | Val | Ser | Gly | Arg | Pro | Tyr | Asp | Gly | Gly | Phe | Ala | |
| | | 195 | | | | | 200 | | | | | 205 | | | | |
| tgc | cat | ttc | cac | ccc | aac | gct | ccc | atc | tac | aac | gac | cgt | gag | cgt | ctc | 672 |
| Cys | His | Phe | His | Pro | Asn | Ala | Pro | Ile | Tyr | Asn | Asp | Arg | Glu | Arg | Leu | |
| | 210 | | | | | 215 | | | | | 220 | | | | | |
| cag | ata | tac | atc | tcc | gac | gct | ggc | atc | ctc | gcc | gtc | tgc | tac | ggt | ctc | 720 |
| Gln | Ile | Tyr | Ile | Ser | Asp | Ala | Gly | Ile | Leu | Ala | Val | Cys | Tyr | Gly | Leu | |
| 225 | | | | | 230 | | | | | 235 | | | | | 240 | |
| tac | cgc | tac | gct | gct | gtc | caa | gga | gtt | gcc | tct | atg | gtc | tgc | ttc | tac | 768 |
| Tyr | Arg | Tyr | Ala | Ala | Val | Gln | Gly | Val | Ala | Ser | Met | Val | Cys | Phe | Tyr | |
| | | | | 245 | | | | | 250 | | | | | 255 | | |
| gga | gtt | tct | ctt | ctg | att | gtc | aac | ggg | ttc | tta | gtt | ttg | atc | act | tac | 816 |
| Gly | Val | Ser | Leu | Leu | Ile | Val | Asn | Gly | Phe | Leu | Val | Leu | Ile | Thr | Tyr | |
| | | | 260 | | | | | 265 | | | | | 270 | | | |
| ttg | cag | cac | acg | cat | cct | tcc | ctg | cct | cac | tat | gac | tcg | tct | gag | tgg | 864 |
| Leu | Gln | His | Thr | His | Pro | Ser | Leu | Pro | His | Tyr | Asp | Ser | Ser | Glu | Trp | |
| | | 275 | | | | | 280 | | | | | 285 | | | | |
| gat | tgg | ttg | agg | gga | gct | ttg | gcc | acc | gtt | gac | aga | gac | tac | gga | atc | 912 |
| Asp | Trp | Leu | Arg | Gly | Ala | Leu | Ala | Thr | Val | Asp | Arg | Asp | Tyr | Gly | Ile | |
| | 290 | | | | | 295 | | | | | 300 | | | | | |
| ttg | aac | aag | gtc | ttc | cac | aat | atc | acg | gac | acg | cac | gtg | gcg | cat | cac | 960 |
| Leu | Asn | Lys | Val | Phe | His | Asn | Ile | Thr | Asp | Thr | His | Val | Ala | His | His | |
| 305 | | | | | 310 | | | | | 315 | | | | | 320 | |
| ctg | ttc | tcg | acc | atg | ccg | cat | tat | cat | gcg | atg | gaa | gct | acg | aag | gcg | 1008 |
| Leu | Phe | Ser | Thr | Met | Pro | His | Tyr | His | Ala | Met | Glu | Ala | Thr | Lys | Ala | |
| | | | | 325 | | | | | 330 | | | | | 335 | | |
| ata | aag | ccg | ata | ctg | gga | gag | tat | tat | cag | ttc | gat | ggg | acg | ccg | gtg | 1056 |
| Ile | Lys | Pro | Ile | Leu | Gly | Glu | Tyr | Tyr | Gln | Phe | Asp | Gly | Thr | Pro | Val | |
| | | | 340 | | | | | 345 | | | | | 350 | | | |

```
gtt aag gcg atg tgg agg gag gcg aag gag tgt atc tat gtg gaa ccg   1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta   1152
Asp Arg Gln Gly Glu Lys Lys Gly Val Phe Trp Tyr Asn Asn Lys Leu
370                 375                 380 tga                                                                1155
```

<210> SEQ ID NO 31
<211> LENGTH: 384
<212> TYPE: PRT
<213> ORGANISM: Artificial sequence
<220> FEATURE:
<223> OTHER INFORMATION: Brassica napus C775T fad2A mutant

<400> SEQUENCE: 31

Met Gly Ala Gly Gly Arg Met Gln Val Ser Pro Ser Lys Lys Ser
1               5                   10                  15

Glu Thr Asp Asn Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
        50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Ser Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His

```
                 305                 310                 315                 320
Leu Phe Ser Thr Met Pro His Tyr His Ala Met Glu Ala Thr Lys Ala
                    325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
        370                 375                 380

<210> SEQ ID NO 32
<211> LENGTH: 1155
<212> TYPE: DNA
<213> ORGANISM: Artificial sequence
<220> FEATURE:
<223> OTHER INFORMATION: Brassica napus C827T fad2A mutant
<220> FEATURE:
<221> NAME/KEY: CDS
<222> LOCATION: (1)..(1155)

<400> SEQUENCE: 32
```

| | | | | | | | | | | | | | | | | |
|---|---|---|---|---|---|---|---|---|---|---|---|---|---|---|---|---|
| atg | ggt | gca | ggt | gga | aga | atg | caa | gtg | tct | cct | ccc | tcc | aaa | aag | tct | 48 |
| Met | Gly | Ala | Gly | Gly | Arg | Met | Gln | Val | Ser | Pro | Pro | Ser | Lys | Lys | Ser | |
| 1 | | | | 5 | | | | | 10 | | | | | 15 | | |
| gaa | acc | gac | aac | atc | aag | cgc | gta | ccc | tgc | gag | aca | ccg | ccc | ttc | act | 96 |
| Glu | Thr | Asp | Asn | Ile | Lys | Arg | Val | Pro | Cys | Glu | Thr | Pro | Pro | Phe | Thr | |
| | | | 20 | | | | | 25 | | | | | 30 | | | |
| gtc | gga | gaa | ctc | aag | aaa | gca | atc | cca | ccg | cac | tgt | ttc | aaa | cgc | tcg | 144 |
| Val | Gly | Glu | Leu | Lys | Lys | Ala | Ile | Pro | Pro | His | Cys | Phe | Lys | Arg | Ser | |
| | | 35 | | | | | 40 | | | | | 45 | | | | |
| atc | cct | cgc | tct | ttc | tcc | tac | ctc | atc | tgg | gac | atc | atc | ata | gcc | tcc | 192 |
| Ile | Pro | Arg | Ser | Phe | Ser | Tyr | Leu | Ile | Trp | Asp | Ile | Ile | Ile | Ala | Ser | |
| | 50 | | | | | 55 | | | | | 60 | | | | | |
| tgc | ttc | tac | tac | gtc | gcc | acc | act | tac | ttc | cct | ctc | ctc | cct | cac | cct | 240 |
| Cys | Phe | Tyr | Tyr | Val | Ala | Thr | Thr | Tyr | Phe | Pro | Leu | Leu | Pro | His | Pro | |
| 65 | | | | | 70 | | | | | 75 | | | | | 80 | |
| ctc | tcc | tac | ttc | gcc | tgg | cct | ctc | tac | tgg | gcc | tgc | cag | ggc | tgc | gtc | 288 |
| Leu | Ser | Tyr | Phe | Ala | Trp | Pro | Leu | Tyr | Trp | Ala | Cys | Gln | Gly | Cys | Val | |
| | | | | 85 | | | | | 90 | | | | | 95 | | |
| cta | acc | ggc | gtc | tgg | gtc | ata | gcc | cac | gag | tgc | ggc | cac | cac | gcc | ttc | 336 |
| Leu | Thr | Gly | Val | Trp | Val | Ile | Ala | His | Glu | Cys | Gly | His | His | Ala | Phe | |
| | | | 100 | | | | | 105 | | | | | 110 | | | |
| agc | gac | tac | cag | tgg | ctg | gac | gac | acc | gtc | ggc | ctc | atc | ttc | cac | tcc | 384 |
| Ser | Asp | Tyr | Gln | Trp | Leu | Asp | Asp | Thr | Val | Gly | Leu | Ile | Phe | His | Ser | |
| | | 115 | | | | | 120 | | | | | 125 | | | | |
| ttc | ctc | ctc | gtc | cct | tac | ttc | tcc | tgg | aag | tac | agt | cat | cga | cgc | cac | 432 |
| Phe | Leu | Leu | Val | Pro | Tyr | Phe | Ser | Trp | Lys | Tyr | Ser | His | Arg | Arg | His | |
| | 130 | | | | | 135 | | | | | 140 | | | | | |
| cat | tcc | aac | act | ggc | tcc | ctc | gag | aga | gac | gaa | gtg | ttt | gtc | ccc | aag | 480 |
| His | Ser | Asn | Thr | Gly | Ser | Leu | Glu | Arg | Asp | Glu | Val | Phe | Val | Pro | Lys | |
| 145 | | | | | 150 | | | | | 155 | | | | | 160 | |
| aag | aag | tca | gac | atc | aag | tgg | tac | ggc | aag | tac | ctc | aac | aac | cct | ttg | 528 |
| Lys | Lys | Ser | Asp | Ile | Lys | Trp | Tyr | Gly | Lys | Tyr | Leu | Asn | Asn | Pro | Leu | |
| | | | | 165 | | | | | 170 | | | | | 175 | | |
| gga | cgc | acc | gtg | atg | tta | acg | gtt | cag | ttc | act | ctc | ggc | tgg | cct | ttg | 576 |
| Gly | Arg | Thr | Val | Met | Leu | Thr | Val | Gln | Phe | Thr | Leu | Gly | Trp | Pro | Leu | |
| | | | 180 | | | | | 185 | | | | | 190 | | | |
| tac | tta | gcc | ttc | aac | gtc | tcg | ggg | aga | cct | tac | gac | ggc | ggc | ttc | gct | 624 |
| Tyr | Leu | Ala | Phe | Asn | Val | Ser | Gly | Arg | Pro | Tyr | Asp | Gly | Gly | Phe | Ala | |
| | | | 195 | | | | | 200 | | | | | 205 | | | |

| | | | | | | | | | | | | | | |
|---|---|---|---|---|---|---|---|---|---|---|---|---|---|---|
| tgc | cat | ttc | cac | ccc | aac | gct | ccc | atc | tac | aac | gac | cgt | gag | cgt | ctc | 672 |
| Cys | His | Phe | His | Pro | Asn | Ala | Pro | Ile | Tyr | Asn | Asp | Arg | Glu | Arg | Leu |
| 210 | | | | 215 | | | | | 220 | | | | | | |

| cag | ata | tac | atc | tcc | gac | gct | ggc | atc | ctc | gcc | gtc | tgc | tac | ggt | ctc | 720 |
| Gln | Ile | Tyr | Ile | Ser | Asp | Ala | Gly | Ile | Leu | Ala | Val | Cys | Tyr | Gly | Leu |
| 225 | | | | | 230 | | | | 235 | | | | | 240 | |

| tac | cgc | tac | gct | gct | gtc | caa | gga | gtt | gcc | tct | atg | gtc | tgc | ttc | tac | 768 |
| Tyr | Arg | Tyr | Ala | Ala | Val | Gln | Gly | Val | Ala | Ser | Met | Val | Cys | Phe | Tyr |
| | | | | 245 | | | | | 250 | | | | | 255 | |

| gga | gtt | cct | ctt | ctg | att | gtc | aac | ggg | tta | gtt | ttg | atc | act | tac | | 816 |
| Gly | Val | Pro | Leu | Leu | Ile | Val | Asn | Gly | Phe | Leu | Val | Leu | Ile | Thr | Tyr |
| | | 260 | | | | | 265 | | | | | 270 | | | |

| ttg | cag | cac | atg | cat | cct | tcc | ctg | cct | cac | tat | gac | tcg | tct | gag | tgg | 864 |
| Leu | Gln | His | Met | His | Pro | Ser | Leu | Pro | His | Tyr | Asp | Ser | Ser | Glu | Trp |
| | | 275 | | | | | 280 | | | | | 285 | | | |

| gat | tgg | ttg | agg | gga | gct | ttg | gcc | acc | gtt | gac | aga | gac | tac | gga | atc | 912 |
| Asp | Trp | Leu | Arg | Gly | Ala | Leu | Ala | Thr | Val | Asp | Arg | Asp | Tyr | Gly | Ile |
| | 290 | | | | | 295 | | | | | 300 | | | | |

| ttg | aac | aag | gtc | ttc | cac | aat | atc | acg | gac | acg | cac | gtg | gcg | cat | cac | 960 |
| Leu | Asn | Lys | Val | Phe | His | Asn | Ile | Thr | Asp | Thr | His | Val | Ala | His | His |
| 305 | | | | | 310 | | | | | 315 | | | | | 320 |

| ctg | ttc | tcg | acc | atg | ccg | cat | tat | cat | gcg | atg | gaa | gct | acg | aag | gcg | 1008 |
| Leu | Phe | Ser | Thr | Met | Pro | His | Tyr | His | Ala | Met | Glu | Ala | Thr | Lys | Ala |
| | | | | 325 | | | | | 330 | | | | | 335 | |

| ata | aag | ccg | ata | ctg | gga | gag | tat | tat | cag | ttc | gat | ggg | acg | ccg | gtg | 1056 |
| Ile | Lys | Pro | Ile | Leu | Gly | Glu | Tyr | Tyr | Gln | Phe | Asp | Gly | Thr | Pro | Val |
| | | | 340 | | | | | 345 | | | | | 350 | | |

| gtt | aag | gcg | atg | tgg | agg | gag | gcg | aag | gag | tgt | atc | tat | gtg | gaa | ccg | 1104 |
| Val | Lys | Ala | Met | Trp | Arg | Glu | Ala | Lys | Glu | Cys | Ile | Tyr | Val | Glu | Pro |
| | 355 | | | | | 360 | | | | | 365 | | | | |

| gac | agg | caa | ggt | gag | aag | aaa | ggt | gtg | ttc | tgg | tac | aac | aat | aag | tta | 1152 |
| Asp | Arg | Gln | Gly | Glu | Lys | Lys | Gly | Val | Phe | Trp | Tyr | Asn | Asn | Lys | Leu |
| 370 | | | | | 375 | | | | | 380 | | | | | |

| tga | | | | | | | | | | | | | | | | 1155 |

<210> SEQ ID NO 33
<211> LENGTH: 384
<212> TYPE: PRT
<213> ORGANISM: Artificial sequence
<220> FEATURE:
<223> OTHER INFORMATION: Brassica napus C827T fad2A mutant

<400> SEQUENCE: 33

Met Gly Ala Gly Gly Arg Met Gln Val Ser Pro Pro Ser Lys Lys Ser
1               5                   10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
            130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
            210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Met His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
            370                 375                 380

<210> SEQ ID NO 34
<211> LENGTH: 19
<212> TYPE: DNA
<213> ORGANISM: Artificial sequence
<220> FEATURE:
<223> OTHER INFORMATION: PCR primer

<400> SEQUENCE: 34
cacgccttca gcgactact                                                  19

<210> SEQ ID NO 35
<211> LENGTH: 20
<212> TYPE: DNA
<213> ORGANISM: Artificial sequence
<220> FEATURE:
<223> OTHER INFORMATION: PCR primer

<400> SEQUENCE: 35
ttcgcctggc ctctctacta                                                 20

<210> SEQ ID NO 36
<211> LENGTH: 19
<212> TYPE: DNA
<213> ORGANISM: Artificial sequence
<220> FEATURE:

```
<223> OTHER INFORMATION: PCR primer

<400> SEQUENCE: 36
atcgaggcaa ctccttgga                                                    19

<210> SEQ ID NO 37
<211> LENGTH: 18
<212> TYPE: DNA
<213> ORGANISM: Artificial sequence
<220> FEATURE:
<223> OTHER INFORMATION: PCR primer

<400> SEQUENCE: 37
atttccaccc caaccgct                                                     18

<210> SEQ ID NO 38
<211> LENGTH: 20
<212> TYPE: DNA
<213> ORGANISM: Artificial sequence
<220> FEATURE:
<223> OTHER INFORMATION: PCR primer

<400> SEQUENCE: 38
tctaccgcta cgctgctgtc                                                   20

<210> SEQ ID NO 39
<211> LENGTH: 21
<212> TYPE: DNA
<213> ORGANISM: Artificial sequence
<220> FEATURE:
<223> OTHER INFORMATION: PCR primer

<400> SEQUENCE: 39
agtgtctcct ccctccaaaa a                                                 21

<210> SEQ ID NO 40
<211> LENGTH: 383
<212> TYPE: PRT
<213> ORGANISM: Arabidopsis thaliana

<400> SEQUENCE: 40

Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
                20                  25                  30

Val Gly Asp Leu Lys Lys Ala Ile Pro Pro His Cys Phe Lys Arg Ser
            35                  40                  45

Ile Pro Arg Ser Phe Ser Tyr Leu Ile Ser Asp Ile Ile Ala Ser
        50                  55                  60

Cys Phe Tyr Tyr Val Ala Thr Asn Tyr Phe Ser Leu Leu Pro Gln Pro
65                  70                  75                  80

Leu Ser Tyr Leu Ala Trp Pro Leu Tyr Trp Ala Cys Gln Gly Cys Val
                85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160
```

```
Gln Lys Ser Ala Ile Lys Trp Tyr Gly Lys Tyr Leu Asn Asn Pro Leu
            165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
            245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
            275                 280                 285

Trp Leu Arg Gly Ala Leu Ala Thr Val Asp Arg Asp Tyr Gly Ile Leu
            290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
            325                 330                 335

Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
            355                 360                 365

Arg Glu Gly Asp Lys Lys Gly Val Tyr Trp Tyr Asn Asn Lys Leu
    370                 375                 380
```